US008986931B2

(12) United States Patent
Luo et al.

(10) Patent No.: US 8,986,931 B2
(45) Date of Patent: *Mar. 24, 2015

(54) MULTIPLEX BRANCHED-CHAIN DNA ASSAYS

(71) Applicant: Affymetrix, Inc., Santa Clara, CA (US)

(72) Inventors: Yuling Luo, San Ramon, CA (US); Wen Yang, Mountain View, CA (US)

(73) Assignee: Affymetrix, Inc., Santa Clara, CA (US)

( * ) Notice: Subject to any disclaimer, the term of this patent is extended or adjusted under 35 U.S.C. 154(b) by 28 days.

This patent is subject to a terminal disclaimer.

(21) Appl. No.: 13/839,964

(22) Filed: Mar. 15, 2013

(65) Prior Publication Data
US 2013/0303392 A1 Nov. 14, 2013

Related U.S. Application Data

(63) Continuation of application No. 12/804,904, filed on Jul. 29, 2010, now Pat. No. 8,426,578, which is a continuation of application No. 11/433,081, filed on May 11, 2006, now Pat. No. 7,803,541.

(60) Provisional application No. 60/680,976, filed on May 12, 2005.

(51) Int. Cl.
C12Q 1/68 (2006.01)
C12M 1/34 (2006.01)
C12P 19/34 (2006.01)
C07H 21/04 (2006.01)

(52) U.S. Cl.
CPC ............ *C12Q 1/6837* (2013.01); *C12Q 1/682* (2013.01); *C12Q 1/6834* (2013.01)
USPC ....... 435/6.1; 435/91.1; 435/287.2; 536/23.1; 536/24.3

(58) Field of Classification Search
None
See application file for complete search history.

(56) References Cited

U.S. PATENT DOCUMENTS

| 4,868,105 | A | 9/1989 | Urdea et al. |
| 5,093,232 | A | 3/1992 | Urdea et al. |
| 5,122,599 | A | 6/1992 | Barnett et al. |
| 5,124,246 | A | 6/1992 | Urdea et al. |
| 5,185,244 | A | 2/1993 | Wallace |
| 5,198,357 | A | 3/1993 | Holmovist et al. |
| 5,334,499 | A | 8/1994 | Burdick et al. |
| 5,374,524 | A | 12/1994 | Miller |
| 5,393,672 | A | 2/1995 | Ness et al. |
| 5,543,305 | A | 8/1996 | Cummins et al. |
| 5,606,045 | A | 2/1997 | Dandliker et al. |
| 5,633,134 | A | 5/1997 | Shuber |
| 5,635,352 | A * | 6/1997 | Urdea et al. ................ 435/6.18 |
| 5,681,697 | A | 10/1997 | Urdea et al. |
| 5,681,702 | A | 10/1997 | Collins et al. |
| 5,747,244 | A | 5/1998 | Sheridan et al. |
| 5,780,227 | A | 7/1998 | Sheridan et al. |
| 5,804,684 | A | 9/1998 | Su |
| 5,849,481 | A | 12/1998 | Urdea et al. |
| 5,888,778 | A | 3/1999 | Shuber |
| 5,945,515 | A | 8/1999 | Chomczynski |
| 6,007,994 | A | 12/1999 | Ward et al. |
| 6,221,589 | B1 | 4/2001 | Lane et al. |
| 6,232,462 | B1 | 5/2001 | Collins et al. |
| 6,268,147 | B1 | 7/2001 | Beattie et al. |
| 6,306,643 | B1 | 10/2001 | Gentalen et al. |
| 6,352,827 | B1 | 3/2002 | Lin et al. |
| 6,418,382 | B2 | 7/2002 | Rothberg et al. |
| 6,428,957 | B1 | 8/2002 | Delenstarr |
| 6,472,187 | B1 | 10/2002 | Tonoike et al. |
| 6,562,575 | B1 | 5/2003 | Dahl |
| 6,610,475 | B1 | 8/2003 | Kacian et al. |
| 6,670,464 | B1 | 12/2003 | Shimkets et al. |
| 6,673,914 | B1 | 1/2004 | Hoon |
| 6,852,490 | B2 | 2/2005 | Gentalen et al. |
| 7,033,758 | B2 | 4/2006 | Kenny et al. |
| 2002/0034753 | A1 * | 3/2002 | Yang et al. ................ 435/6 |
| 2002/0034754 | A1 | 3/2002 | Ree et al. |
| 2002/0106644 | A1 | 8/2002 | Rosenow |
| 2002/0172953 | A1 | 11/2002 | Mirkin et al. |
| 2002/0187470 | A1 | 12/2002 | Casey et al. |
| 2003/0165935 | A1 | 9/2003 | Vann et al. |
| 2003/0211489 | A1 | 11/2003 | Shen et al. |
| 2004/0023248 | A1 | 2/2004 | O'Malley |
| 2004/0072231 | A1 | 4/2004 | Mirkin et al. |

(Continued)

FOREIGN PATENT DOCUMENTS

EP 1 428 892 6/2004
WO WO 94/00598 1/1994

(Continued)

OTHER PUBLICATIONS

Al-Shoud et al. (1998),"A sample preparation method which facilitates detection of bacteria in blood cultures by the polymerase chain reaction", J. Microbiol. Meth., 32:217-224.
Application Note from Amersham Biosciences, "Whole genome amplification from crude blood lysates," 2003 (4 pages).
Application Note from Applied Biosystems, "Total RNA purification from whole blood," 2002 (6 pages).
Bach et al. (1999) "Magnetic capture-hybridization method for purification and probing of mRNA for neutral protease of *Bacillus cereus*," Journal for Microbiological Methods, 37:187-192.
Balnaves et al. (1991) "Direct PCR from CVS and blood lysates for detection of cystic fibrosis and Duchenne muscular dystrophy deletions," Nucl. Acids. Res., 19(5):1155.

(Continued)

*Primary Examiner* — Amanda Haney
(74) *Attorney, Agent, or Firm* — Monicia Elrod-Erickson; Quine Intellectual Property Law Group, P.C.

(57) ABSTRACT

Methods of detecting two or more nucleic acids in a multiplex branched-chain DNA assay are provided. Different nucleic acids are captured through cooperative hybridization events on different, identifiable subsets of particles or at different selected positions on a spatially addressable solid support. Compositions, kits, and systems related to the methods are also described.

21 Claims, 13 Drawing Sheets

(56) References Cited

U.S. PATENT DOCUMENTS

| | | | |
|---|---|---|---|
| 2004/0076954 A1* | 4/2004 | Caldwell et al. | 435/6 |
| 2004/0086930 A1 | 5/2004 | Tereba et al. | |
| 2004/0115686 A1 | 6/2004 | Dolginow et al. | |
| 2005/0009063 A1 | 1/2005 | Xia et al. | |
| 2005/0019842 A1 | 1/2005 | Prober et al. | |
| 2005/0037397 A1 | 2/2005 | Mirkin et al. | |
| 2005/0170370 A1 | 8/2005 | Rabbani et al. | |
| 2005/0282220 A1 | 12/2005 | Prober et al. | |
| 2006/0172284 A1 | 8/2006 | Zheng et al. | |
| 2006/0263769 A1 | 11/2006 | Luo et al. | |
| 2006/0286583 A1 | 12/2006 | Luo et al. | |
| 2007/0015188 A1 | 1/2007 | Luo et al. | |
| 2007/0161015 A1 | 7/2007 | Zheng et al. | |
| 2007/0161020 A1 | 7/2007 | Luo et al. | |
| 2008/0038725 A1 | 2/2008 | Luo et al. | |
| 2008/0050746 A1 | 2/2008 | McMaster et al. | |
| 2008/0176242 A1 | 7/2008 | McMaster et al. | |
| 2008/0220979 A1 | 9/2008 | Wang et al. | |
| 2009/0081688 A1 | 3/2009 | Luo et al. | |
| 2009/0170060 A1 | 7/2009 | Kermekchiev et al. | |

FOREIGN PATENT DOCUMENTS

| | | |
|---|---|---|
| WO | WO 01/94632 | 12/2001 |
| WO | WO 2004/020654 | 3/2004 |
| WO | WO 2006/124771 | 11/2006 |
| WO | WO 2007/001986 | 1/2007 |

OTHER PUBLICATIONS

Baner et al. (1991) "Signal amplification of padlock probes by rolling cicle replication," Nucleic Acids. Res. 26(22):5073-5078.
Bortolin et al. (2004) "Analytical validation of the tag-it high-throughput microsphere-based universal array genotyping platform: application to the multiplex detection of a panel of thrombophilia-associated single-nucleotide polymorphims," Clin. Chem., 50(11):2028-2036.
Borucki et al. (2005) "Suspension microarray with dendrimer signal amplification allows direct and high-throughput subtyping of *Listeria monocytogenes* from genomic DNA," J. Clin. Microbiol., 3255-3259.
Burris et al. (1999) "A novel method for analysis of nuclear receptor Y agonist actions on aP2 gene expression detected using branched DNA messenger RNA quantitaion," Molecular Endocrinology, 13(3):410-417.
Bushnell et al. (1999) "ProbeDesigner: for the design of probe sets for branched DNA (bDNA) signal amplification assays," Bioinformatics, 15(5):348-355.
Collins et al. (1997) "A branched DNA signal amplification assay for quantification of nucleic acid targets below 100 molecules/ml," Nucleic Acids Research, 25(15):2979-2984.
Collins et al. (1998) "Branched DNA (bDNA) technology for direct quantification of nucleic acids: design and performance," in Gene Quantification, F. Ferre, ed.
De Vries et al. (2001) "PCR on cell lysates obtained from whole blood circumvents DNA isolation," Clin. Chem. 47(9):1701-1702.
Dimitrov and Zuker (2004) "Prediction of hybridization and melting for double-stranded nucleic acids," BioPhysical Journal, 87(1):215-226.
Flagella et al. (2006) "A multiplex branched DNA assay for parallel quantitative gene expression profiling," Anal. Biochem., 352(1):50-60.
Fulton et al. (1997) "Advanced multiplexed analysis with the FlowMetrix system," Clin Chem., 43:1749-1756.
Genospectra "Product Information Sheet for QuantiGene Plex Human Apoptosis Panel 1," product literature, Oct. 14, 2004, pp. 1-2.
Genospectra "Product Information Sheet for QuantiGene Plex Human Apoptosis Panel 2," product literature, Oct. 14, 2004, pp. 1-2.
Genospectra "Product Information Sheet for QuantiGene Plex Human Cytokine Panel 1," product literature, Oct. 14, 2004, pp. 1-2.
Genospectra "QuantiGene Plex brochure," product literature, Oct. 14, 2004, pp. 1-4.
Genospectra "QuantiGene Plex panel brochure," product literature, Oct. 14, 2004, p. 1.
Genospectra "QuantiGene.RTM. Plex Reagent System Instruction Manual," product literature, Oct. 14, 2004, pp. 1-26.
Gentalen & Chee. (1999) "A novel method for determining linkage between DNA sequences: hybridization to paired probe arrays," Nucleic Acids Research, 27(6):1485-1491.
Hartley and Klaassen (2000) "Detection of chemical-induced differential expression of rat hepatic cytochrome P450 mRNA transcripts using branched DNA signal amplification technology," Drug Metabolism and Disposition, 28(50):608-616.
Hatch et al. (1999) "Rolling circle amplification of DNA immobilized on solic surfaces and its application to multiplex mutation detection," Genetic Anal.—Biomedical Engineering, 15(2):35-40.
Higuchi (1989) "DNA from whole blood for PCR, "Amplifications, 2:1-3 (One page from the Jackson Libaray, http://www.jax.org.imr.whole_blood.html.
Iannone (2000) "Multiplexed single nucleotide polymorphism genotyping by oligonucleotide ligation and flow cytometry," Cytometry, 39(2):131-140.
Kenny et al. (2002) "Detection of viral infection and gene expression in clinical tissue specimens using branched DNA (bDNA) in situ hybridization," J. Histochem. Cytochem., 50(9):1219-1227.
Kern et al. (1996) "An enhanced-sensitivity branched-DNA assay for quantification of human immunodeficiency virus type 1 RNA in plasma," J. Clin. Microbiol., 34(12):3196-3202.
Lewin & Stewart-Haynes (1992) "A simple method for DNA extraction from leukocytes for use in PCR," BioTechniques, 13(4):522-524.
Lo et al. (2000) "Fetal DNA in maternal plasma: biology and diagnostic applications," Clinical Chemistry, 46(12):1903-1906.
Malygin et al. (1996) "Hybridization of two oligodeoxynucleotides to both strands of an RNA hairpin structure increases the efficiency of RNA-DNA duplex formation," FEBS Letters, 392:114-116.
Mercier et al. (1990) "Direct PCR from whole blood, without DNA extraction," Nucl. Acids. Res., 18(19):5908.
Nallur et al. (2001) "Signal amplification by rolling cicle amplification on DNA microarrays," Nucleic Acids. Res., 29(23):E118.
Narayanan (1992) "Overview of principles and current uses of DNA probes in clinical and laboratory medicine." Ann. Clin. Lab. Sci., 22(6):353-376.
Nolte (1998) "Branched DNA signal amplification for direct quantitation of nucleic acid sequences in clinical specimens," Advances in Clinical Chemistry, 33(1):201-235.
Nordvag et al. (1992) "Direct PCR of washed blood cells," BioTechniques, 12(4):490-493.
Player et al. (2001) "Single-copy gene detection using branched DNA (bDNA) in-situ hybridization," The Journal of Histochemistry and Cytochemistry, 49(5):603-611.
Schweitzer & Kingsmore (2001) "Combining nucleic acid amplification and detection," Curr. Op Biotechnol., 12(1):21-27.
Shah et al. (1994) "Novel, ultrasensitive, Q-beta, replicase-amplified hybridization assay for detection of *Chlamydia trachomatis*," J. Clin. Microbio., 32(11):2718-2724.
Shah et al. (1995) "Detection of *Mycobacterium tuberculosis* directly from spiked human sputum by Q-beta replicase-ampliified assay," J. Clin. Microbiol., 33(2):322-328.
Shah et al. (2003) "Ultra-sensitive and specific detections of porcine endogenous retrovirus (PERV) using a sequence-capture real-time PCR approach," J. Virol.Meth., 109:209-216.
Shen et al. (1998) "Quantification of cytokine mRNA in peripheral blood mononuclear cells using branched DNA (bDNA) technology," J.Immunol. Meth., 215(1-2):123-134.
Stone et al. (1996) "Detection of rRNA from four respiratory pathogens using an automated Q.beta. replicase assay," Mol. Cell. Probes, 10:359-370.
Tsai et al. (2003) "Nucleic acid capture assay, a new method for direct quantitation of nucleic acids," Nucleic Acids Research, 31(6):e25.

(56) References Cited

OTHER PUBLICATIONS

Ugozzoli et al. (1992) "Detection of specific alleles by using allele-specific primer extension followed by capture on solid suport," GATA, 9(4):107-112.

Van Cleve et al. (1998) "Direct quantification of HIV by flow cytometry using branched DNA signal amplification," Molecular and Cellular Probes, 12:243-247.

Wang et al. (1997) "Regulation of insulin preRNA splicing by glucose," Proc. Nat. Acad. Sci. USA, 94(9):4360-4365.

Wilber & Urdea (1998) "Quantification of HCV RNA in clinical specimens by branched DNA (bDNA) technology," Methods in Molecular Medicine: Hepatitis C 19:71-78.

Wilson et al. (2005) "A mutiplexed PCR-coupled liquid bead array for the simultaneous detection of four biothreat agents," Mol. Cell. Probes, 19(2):137-144.

Yang et al. (2001) "BADGE, Beads Array for the Detection of Gene Expression, a high-throughput diagnostic bioassay," Genome Res., 11(11):1888-1898.

Zhang et al. (2005) "Small interfering RNA and gene expression analysis using a multiplex branched DNA assay without RNA purification," Journal for Biomolecular Screening, 10(6):549-556.

Zolg et al. (1988) "High salt lysates: a simple method to store blood samples without refrigeration for subsequent use with DNA probes," Am. J. Trop. Med. Hyg., 39(1):33-40.

\* cited by examiner

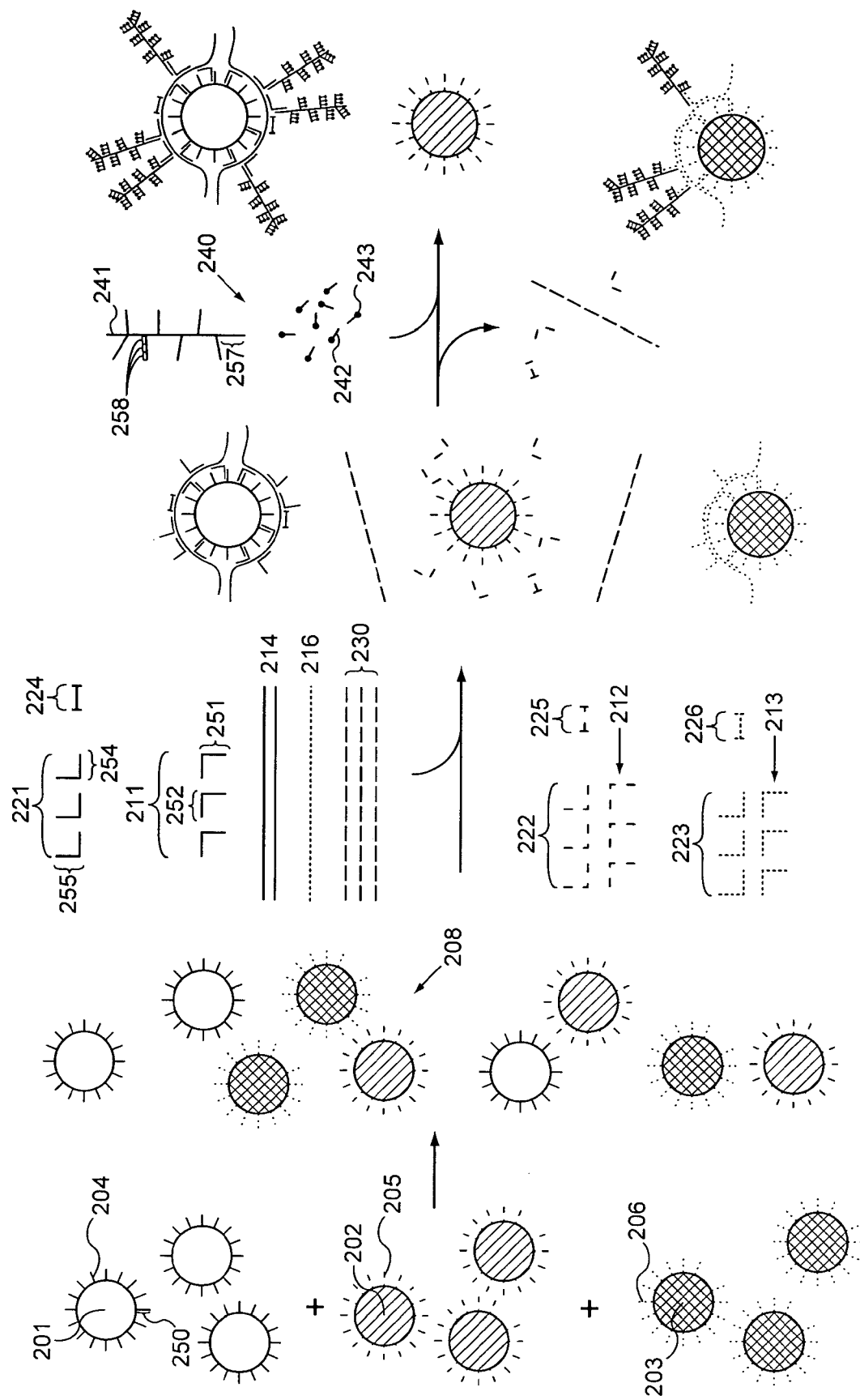

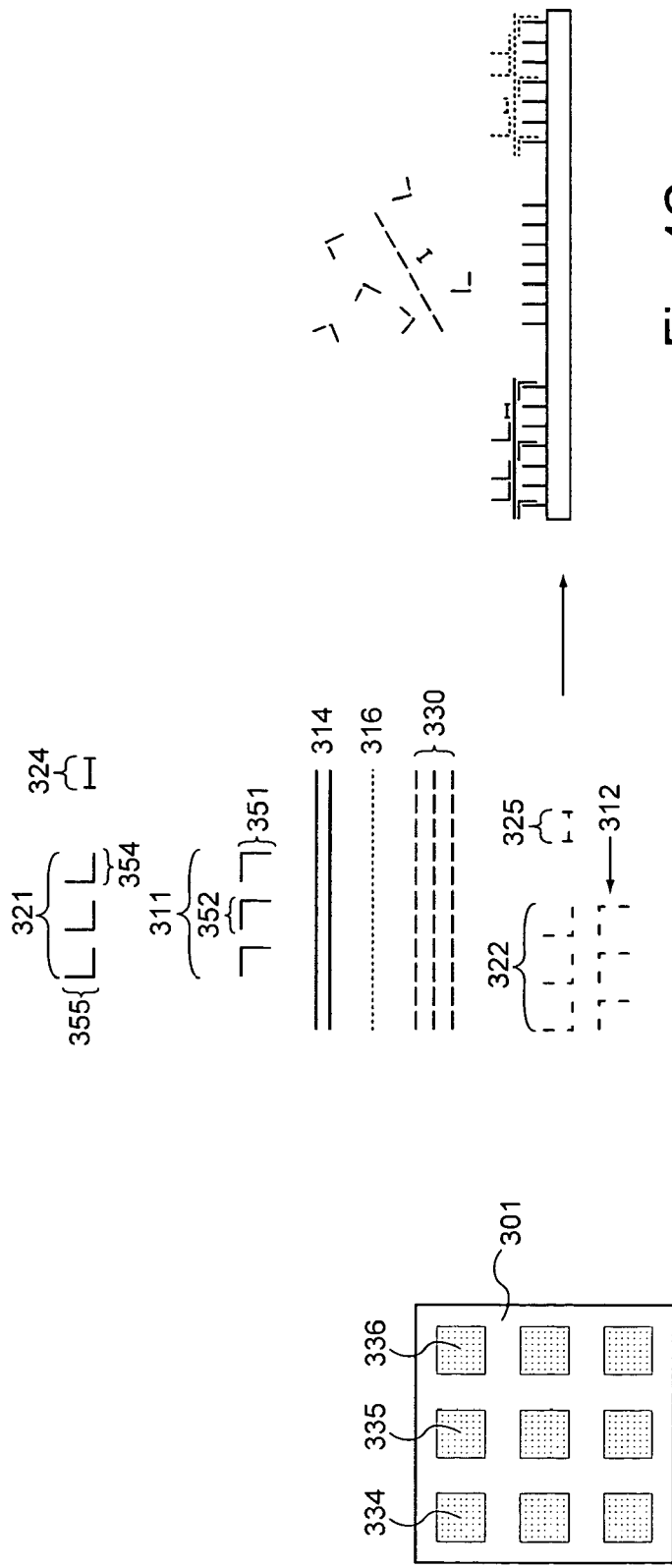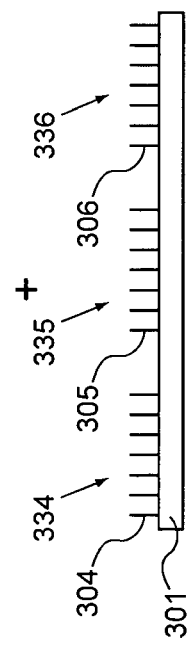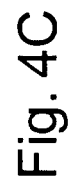

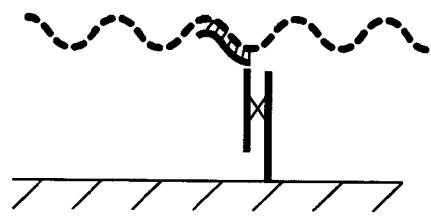
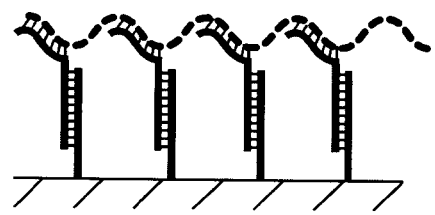
Fig. 6A
Fig. 6B
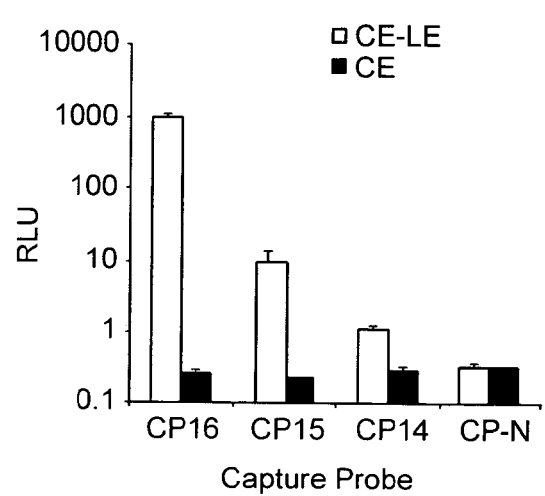
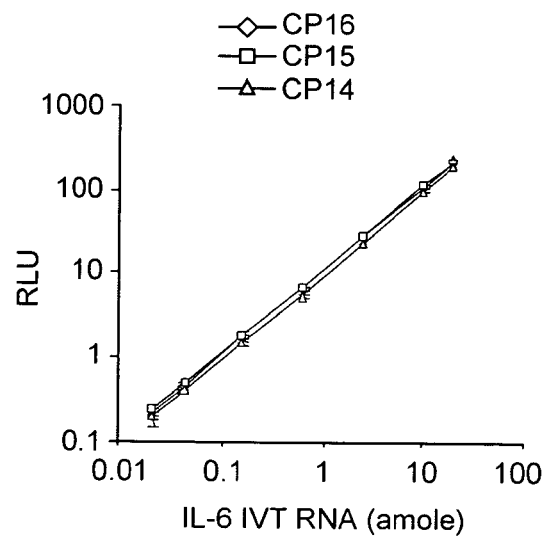
Fig. 6C
Fig. 6D

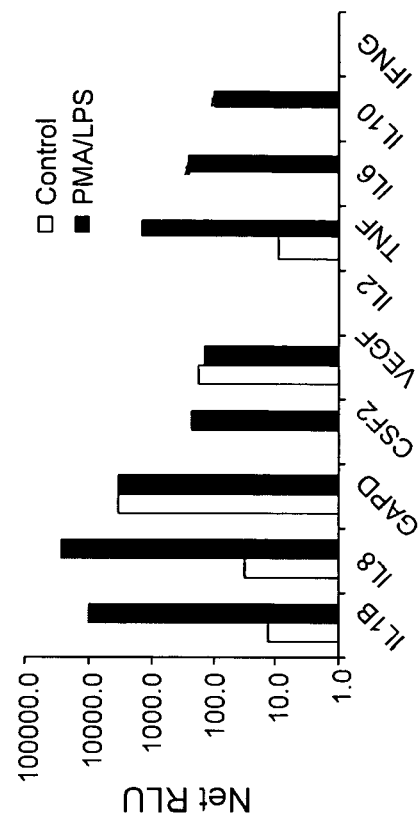
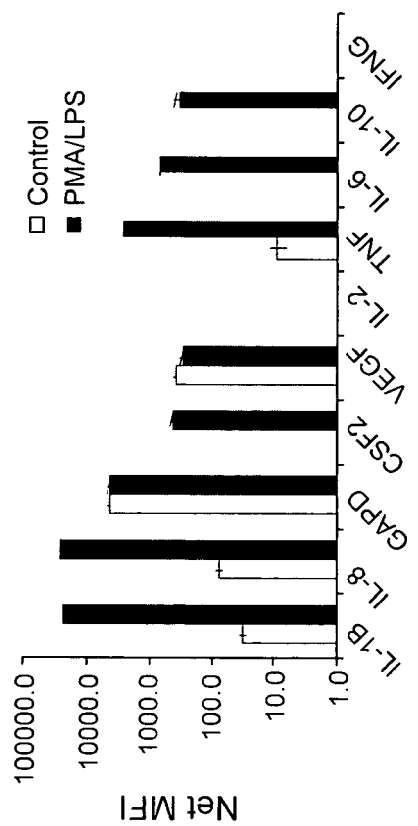
Fig. 8B
Fig. 8A

SEQUENCE LISTING

<160> NUMBER OF SEQ ID NOS: 287

<210> SEQ ID NO 1
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 1
actttctttc caagag                                                     16

<210> SEQ ID NO 2
<211> LENGTH: 15
<212> TYPE: DNA
<213> ORGANISM: Artificial
<220> FEATURE:
<223> OTHER INFORMATION: synthetic oligonucleotide probe

<400> SEQUENCE: 2
actttctttc caaga                                                      15

<210> SEQ ID NO 3
<211> LENGTH: 14
<212> TYPE: DNA
<213> ORGANISM: Artificial
<220> FEATURE:
<223> OTHER INFORMATION: synthetic oligonucleotide probe

<400> SEQUENCE: 3
actttctttc caag                                                       14

<210> SEQ ID NO 4
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 4
aggcatagga cccgtgtctt tttctcttgg aaagaaagt                             39

<210> SEQ ID NO 5
<211> LENGTH: 15
<212> TYPE: DNA
<213> ORGANISM: Artificial
<220> FEATURE:

<223> OTHER INFORMATION: synthetic oligonucleotide probe

<400> SEQUENCE: 5
gggctgggcg agcgg                                                    15

<210> SEQ ID NO 6
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 6
ccagggctgc gtgctg                                                   16

<210> SEQ ID NO 7
<211> LENGTH: 15
<212> TYPE: DNA
<213> ORGANISM: Artificial
<220> FEATURE:
<223> OTHER INFORMATION: synthetic oligonucleotide probe

<400> SEQUENCE: 7
agacgccggg cctcc                                                    15

<210> SEQ ID NO 8
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 8
ccgcaggccc tgcttg                                                   16

<210> SEQ ID NO 9
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 9
tcatggtcaa ggggccct                                                 18

<210> SEQ ID NO 10
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 10
ggggttggag ggcagtgc                                                 18

<210> SEQ ID NO 11
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 11
cagcagtcaa agggatgac a                                              21

<210> SEQ ID NO 12
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 12
caggccacag tgcccaagtt tttaggcata ggacccgtgt ct					42

<210> SEQ ID NO 13
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 13
tggatggcat tcacatgctc tttttaggca taggacccgt gtct					44

<210> SEQ ID NO 14
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 14
gcagtgtctc tactcaggtt caggtttttta ggcataggac ccgtgtct					48

<210> SEQ ID NO 15
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 15
ttctactgtt tcattcatct cagcattttt aggcatagga cccgtgtct					49

<210> SEQ ID NO 16
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 16
ggaggtcaaa catttctgag atgactttt aggcatagga cccgtgtct					49

<210> SEQ ID NO 17
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 17
tgtaggcagg tcggctcctt ttttaggcat aggacccgtg tct					43

<210> SEQ ID NO 18
<211> LENGTH: 44
<212> TYPE: DNA
<213> ORGANISM: Artificial
<220> FEATURE:
<223> OTHER INFORMATION: synthetic oligonucleotide probe

```
<400> SEQUENCE: 18
gggttgcaca ggaagtttcc tttttaggca taggacccgt gtct                   44

<210> SEQ ID NO 19
<211> LENGTH: 50
<212> TYPE: DNA
<213> ORGANISM: Artificial
<220> FEATURE:
<223> OTHER INFORMATION: synthetic oligonucleotide probe

<400> SEQUENCE: 19
tttgaaactt tcaaaggtga taatcttttt taggcatagg acccgtgtct             50

<210> SEQ ID NO 20
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 20
agcagaaagt ccttcaggtt ctcttttttag gcataggacc cgtgtct               47

<210> SEQ ID NO 21
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 21
ctcactcctg gactggctcc tttttaggca taggacccgt gtct                   44

<210> SEQ ID NO 22
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 22
agcagcaggc tctgcagctt tttttgtgca gtgttata                          38

<210> SEQ ID NO 23
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 23
gcgggtgcag agatgctgtt tttttgtgca gtgttata                          38

<210> SEQ ID NO 24
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 24
tacagctcca ggcgggtctt tttttgtgca gtgttata                          38

<210> SEQ ID NO 25
<211> LENGTH: 39
```

```
<212> TYPE: DNA
<213> ORGANISM: Artificial
<220> FEATURE:
<223> OTHER INFORMATION: synthetic oligonucleotide probe

<400> SEQUENCE: 25
tgagcttggt gaggctgcct tttttttgtgc agtgttata                              39

<210> SEQ ID NO 26
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 26
tgcttgtagt ggctggccat tttttttgtgc agtgttata                              39

<210> SEQ ID NO 27
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 27 tttttttta taacactgca caa                                                23

<210> SEQ ID NO 28
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 28
tcagcgccag catcgc                                                        16

<210> SEQ ID NO 29
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 29 gaggggcag agatgatgac                                                     20

<210> SEQ ID NO 30
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 30
aacatggggg catcagca                                                      18

<210> SEQ ID NO 31
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 31
```

-continued

```
catggttcac acccatgacg                                            20

<210> SEQ ID NO 32
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 32
cggaggggcc atccac                                                16

<210> SEQ ID NO 33
<211> LENGTH: 15
<212> TYPE: DNA
<213> ORGANISM: Artificial
<220> FEATURE:
<223> OTHER INFORMATION: synthetic oligonucleotide probe

<400> SEQUENCE: 33
tggagagccc cgcgg                                                 15

<210> SEQ ID NO 34
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 34
gcaggaggca ttgctgatga                                            20

<210> SEQ ID NO 35
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 35
gatgggattt ccattgatga catttttagg cataggaccc gtgtct               46

<210> SEQ ID NO 36
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 36
cccacttgat tttggaggga tttttaggca taggacccgt gtct                 44

<210> SEQ ID NO 37
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 37
ccagtggact ccacgacgta cttttaggc ataggaccog tgtct                 45

<210> SEQ ID NO 38
<211> LENGTH: 45
<212> TYPE: DNA
<213> ORGANISM: Artificial
```

```
<220> FEATURE:
<223> OTHER INFORMATION: synthetic oligonucleotide probe

<400> SEQUENCE: 38
ttctccatgg tggtgaagac gttttttaggc ataggacccg tgtct        45

<210> SEQ ID NO 39
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 39
tcttgaggct gttgtcatac ttctttttta ggcataggac ccgtgtct     48

<210> SEQ ID NO 40
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 40
gggtgctaag cagttggtgg ttttttaggc ataggacccg tgtct         45

<210> SEQ ID NO 41
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 41
ccttccacga taccaaagtt gttttttagg cataggaccc gtgtct        46

<210> SEQ ID NO 42
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 42
ggcatggact gtggtcatga gttttttagg cataggaccc gtgtct        46

<210> SEQ ID NO 43
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 43
agtcttctgg gtggcagtga ttttttaggc ataggacccg tgtct         45

<210> SEQ ID NO 44
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 44
ccatcacgcc acagtttcct ttttaggcat aggacccgtg tct           43
```

<210> SEQ ID NO 45
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 45
cagtagaggc agggatgatg ttcttttag gcataggacc cgtgtct        47

<210> SEQ ID NO 46
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 46
cacagccttg gcagcgcttt ttaggcatag gacccgtgtc t              41

<210> SEQ ID NO 47
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 47
ccagtgagct tcccgttcat ttttaggcat aggacccgtg tct            43

<210> SEQ ID NO 48
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 48
tgacggtgcc atggaatttt ttttaaaact atacgtgct                 39

<210> SEQ ID NO 49
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 49
agcttcccgt tctcagcctt ttttaaaact atacgtgct                 39

<210> SEQ ID NO 50
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 50
tctcgctcct ggaagatggt tttttaaaac tatacgtgct                40

<210> SEQ ID NO 51
<211> LENGTH: 37
<212> TYPE: DNA
<213> ORGANISM: Artificial
<220> FEATURE:
<223> OTHER INFORMATION: synthetic oligonucleotide probe

```
<400> SEQUENCE: 51
gcaaatgagc cccagccttt ttaaaactat acgtgct                              37

<210> SEQ ID NO 52
<211> LENGTH: 37
<212> TYPE: DNA
<213> ORGANISM: Artificial
<220> FEATURE:
<223> OTHER INFORMATION: synthetic oligonucleotide probe

<400> SEQUENCE: 52 cctttggct ccccccttt ttaaaactat acgtgct                               37

<210> SEQ ID NO 53
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 53
catggatgac cttggccagt ttttaaaact atacgtgct                            39

<210> SEQ ID NO 54
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 54
gctcagggat gaccttgcct ttttaaaact atacgtgct                            39

<210> SEQ ID NO 55
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 55
ttttttttag cacgtatagt ttt                                             23

<210> SEQ ID NO 56
<211> LENGTH: 28
<212> TYPE: DNA
<213> ORGANISM: Artificial
<220> FEATURE:
<223> OTHER INFORMATION: synthetic oligonucleotide probe

<400> SEQUENCE: 56
tgcattaaaa tatttcttaa ggttttct                                        28

<210> SEQ ID NO 57
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 57
aaatgcctaa gaaaagagtt cca                                             23

<210> SEQ ID NO 58
```

```
<211> LENGTH: 27
<212> TYPE: DNA
<213> ORGANISM: Artificial
<220> FEATURE:
<223> OTHER INFORMATION: synthetic oligonucleotide probe

<400> SEQUENCE: 58
aaaaagtttg aagtaaaagg agacaat                                          27

<210> SEQ ID NO 59
<211> LENGTH: 27
<212> TYPE: DNA
<213> ORGANISM: Artificial
<220> FEATURE:
<223> OTHER INFORMATION: synthetic oligonucleotide probe

<400> SEQUENCE: 59
gatgctctgg tcatctttaa agttttt                                          27

<210> SEQ ID NO 60
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 60
ggatgctctt cgaccttgaa ac                                               22

<210> SEQ ID NO 61
<211> LENGTH: 33
<212> TYPE: DNA
<213> ORGANISM: Artificial
<220> FEATURE:
<223> OTHER INFORMATION: synthetic oligonucleotide probe

<400> SEQUENCE: 61
aataaataga tttagattta aaattcaaat att                                   33

<210> SEQ ID NO 62
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 62
gcttctttta catatgggtc ctggttttta ggcataggac ccgtgtct                   48

<210> SEQ ID NO 63
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 63
ttatccgcta catctgaatg acctttttag gcataggacc cgtgtct                    47

<210> SEQ ID NO 64
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 64
```
ttgatggtct ccacactctt ttgtttttag gcataggacc cgtgtct       47

<210> SEQ ID NO 65
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 65
aaaaacttga cattcatgtc ttccttttta ggcataggac ccgtgtct      48

<210> SEQ ID NO 66
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 66
ataattagtc agcttttcga agtcattttt aggcatagga cccgtgtct     49

<210> SEQ ID NO 67
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 67
tggacattca agtcagttac cgattttag gcataggacc cgtgtct        47

<210> SEQ ID NO 68
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 68
cgacagttca gccatcactt ggtttttagg cataggaccc gtgtct        46

<210> SEQ ID NO 69
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 69
agcatctgac tcctttttcg cttttaggc ataggaccg tgtct           45

<210> SEQ ID NO 70
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 70
gcaggcagga caaccattac tgtttttagg cataggaccc gtgtct        46

<210> SEQ ID NO 71
<211> LENGTH: 54
<212> TYPE: DNA

<213> ORGANISM: Artificial
<220> FEATURE:
<223> OTHER INFORMATION: synthetic oligonucleotide probe

<400> SEQUENCE: 71
aatacttatt tgattgatga gtctaaaaat tttttaggca taggacccgt gtct    54

<210> SEQ ID NO 72
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 72
cactctcctc tttccaattc ttcatttttt tttcacacac attaac    46

<210> SEQ ID NO 73
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 73
ttggctctgc attattttc tgttttttt cacacacatt aac    43

<210> SEQ ID NO 74
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 74
tctcgtttct ttttgttgct attgttttt tcacacacat taac    44

<210> SEQ ID NO 75
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 75
atgagttcat gtattgcttt gcgttttttt tcacacacat taac    44

<210> SEQ ID NO 76
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 76
ttccctgttt tagctgctgg ttttttcac acacattaac    40

<210> SEQ ID NO 77
<211> LENGTH: 50
<212> TYPE: DNA
<213> ORGANISM: Artificial
<220> FEATURE:
<223> OTHER INFORMATION: synthetic oligonucleotide probe

<400> SEQUENCE: 77
atattcccca tataaataat gttaaatatt ttttttcac acacattaac    50

<210> SEQ ID NO 78
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 78 tttttttttgt taatgtgtgt gaa                                          23

<210> SEQ ID NO 79
<211> LENGTH: 25
<212> TYPE: DNA
<213> ORGANISM: Artificial
<220> FEATURE:
<223> OTHER INFORMATION: synthetic oligonucleotide probe

<400> SEQUENCE: 79
ggtaaaactg gatcatctca gacaa                                         25

<210> SEQ ID NO 80
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 80
ggggcatcac ctcctcca                                                 18

<210> SEQ ID NO 81
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 81
gttcacatgc gccttgatgt                                               20

<210> SEQ ID NO 82
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 82
gctcttgttt tcacagggaa ga                                            22

<210> SEQ ID NO 83
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 83
ggctttgtag atgcctttct ct                                            22

<210> SEQ ID NO 84
<211> LENGTH: 17
<212> TYPE: DNA
<213> ORGANISM: Artificial
<220> FEATURE:

<223> OTHER INFORMATION: synthetic oligonucleotide probe

<400> SEQUENCE: 84
gactgggtgc cctggcc                                                  17

<210> SEQ ID NO 85
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 85
taggcaggtt gcctgggatt tttaggcata ggacccgtgt ct                       42

<210> SEQ ID NO 86
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 86
gtcttcactc tgctgaaggc attttttagg cataggaccc gtgtct                   46

<210> SEQ ID NO 87
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 87
actcctttaa caacaagttg tccattttta ggcataggac ccgtgtct                 48

<210> SEQ ID NO 88
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 88
ccttaaagtc ctccagcaag gttttaggc ataggacccg tgtct                     45

<210> SEQ ID NO 89
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 89
ggcttggcaa cccaggtaac tttttaggca taggacccgt gtct                     44

<210> SEQ ID NO 90
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 90
caggttctcc cccagggatt tttaggcata ggacccgtgt ct                       42

```
<210> SEQ ID NO 91
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 91
aatcgatgac agcgccgtat ttttaggcat aggacccgtg tct                    43

<210> SEQ ID NO 92
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 92
cacctgctcc acggccttttt tttaggcata ggacccgtgt ct                    42

<210> SEQ ID NO 93
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 93
tggagcttat taaaggcatt ctttttttag gcataggacc cgtgtct                47

<210> SEQ ID NO 94
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 94
tgatgaagat gtcaaactca ctcatttttt aggcatagga cccgtgtct              49

<210> SEQ ID NO 95
<211> LENGTH: 50
<212> TYPE: DNA
<213> ORGANISM: Artificial
<220> FEATURE:
<223> OTHER INFORMATION: synthetic oligonucleotide probe

<400> SEQUENCE: 95
cattgtcatg taggcttcta tgtagttttt taggcatagg acccgtgtct             50

<210> SEQ ID NO 96
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 96
ccctgatgtc tcagtttcgt atctttttttt aggcatagga cccgtgtct             49

<210> SEQ ID NO 97
<211> LENGTH: 49
<212> TYPE: DNA
<213> ORGANISM: Artificial
<220> FEATURE:
<223> OTHER INFORMATION: synthetic oligonucleotide probe
```

<400> SEQUENCE: 97
tgtcctagag tctatagagt cgccattttt aggcatagga cccgtgtct      49

<210> SEQ ID NO 98
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 98
gctatcccag agccccagat tttttaggca taggacccgt gtct            44

<210> SEQ ID NO 99
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 99
agtgggtgca gctgttctca tttttccgtg cttttctaat                 40

<210> SEQ ID NO 100
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 100
ctcggagatc tcgaagcatg tttttccgt gcttttctaa t                41

<210> SEQ ID NO 101
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 101
gctgatcctt catttgaaag aaattttttcc gtgcttttct aat            43

<210> SEQ ID NO 102
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 102
ctgggtcttg gttctcagct tttttccgt gcttttctaa t                41

<210> SEQ ID NO 103
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 103
gcctcagcct gagggtcttt ttttccgtgc ttttctaat                  39

<210> SEQ ID NO 104
<211> LENGTH: 44

```
<212> TYPE: DNA
<213> ORGANISM: Artificial
<220> FEATURE:
<223> OTHER INFORMATION: synthetic oligonucleotide probe

<400> SEQUENCE: 104
ccgattttgg agacctctaa tttatttttc cgtgcttttc taat                44

<210> SEQ ID NO 105
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 105 tttttttat tagaaaagca cgg                                        23

<210> SEQ ID NO 106
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 106
actgacgcgg cctgcc                                               16

<210> SEQ ID NO 107
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 107
ccagacatca ccaagctttt tt                                        22

<210> SEQ ID NO 108
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 108
gccatcagct tcaaagaaca agttttagg cataggaccc gtgtct              46

<210> SEQ ID NO 109
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 109
aaggagcact tcatctgttt aggttttag gcataggacc cgtgtct             47

<210> SEQ ID NO 110
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 110
```

```
atgccgccat ccagaggttt ttaggcatag gacccgtgtc t              41
```

<210> SEQ ID NO 111
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 111

```
ggtcggagat tcgtagctgg ttttaggca taggacccgt gtct            44
```

<210> SEQ ID NO 112
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 112

```
gcttgtccat ggccacaaca ttttaggca taggacccgt gtct             44
```

<210> SEQ ID NO 113
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 113

```
gggaaccagc atcttcctca ttttaggca taggacccgt gtct             44
```

<210> SEQ ID NO 114
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 114

```
ggttcttctt caaagatgaa gggttttag gcataggacc cgtgtct          47
```

<210> SEQ ID NO 115
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 115

```
ttatcccatg tgtcgaagaa gatatttta ggcataggac ccgtgtct         48
```

<210> SEQ ID NO 116
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 116

```
catcgtgcac ataagcctcg ttttaggca taggacccgt gtct             44
```

<210> SEQ ID NO 117
<211> LENGTH: 47
<212> TYPE: DNA
<213> ORGANISM: Artificial

```
<220> FEATURE:
<223> OTHER INFORMATION: synthetic oligonucleotide probe

<400> SEQUENCE: 117
gcagttcagt gatcgtacag gtgtttttag gcataggacc cgtgtct            47

<210> SEQ ID NO 118
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 118
gctgtgagtc ccggagcgtt ttttaggcat aggacccgtg tct                43

<210> SEQ ID NO 119
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 119
atggagaaca ccacttgttg cttttttagg cataggaccc gtgtct             46

<210> SEQ ID NO 120
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 120
actttcttct ccttgtacaa aggactttt aggcatagga cccgtgtct            49

<210> SEQ ID NO 121
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 121
aggccacagg tattttgtca ttttttttagg cataggaccc gtgtct            46

<210> SEQ ID NO 122
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 122
gcagaggtcc aggtcctggt ttttaacgtg tattccatt                     39

<210> SEQ ID NO 123
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 123
tgaagccctt gctgtagtgg ttttttaacg tgtattccat t                  41
```

<210> SEQ ID NO 124
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 124
cctggaaggt ctgtgggcat ttttaacgtg tattccatt        39

<210> SEQ ID NO 125
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 125
aaagaaggtg ctcaggtcat tcttttttaa cgtgtattcc att        43

<210> SEQ ID NO 126
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 126
ggagagcttt cagttcatat ggatttttaa cgtgtattcc att        43

<210> SEQ ID NO 127
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 127
ccatatcctg tccctggagg tttttaacg tgtattccat t        41

<210> SEQ ID NO 128
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 128 attctttttcc ttgaggccca tttttaacgt gtattccatt        40

<210> SEQ ID NO 129
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 129
ttttttttaa tggaatacac gtt        23

<210> SEQ ID NO 130
<211> LENGTH: 25
<212> TYPE: DNA
<213> ORGANISM: Artificial
<220> FEATURE:
<223> OTHER INFORMATION: synthetic oligonucleotide probe

```
<400> SEQUENCE: 130
ttccattcaa aatcatctgt aaatc                                           25

<210> SEQ ID NO 131
<211> LENGTH: 24
<212> TYPE: DNA
<213> ORGANISM: Artificial
<220> FEATURE:
<223> OTHER INFORMATION: synthetic oligonucleotide probe

<400> SEQUENCE: 131
cctgggtctt aagtgaaagt tttt                                            24

<210> SEQ ID NO 132
<211> LENGTH: 25
<212> TYPE: DNA
<213> ORGANISM: Artificial
<220> FEATURE:
<223> OTHER INFORMATION: synthetic oligonucleotide probe

<400> SEQUENCE: 132
agcatattca cacatgaatg ttgtt                                           25

<210> SEQ ID NO 133
<211> LENGTH: 25
<212> TYPE: DNA
<213> ORGANISM: Artificial
<220> FEATURE:
<223> OTHER INFORMATION: synthetic oligonucleotide probe

<400> SEQUENCE: 133
aaaaggtaat ccatctgttc agaaa                                           25

<210> SEQ ID NO 134
<211> LENGTH: 32
<212> TYPE: DNA
<213> ORGANISM: Artificial
<220> FEATURE:
<223> OTHER INFORMATION: synthetic oligonucleotide probe

<400> SEQUENCE: 134
attcaacaat aaatataaaa tttaaatatt ta                                   32

<210> SEQ ID NO 135
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 135
agtaggtgca ctgtttgtga caagttttta ggcataggac ccgtgtct                  48

<210> SEQ ID NO 136
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 136
gctgtgtttt ctttgtagaa cttgattttt aggcatagga cccgtgtct                 49

<210> SEQ ID NO 137
```

```
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 137
cagcagtaaa tgctccagtt gtattttag gcataggacc cgtgtct                47

<210> SEQ ID NO 138
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 138
aaacttaaat gtgagcatcc tggtttttag gcataggacc cgtgtct                47

<210> SEQ ID NO 139
<211> LENGTH: 50
<212> TYPE: DNA
<213> ORGANISM: Artificial
<220> FEATURE:
<223> OTHER INFORMATION: synthetic oligonucleotide probe

<400> SEQUENCE: 139
tagacactga agatgtttca gttctgtttt taggcatagg acccgtgtct             50

<210> SEQ ID NO 140
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 140
gctttgagct aaatttagca cttcttttta ggcataggac ccgtgtct               48

<210> SEQ ID NO 141
<211> LENGTH: 50
<212> TYPE: DNA
<213> ORGANISM: Artificial
<220> FEATURE:
<223> OTHER INFORMATION: synthetic oligonucleotide probe

<400> SEQUENCE: 141
attacgttga tattgctgat taagtctttt taggcatagg acccgtgtct             50

<210> SEQ ID NO 142
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 142
ttctacaatg gttgctgtct catcttttta ggcataggac ccgtgtct               48

<210> SEQ ID NO 143
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 143
```
tcagtgttga gatgatgctt tgactttta ggcataggac ccgtgtct        48

<210> SEQ ID NO 144
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 144
agtgggaagc acttaattat caagttttta ggcataggac ccgtgtct        48

<210> SEQ ID NO 145
<211> LENGTH: 52
<212> TYPE: DNA
<213> ORGANISM: Artificial
<220> FEATURE:
<223> OTHER INFORMATION: synthetic oligonucleotide probe

<400> SEQUENCE: 145
aatagttaca ataggtagca aaccatactt tttaggcata ggacccgtgt ct        52

<210> SEQ ID NO 146
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 146
tgagtttggg attcttgtaa ttattaattt ttgaagttac cgttttc        47

<210> SEQ ID NO 147
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 147
tggccttctt gggcatgtat ttttgaagtt accgttttc        39

<210> SEQ ID NO 148
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 148
ctccagaggt ttgagttctt cttctttttg aagttaccgt tttc        44

<210> SEQ ID NO 149
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 149
tcagatccct ttagttccag aactttttg aagttaccgt tttc        44

<210> SEQ ID NO 150
<211> LENGTH: 47
<212> TYPE: DNA

<213> ORGANISM: Artificial
<220> FEATURE:
<223> OTHER INFORMATION: synthetic oligonucleotide probe

<400> SEQUENCE: 150
aataaataga aggcctgata tgttttattt ttgaagttac cgttttc     47

<210> SEQ ID NO 151
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 151 tttttttga aacggtaac ttc     23

<210> SEQ ID NO 152
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 152
tggggcaggg aaggca     16

<210> SEQ ID NO 153
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 153
ggaatcttct cctgggggta c     21

<210> SEQ ID NO 154
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 154
tggggcggct acatcttt     18

<210> SEQ ID NO 155
<211> LENGTH: 27
<212> TYPE: DNA
<213> ORGANISM: Artificial
<220> FEATURE:
<223> OTHER INFORMATION: synthetic oligonucleotide probe

<400> SEQUENCE: 155
gctttcacac atgttactct tgttaca     27

<210> SEQ ID NO 156
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 156
tttggaaggt tcaggttgtt tt     22

```
<210> SEQ ID NO 157
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 157
cctcaaactc caaaagacca gtg                                              23

<210> SEQ ID NO 158
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 158
ttgggtcagg ggtggttatt                                                  20

<210> SEQ ID NO 159
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 159
ctgcaggaac tccttaaagc tg                                               22

<210> SEQ ID NO 160
<211> LENGTH: 24
<212> TYPE: DNA
<213> ORGANISM: Artificial
<220> FEATURE:
<223> OTHER INFORMATION: synthetic oligonucleotide probe

<400> SEQUENCE: 160
cccattaaca acaacaatct gagg                                             24

<210> SEQ ID NO 161
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 161
ggctcctgga ggcgagatat ttttaggcat aggacccgtg tct                        43

<210> SEQ ID NO 162
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 162
aactggaccg aaggcgcttt tttaggcata ggacccgtgt ct                         42

<210> SEQ ID NO 163
<211> LENGTH: 42
<212> TYPE: DNA
<213> ORGANISM: Artificial
<220> FEATURE:
```

<223> OTHER INFORMATION: synthetic oligonucleotide probe

<400> SEQUENCE: 163
gcaggcaaca ccaggagctt tttaggcata ggacccgtgt ct                    42

<210> SEQ ID NO 164
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 164
aagaggtgag tggctgtctg tgtttttagg cataggaccc gtgtct                46

<210> SEQ ID NO 165
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 165
gaatttgttt gtcaattcgt tctgttttta ggcataggac ccgtgtct              48

<210> SEQ ID NO 166
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 166
gatgccgtcg aggatgtacc tttttaggca taggacccgt gtct                  44

<210> SEQ ID NO 167
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 167
ctgccagtgc ctctttgctt ttttaggcat aggacccgtg tct                   43

<210> SEQ ID NO 168
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 168
gcatccatct ttttcagcca tcttttagg cataggaccc gtgtct                 46

<210> SEQ ID NO 169
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 169
atgattttca ccaggcaagt ctttttagg cataggaccc gtgtct                 46

<210> SEQ ID NO 170
<211> LENGTH: 51
<212> TYPE: DNA
<213> ORGANISM: Artificial
<220> FEATURE:
<223> OTHER INFORMATION: synthetic oligonucleotide probe

<400> SEQUENCE: 170
atctgttctg gaggtactct aggtatattt ttaggcatag gacccgtgtc t                51

<210> SEQ ID NO 171
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 171
ggcttgttcc tcactactct caatttttag gcataggacc cgtgtct                      47

<210> SEQ ID NO 172
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 172
ttttgtactc atctgcacag ctcttttta ggcataggac ccgtgtct                      48

<210> SEQ ID NO 173
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 173
ctgcaggaac tggatcagga cttttaggc ataggacccg tgtct                         45

<210> SEQ ID NO 174
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 174
gcatctagat tctttgcctt ttttttttag gcataggacc cgtgtct                      47

<210> SEQ ID NO 175
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 175
gcaggctggc atttgtggtt tttaggcata ggacccgtgt ct                           42

<210> SEQ ID NO 176
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 176
tgtgcctgca gcttcgtcat ttttaggcat aggacccgtg tct         43

<210> SEQ ID NO 177
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 177
tgtcctgcag ccactggttc tttttaggca taggacccgt gtct        44

<210> SEQ ID NO 178
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 178
cgcagaatga gatgagttgt cattttttagg cataggaccc gtgtct     46

<210> SEQ ID NO 179
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 179
tgcccatgct acatttgcct ttttaggcat aggacccgtg tct         43

<210> SEQ ID NO 180
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 180
ggtttctgac cagaagaagg aatgtttttta ggcataggac ccgtgtct   48

<210> SEQ ID NO 181
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 181
aagttctgtg cccagtggac attttttaggc ataggacccg tgtct      45

<210> SEQ ID NO 182
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 182
gagcttctct ttcgttcccg tttttgggga acatagaaaa            40

<210> SEQ ID NO 183
<211> LENGTH: 43

```
<212> TYPE: DNA
<213> ORGANISM: Artificial
<220> FEATURE:
<223> OTHER INFORMATION: synthetic oligonucleotide probe

<400> SEQUENCE: 183
tgtggagaag gagttcatag ctgttttttgg ggaacataga aaa                 43

<210> SEQ ID NO 184
<211> LENGTH: 37
<212> TYPE: DNA
<213> ORGANISM: Artificial
<220> FEATURE:
<223> OTHER INFORMATION: synthetic oligonucleotide probe

<400> SEQUENCE: 184
agccccaggg agaaggcttt ttggggaaca tagaaaa                         37

<210> SEQ ID NO 185
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 185
tgtctccttt ctcagggctg attttttgggg aacatagaaa a                   41

<210> SEQ ID NO 186
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 186
cctcattgaa tccagattgg aattttttggg gaacatagaa aa                  42

<210> SEQ ID NO 187
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 187
gaagagccct caggctggat ttttgggaa catagaaaa                        39

<210> SEQ ID NO 188
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 188
tttttttttt ttctatgttc ccc                                        23

<210> SEQ ID NO 189
<211> LENGTH: 22
<212> TYPE: DNA
<213> ORGANISM: Artificial
<220> FEATURE:
<223> OTHER INFORMATION: synthetic oligonucleotide probe

<400> SEQUENCE: 189
```

```
caaaaacttc tccacaaccc tc                                              22

<210> SEQ ID NO 190
<211> LENGTH: 26
<212> TYPE: DNA
<213> ORGANISM: Artificial
<220> FEATURE:
<223> OTHER INFORMATION: synthetic oligonucleotide probe

<400> SEQUENCE: 190
agtgttgaag tagatttgct tgaagt                                          26

<210> SEQ ID NO 191
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 191
caacagaccc acacaataca tga                                             23

<210> SEQ ID NO 192
<211> LENGTH: 29
<212> TYPE: DNA
<213> ORGANISM: Artificial
<220> FEATURE:
<223> OTHER INFORMATION: synthetic oligonucleotide probe

<400> SEQUENCE: 192
gtacaatgaa aaactattca ttgtttact                                       29

<210> SEQ ID NO 193
<211> LENGTH: 31
<212> TYPE: DNA
<213> ORGANISM: Artificial
<220> FEATURE:
<223> OTHER INFORMATION: synthetic oligonucleotide probe

<400> SEQUENCE: 193 tttttttgtag attcaaataa ataatacttt a                                   31

<210> SEQ ID NO 194
<211> LENGTH: 29
<212> TYPE: DNA
<213> ORGANISM: Artificial
<220> FEATURE:
<223> OTHER INFORMATION: synthetic oligonucleotide probe

<400> SEQUENCE: 194
aaatccttat atttaaaaat tatttgttg                                       29

<210> SEQ ID NO 195
<211> LENGTH: 26
<212> TYPE: DNA
<213> ORGANISM: Artificial
<220> FEATURE:
<223> OTHER INFORMATION: synthetic oligonucleotide probe

<400> SEQUENCE: 195
gcttcaaata tcacattcta gcaaac                                          26

<210> SEQ ID NO 196
<211> LENGTH: 22
<212> TYPE: DNA
<213> ORGANISM: Artificial
```

```
<220> FEATURE:
<223> OTHER INFORMATION: synthetic oligonucleotide probe

<400> SEQUENCE: 196
aaaaaatcca ggatttccag ct                                          22

<210> SEQ ID NO 197
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 197
ctagggttgc cagatttaac aga                                         23

<210> SEQ ID NO 198
<211> LENGTH: 25
<212> TYPE: DNA
<213> ORGANISM: Artificial
<220> FEATURE:
<223> OTHER INFORMATION: synthetic oligonucleotide probe

<400> SEQUENCE: 198
ccacttagaa ataaaggaga aacca                                       25

<210> SEQ ID NO 199
<211> LENGTH: 24
<212> TYPE: DNA
<213> ORGANISM: Artificial
<220> FEATURE:
<223> OTHER INFORMATION: synthetic oligonucleotide probe

<400> SEQUENCE: 199
catgtcctca caacatcact gtga                                        24

<210> SEQ ID NO 200
<211> LENGTH: 24
<212> TYPE: DNA
<213> ORGANISM: Artificial
<220> FEATURE:
<223> OTHER INFORMATION: synthetic oligonucleotide probe

<400> SEQUENCE: 200
atgaaaaaac ttaaagtgct tcca                                        24

<210> SEQ ID NO 201
<211> LENGTH: 30
<212> TYPE: DNA
<213> ORGANISM: Artificial
<220> FEATURE:
<223> OTHER INFORMATION: synthetic oligonucleotide probe

<400> SEQUENCE: 201
aagttacact tgaaataat ttatgttatg                                   30

<210> SEQ ID NO 202
<211> LENGTH: 33
<212> TYPE: DNA
<213> ORGANISM: Artificial
<220> FEATURE:
<223> OTHER INFORMATION: synthetic oligonucleotide probe

<400> SEQUENCE: 202 ttaaataat acataaataa taaataggtt aat                               33
```

<210> SEQ ID NO 203
<211> LENGTH: 31
<212> TYPE: DNA
<213> ORGANISM: Artificial
<220> FEATURE:
<223> OTHER INFORMATION: synthetic oligonucleotide probe

<400> SEQUENCE: 203
ataaaacatc atttaatatc taaaataaaa t                               31

<210> SEQ ID NO 204
<211> LENGTH: 26
<212> TYPE: DNA
<213> ORGANISM: Artificial
<220> FEATURE:
<223> OTHER INFORMATION: synthetic oligonucleotide probe

<400> SEQUENCE: 204 taaaaccct gattgaaatt tatcta                                      26

<210> SEQ ID NO 205
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 205
ggtccagaca gagctctctt cctttttagg cataggaccc gtgtct               46

<210> SEQ ID NO 206
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 206
ttggatacca cagagaatga attttttta ggcataggac ccgtgtct               48

<210> SEQ ID NO 207
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 207
ttcactggca tcttcactga ttcttttag gcataggacc cgtgtct                47

<210> SEQ ID NO 208
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 208
tgtattgcat ctggcaaccc tattttagg cataggaccc gtgtct                 46

<210> SEQ ID NO 209
<211> LENGTH: 49
<212> TYPE: DNA
<213> ORGANISM: Artificial
<220> FEATURE:
<223> OTHER INFORMATION: synthetic oligonucleotide probe

```
<400> SEQUENCE: 209
gaaattcaaa tttaaccagg aatctttttt aggcatagga cccgtgtct               49

<210> SEQ ID NO 210
<211> LENGTH: 52
<212> TYPE: DNA
<213> ORGANISM: Artificial
<220> FEATURE:
<223> OTHER INFORMATION: synthetic oligonucleotide probe

<400> SEQUENCE: 210
catataagta tgttctggat atttcatgtt tttaggcata ggacccgtgt ct           52

<210> SEQ ID NO 211
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 211
ttctcccgtg caatatctag gattttttagg cataggaccc gtgtct                46

<210> SEQ ID NO 212
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 212
ggcctcaatt ttgctatttg tatatttta ggcataggac ccgtgtct                48

<210> SEQ ID NO 213
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 213
ccattcaatt cctgaaatta aagttttttt aggcatagga cccgtgtct              49

<210> SEQ ID NO 214
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 214
attgtcccat cattttatg tgatttttta ggcataggac ccgtgtct                48

<210> SEQ ID NO 215
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 215
aaatttgact ttatggcaaa attttttta ggcataggac ccgtgtct                48

<210> SEQ ID NO 216
```

```
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 216
aggcacagtg gaacaaggac tttttttaggc ataggacccg tgtct            45

<210> SEQ ID NO 217
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 217
ggtaagatgg tggctaatac tttttttttt aggcatagga cccgtgtct          49

<210> SEQ ID NO 218
<211> LENGTH: 48
<212> TYPE: DNA
<213> ORGANISM: Artificial
<220> FEATURE:
<223> OTHER INFORMATION: synthetic oligonucleotide probe

<400> SEQUENCE: 218
aattcttgca caaatatttg atgcttttta ggcataggac ccgtgtct            48

<210> SEQ ID NO 219
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 219
caatgattca tcttctattt ttccattttt aggcatagga cccgtgtct           49

<210> SEQ ID NO 220
<211> LENGTH: 57
<212> TYPE: DNA
<213> ORGANISM: Artificial
<220> FEATURE:
<223> OTHER INFORMATION: synthetic oligonucleotide probe

<400> SEQUENCE: 220
aaatttacta taacatcttt ataactattc aatttttag gcataggacc cgtgtct   57

<210> SEQ ID NO 221
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 221
tgcacccagt tttccttggt tttttttcaaa tgttagcct                     39

<210> SEQ ID NO 222
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 222
```

```
tttatgaat tctcagccct cttttttttt caaatgttag cct        43
```

<210> SEQ ID NO 223
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 223

```
cggatattct cttggccctt tttttttcaa atgttagcct           40
```

<210> SEQ ID NO 224
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 224

```
tgtggatcct ggctagcaga tttttttcaa atgttagcct           40
```

<210> SEQ ID NO 225
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 225

```
acccaattgt ttgtttgttt aatctttttt tcaaatgtta gcct      44
```

<210> SEQ ID NO 226
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 226

```
tttttttag gctaacattt gaa                              23
```

<210> SEQ ID NO 227
<211> LENGTH: 15
<212> TYPE: DNA
<213> ORGANISM: Artificial
<220> FEATURE:
<223> OTHER INFORMATION: synthetic oligonucleotide probe

<400> SEQUENCE: 227

```
ccctctgggg gccga                                      15
```

<210> SEQ ID NO 228
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 228

```
gaggtccctg gggaactctt                                 20
```

<210> SEQ ID NO 229
<211> LENGTH: 21
<212> TYPE: DNA

-continued

```
<213> ORGANISM: Artificial
<220> FEATURE:
<223> OTHER INFORMATION: synthetic oligonucleotide probe

<400> SEQUENCE: 229
ggccagaggg ctgattagag a                                               21

<210> SEQ ID NO 230
<211> LENGTH: 19
<212> TYPE: DNA
<213> ORGANISM: Artificial
<220> FEATURE:
<223> OTHER INFORMATION: synthetic oligonucleotide probe

<400> SEQUENCE: 230
aggcttgtca ctcggggtt                                                  19

<210> SEQ ID NO 231
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 231
tgaagaggac ctgggagtag atg                                             23

<210> SEQ ID NO 232
<211> LENGTH: 16
<212> TYPE: DNA
<213> ORGANISM: Artificial
<220> FEATURE:
<223> OTHER INFORMATION: synthetic oligonucleotide probe

<400> SEQUENCE: 232
gggcagcctt ggccct                                                     16

<210> SEQ ID NO 233
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 233
tggcaggggc tcttgatg                                                   18

<210> SEQ ID NO 234
<211> LENGTH: 19
<212> TYPE: DNA
<213> ORGANISM: Artificial
<220> FEATURE:
<223> OTHER INFORMATION: synthetic oligonucleotide probe

<400> SEQUENCE: 234
cccctctggg gtctccctc                                                  19

<210> SEQ ID NO 235
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 235
gtttgggaag gttggatgtt c                                               21
```

<210> SEQ ID NO 236
<211> LENGTH: 15
<212> TYPE: DNA
<213> ORGANISM: Artificial
<220> FEATURE:
<223> OTHER INFORMATION: synthetic oligonucleotide probe

<400> SEQUENCE: 236
tggggcaggg gaggc                                                        15

<210> SEQ ID NO 237
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 237 aggaggggt aataaaggga t                                                  21

<210> SEQ ID NO 238
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 238
tcactccaaa gtgcagcagg tttttaggca taggacccgt gtct                        44

<210> SEQ ID NO 239
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 239
ggtttgctac aacatgggct acttttagg cataggaccc gtgtct                       46

<210> SEQ ID NO 240
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 240
ggcggttcag ccactggatt tttaggcata ggacccgtgt ct                          42

<210> SEQ ID NO 241
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 241
caggagggca ttggcccttt ttaggcatag gacccgtgtc t                           41

<210> SEQ ID NO 242
<211> LENGTH: 41
<212> TYPE: DNA
<213> ORGANISM: Artificial
<220> FEATURE:

<223> OTHER INFORMATION: synthetic oligonucleotide probe

<400> SEQUENCE: 242
agctccacgc cattggcttt ttaggcatag gacccgtgtc t           41

<210> SEQ ID NO 243
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 243
caccaccagc tggttatctc tcttttaggg cataggaccc gtgtct      46

<210> SEQ ID NO 244
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 244
aggtacaggc cctctgatgg tttttaggca taggacccgt gtct        44

<210> SEQ ID NO 245
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 245
tgaggagcac atgggtggag tttttaggca taggacccgt gtct        44

<210> SEQ ID NO 246
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 246
gcggctgatg gtgtgggttt taggcatag gacccgtgtc t            41

<210> SEQ ID NO 247
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 247
gcagagagga ggttgacctt gttttaggc ataggacccg tgtct        45

<210> SEQ ID NO 248
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 248
cagggcttgg cctcagcttt ttaggcatag gacccgtgtc t           41

```
<210> SEQ ID NO 249
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 249
tctccagctg gaagacccct ttttaggcat aggacccgtg tct          43

<210> SEQ ID NO 250
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 250
gcgctgagtc ggtcaccctt ttttaggcat aggacccgtg tct          43

<210> SEQ ID NO 251
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 251
agactcggca aagtcgagat agtttttagg cataggaccc gtgtct       46

<210> SEQ ID NO 252
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 252
atcccaaagt agacctgccc ttttaggca taggacccgt gtct          44

<210> SEQ ID NO 253
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 253
gtcctcctca cagggcaatg ttttaggca taggacccgt gtct          44

<210> SEQ ID NO 254
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 254
cagaagaggt tgagggtgtc tgattttag gcataggacc cgtgtct       47

<210> SEQ ID NO 255
<211> LENGTH: 44
<212> TYPE: DNA
<213> ORGANISM: Artificial
<220> FEATURE:
<223> OTHER INFORMATION: synthetic oligonucleotide probe
```

<400> SEQUENCE: 255
gcttgggttc cgaccctaag tttttaggca taggacccgt gtct                44

<210> SEQ ID NO 256
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 256
cgagaagatg atctgactgc ctgtttttct gagtcaaagc att                43

<210> SEQ ID NO 257
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 257
gctgcccctc agcttgagtt tttctgagtc aaagcatt                38

<210> SEQ ID NO 258
<211> LENGTH: 40
<212> TYPE: DNA
<213> ORGANISM: Artificial
<220> FEATURE:
<223> OTHER INFORMATION: synthetic oligonucleotide probe

<400> SEQUENCE: 258
gtctggtagg agacggcgat tttttctgag tcaaagcatt                40

<210> SEQ ID NO 259
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 259
tcccagatag atgggctcat acttttctg agtcaaagca tt                42

<210> SEQ ID NO 260
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 260
tcgggccgat tgatctcatt tttctgagtc aaagcatt                38

<210> SEQ ID NO 261
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 261
cccccaattc tcttttgag cttttctga gtcaaagcat t                41

<210> SEQ ID NO 262
<211> LENGTH: 23

```
<212> TYPE: DNA
<213> ORGANISM: Artificial
<220> FEATURE:
<223> OTHER INFORMATION: synthetic oligonucleotide probe

<400> SEQUENCE: 262 tttttttttaa tgctttgact cag                                              23

<210> SEQ ID NO 263
<211> LENGTH: 20
<212> TYPE: DNA
<213> ORGANISM: Artificial
<220> FEATURE:
<223> OTHER INFORMATION: synthetic oligonucleotide probe

<400> SEQUENCE: 263
catcaggggc acacaggatg                                                   20

<210> SEQ ID NO 264
<211> LENGTH: 15
<212> TYPE: DNA
<213> ORGANISM: Artificial
<220> FEATURE:
<223> OTHER INFORMATION: synthetic oligonucleotide probe

<400> SEQUENCE: 264 gcagccccccg catcg                                                       15

<210> SEQ ID NO 265
<211> LENGTH: 21
<212> TYPE: DNA
<213> ORGANISM: Artificial
<220> FEATURE:
<223> OTHER INFORMATION: synthetic oligonucleotide probe

<400> SEQUENCE: 265
ctcctcagtg ggcacacact c                                                 21

<210> SEQ ID NO 266
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 266
tggaggtaga gcagcaaggc tttttaggca taggacccgt gtct                        44

<210> SEQ ID NO 267
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 267
tgggaccact tggcatggtt tttaggcata ggacccgtgt ct                          42

<210> SEQ ID NO 268
<211> LENGTH: 45
<212> TYPE: DNA
<213> ORGANISM: Artificial
<220> FEATURE:
<223> OTHER INFORMATION: synthetic oligonucleotide probe

<400> SEQUENCE: 268
```
gatgattctg ccctcctcct tttttttaggc ataggacccg tgtct              45

<210> SEQ ID NO 269
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 269
tccatgaact tcaccacttc gttttttagg cataggaccc gtgtct             46

<210> SEQ ID NO 270
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 270
gcagtagctg cgctgataga cattttttagg cataggaccc gtgtct            46

<210> SEQ ID NO 271
<211> LENGTH: 44
<212> TYPE: DNA
<213> ORGANISM: Artificial
<220> FEATURE:
<223> OTHER INFORMATION: synthetic oligonucleotide probe

<400> SEQUENCE: 271
accagggtct cgattggatg tttttaggca taggacccgt gtct               44

<210> SEQ ID NO 272
<211> LENGTH: 46
<212> TYPE: DNA
<213> ORGANISM: Artificial
<220> FEATURE:
<223> OTHER INFORMATION: synthetic oligonucleotide probe

<400> SEQUENCE: 272
agggtactcc tggaagatgt cctttttagg cataggaccc gtgtct             46

<210> SEQ ID NO 273
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 273
gcttgaagat gtactcgatc tcatcttttt aggcatagga cccgtgtct          49

<210> SEQ ID NO 274
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 274
caggccctcg tcattgcatt tttaggcata ggacccgtgt ct                 42

<210> SEQ ID NO 275
<211> LENGTH: 46
<212> TYPE: DNA
<213> ORGANISM: Artificial

-continued

```
<220> FEATURE:
<223> OTHER INFORMATION: synthetic oligonucleotide probe

<400> SEQUENCE: 275
taatctgcat ggtgatgttg gatttttagg cataggaccc gtgtct                    46

<210> SEQ ID NO 276
<211> LENGTH: 47
<212> TYPE: DNA
<213> ORGANISM: Artificial
<220> FEATURE:
<223> OTHER INFORMATION: synthetic oligonucleotide probe

<400> SEQUENCE: 276
atttgttgtg ctgtaggaag ctcttttttag gcataggacc cgtgtct                  47

<210> SEQ ID NO 277
<211> LENGTH: 49
<212> TYPE: DNA
<213> ORGANISM: Artificial
<220> FEATURE:
<223> OTHER INFORMATION: synthetic oligonucleotide probe

<400> SEQUENCE: 277
ctgatttttt ttcttgtctt gctctttttt aggcatagga cccgtgtct                 49

<210> SEQ ID NO 278
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 278
ttgcgctttc gttttttgctt tttaggcata ggacccgtgt ct                       42

<210> SEQ ID NO 279
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 279
ggcccacagg gaacgctttt ttaggcatag gacccgtgtc t                         41

<210> SEQ ID NO 280
<211> LENGTH: 38
<212> TYPE: DNA
<213> ORGANISM: Artificial
<220> FEATURE:
<223> OTHER INFORMATION: synthetic oligonucleotide probe

<400> SEQUENCE: 280
aaggctccaa tgcacccatt tttctttgag ttcggttt                             38

<210> SEQ ID NO 281
<211> LENGTH: 37
<212> TYPE: DNA
<213> ORGANISM: Artificial
<220> FEATURE:
<223> OTHER INFORMATION: synthetic oligonucleotide probe

<400> SEQUENCE: 281
ctgccatggg tgcagccttt ttctttgagt tcggttt                              37
```

```
<210> SEQ ID NO 282
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 282
tggtgaggtt tgatccgcat ttttctttga gttcggttt                              39

<210> SEQ ID NO 283
<211> LENGTH: 41
<212> TYPE: DNA
<213> ORGANISM: Artificial
<220> FEATURE:
<223> OTHER INFORMATION: synthetic oligonucleotide probe

<400> SEQUENCE: 283
atctctccta tgtgctggcc ttttttcttt gagttcggtt t                           41

<210> SEQ ID NO 284
<211> LENGTH: 43
<212> TYPE: DNA
<213> ORGANISM: Artificial
<220> FEATURE:
<223> OTHER INFORMATION: synthetic oligonucleotide probe

<400> SEQUENCE: 284
atctttcttt ggtctgcatt cacttttct ttgagttcgg ttt                          43

<210> SEQ ID NO 285
<211> LENGTH: 39
<212> TYPE: DNA
<213> ORGANISM: Artificial
<220> FEATURE:
<223> OTHER INFORMATION: synthetic oligonucleotide probe

<400> SEQUENCE: 285
ccctttccct ttcctcgaat ttttctttga gttcggttt                              39

<210> SEQ ID NO 286
<211> LENGTH: 42
<212> TYPE: DNA
<213> ORGANISM: Artificial
<220> FEATURE:
<223> OTHER INFORMATION: synthetic oligonucleotide probe

<400> SEQUENCE: 286
ccaggactta taccgggatt tcttttcctt tgagttcggt tt                          42

<210> SEQ ID NO 287
<211> LENGTH: 23
<212> TYPE: DNA
<213> ORGANISM: Artificial
<220> FEATURE:
<223> OTHER INFORMATION: synthetic oligonucleotide probe

<400> SEQUENCE: 287
ttttttttaa accgaactca aag                                               23
```

MULTIPLEX BRANCHED-CHAIN DNA ASSAYS

CROSS-REFERENCE TO RELATED APPLICATIONS

This application is a continuation of U.S. patent application Ser. No. 12/804,904, filed Jul. 29, 2010, which issued on Apr. 23, 2013 as U.S. Pat. No. 8,426,578. U.S. patent application Ser. No. 12/804,904 is a continuation of U.S. patent application Ser. No. 11/433,081, filed May 11, 2006, entitled "MULTIPLEX BRANCHED-CHAIN DNA ASSAYS" by Luo and Yang, which issued on Sep. 28, 2010 as U.S. Pat. No. 7,803,541, and which claims priority to and benefit of the following prior provisional patent application: U.S. Ser. No. 60/680,976, filed May 12, 2005, entitled "MULTIPLEX BRANCHED-CHAIN DNA ASSAYS" by Luo and Yang; each of these applications is incorporated herein by reference in its entirety for all purposes.

FIELD OF THE INVENTION

The present invention is in the field of nucleic acid detection. The invention includes methods for detecting the presence of two or more nucleic acids simultaneously in a single sample. The invention also includes compositions and kits related to the methods.

BACKGROUND OF THE INVENTION

Global gene expression profiling and other technologies have identified a large number of genes whose expression is altered, e.g., in diseased tissues or in tissues and cells treated with pharmaceutical agents (Lockhart and Winzeler (2000) "Genomics, gene expression and DNA arrays" Nature 405: 827-36 and Gunther et al. (2003) "Prediction of clinical drug efficacy by classification of drug-induced genomic expression profiles in vitro" Proc Natl Acad Sci USA 100:9608-13). Such genes are being increasingly used as biomarkers in disease diagnosis, staging, and prognosis (Golub et al. (1999) "Molecular classification of cancer: class discovery and class prediction by gene expression monitoring" Science 286:531-7); target identification, validation and pathway analysis (Roberts et al. (2000) "Signaling and circuitry of multiple MAPK pathways revealed by a matrix of global gene expression profiles" Science 287:873-80); drug screening (Hamadeh et al. (2002) "Prediction of compound signature using high density gene expression profiling" Toxicol Sci 67:232-40); and studies of drug efficacy, structure-activity relationship, toxicity, and drug-target interactions (Gerhold et al. (2001) "Monitoring expression of genes involved in drug metabolism and toxicology using DNA microarrays" Physiol Genomics 5:161-70 and Thomas et al. (2001) "Identification of toxicologically predictive gene sets using cDNA microarrays" Mol Pharmacol 60:1189-94). As biomarkers are identified, their involvement in disease management and drug development will need to be evaluated in higher throughput and broader populations of samples. Simpler and more flexible expression profiling technology that allows the expression analysis of multiple genes with higher data quality and higher throughput is therefore needed.

Levels of RNA expression have traditionally been measured using Northern blot and nuclease protection assays. However, these approaches are time-consuming and have limited sensitivity, and the data generated are more qualitative than quantitative in nature. Greater sensitivity and quantification is possible with reverse transcription polymerase chain reaction (RT-PCR) based methods, such as quantitative real-time RT-PCR, but these approaches have low multiplex capabilities (Bustin (2002) "Quantification of mRNA using real-time reverse transcription PCR (RT-PCR): trends and problems" J Mol Endocrinol 29:23-39 and Bustin and Nolan (2004) "Pitfalls of quantitative real-time reverse-transcription polymerase chain reaction" J Biomol Tech. 15:155-66). Microarray technology has been widely used in discovery research, but its moderate sensitivity and its relatively long experimental procedure have limited its use in high throughput expression profiling applications (Epstein and Butow (2000) "Microarray technology—enhanced versatility, persistent challenge" Cuff Opin Biotechnol. 11:36-41).

Most of the current methods of mRNA quantification require RNA isolation, reverse transcription, and target amplification, each of which introduces variability that leads to low overall assay precision. Recently, a multiplex screening assay for mRNA quantification combining nuclease protection with luminescent array detection was reported (Martel et al. (2002) "Multiplexed screening assay for mRNA combining nuclease protection with luminescent array detection" Assay Drug Dev Technol. 1:61-71). Although this assay has the advantage of measuring mRNA transcripts directly from cell lysates, limited assay sensitivity and reproducibility were reported. Another multiplex mRNA assay without the need for RNA isolation was also reported (Tian et al. (2004) "Multiplex mRNA assay using electrophoretic tags for high-throughput gene expression analysis" Nucleic Acids Res. 32:e126). This assay couples the primary Invader® mRNA assay with small fluorescent molecule eTags that can be distinguished by capillary electrophoresis through distinct charge-to-mass ratios of eTags. However, this assay requires the use of a specially designed and synthesized set of eTagged signal probes, complicated capillary electrophoresis equipment, and a special data analysis package.

Among other aspects, the present invention provides methods that overcome the above noted limitations and permit rapid, simple, and sensitive detection of multiple mRNAs (and/or other nucleic acids) simultaneously. A complete understanding of the invention will be obtained upon review of the following.

SUMMARY OF THE INVENTION

In one aspect, the present invention provides methods of detecting two or more nucleic acids of interest in a multiplex branched-chain DNA assay. Different nucleic acids are captured through cooperative hybridization events on different, identifiable subsets of particles or at different selected positions on a spatially addressable solid support. Compositions and kits related to the methods are also provided.

A first general class of embodiments provides methods of detecting two or more nucleic acids of interest. In the methods, a sample, a pooled population of particles, and two or more subsets of n capture extenders, wherein n is at least two, are provided. The sample comprises or is suspected of comprising the nucleic acids of interest. The pooled population of particles includes two or more subsets of particles, and a plurality of the particles in each subset are distinguishable from a plurality of the particles in every other subset. The particles in each subset have associated therewith a different capture probe. Each subset of n capture extenders is capable of hybridizing to one of the nucleic acids of interest, and the capture extenders in each subset are capable of hybridizing to one of the capture probes and thereby associating each subset of n capture extenders with a selected subset of the particles. Each nucleic acid of interest can thus, by hybridizing to its corresponding subset of n capture extenders which are in turn hybridized to a corresponding capture probe, be associated with an identifiable subset of the particles.

The sample, the pooled population of particles, and the subsets of n capture extenders are contacted, any nucleic acid of interest present in the sample is hybridized to its corresponding subset of n capture extenders, and the subset of n capture extenders is hybridized to its corresponding capture probe. The hybridizing the nucleic acid of interest to the n capture extenders and the n capture extenders to the corresponding capture probe captures the nucleic acid on the subset of particles with which the capture extenders are associated. The hybridizing the subset of n capture extenders to the corresponding capture probe is performed at a hybridization temperature which is greater than a melting temperature $T_m$ of a complex between each individual capture extender and its corresponding capture probe.

To determine which subsets of particles have a nucleic acid of interest captured on the particles, one or more label extenders and a label probe system comprising a label are hybridized to any nucleic acid of interest captured on the particles, and at least a portion of the particles from each subset are identified and the presence or absence of the label is detected on those particles. Since a correlation exists between a particular subset of particles and a particular nucleic acid of interest, which subsets of particles have the label present indicates which of the nucleic acids of interest were present in the sample.

The methods are useful for multiplex detection of nucleic acids, optionally highly multiplex detection. Thus, the two or more nucleic acids of interest (i.e., the nucleic acids to be detected) optionally comprise five or more, 10 or more, 20 or more, 30 or more, 40 or more, 50 or more, or even 100 or more nucleic acids of interest. A like number of subsets of particles and subsets of capture extenders are provided; thus, the two or more subsets of particles can comprise five or more, 10 or more, 20 or more, 30 or more, 40 or more, 50 or more, or even 100 or more subsets of particles, while the two or more subsets of n capture extenders can comprise five or more, 10 or more, 20 or more, 30 or more, 40 or more, 50 or more, or even 100 or more subsets of n capture extenders.

In one class of embodiments, the particles are microspheres. The microspheres of each subset can be distinguishable from those of the other subsets, e.g., on the basis of their fluorescent emission spectrum, their diameter, or a combination thereof.

As noted, each of the two or more subsets of capture extenders includes n capture extenders, where n is at least two. Preferably, n is at least three, and n can be at least four or at least five or more. Typically, but not necessarily, n is at most ten. The n capture extenders in a subset preferably hybridize to nonoverlapping polynucleotide sequences in the corresponding nucleic acid of interest. The nonoverlapping polynucleotide sequences can, but need not be, consecutive within the nucleic acid of interest.

Each capture extender is capable of hybridizing to its corresponding capture probe. The capture extender typically includes a polynucleotide sequence C-1 that is complementary to a polynucleotide sequence C-2 in its corresponding capture probe. In one aspect, C-1 and C-2 are 20 nucleotides or less in length. In one class of embodiments, C-1 and C-2 are between 9 and 17 nucleotides in length (inclusive), preferably between 12 and 15 nucleotides (inclusive).

As noted, the hybridizing the subset of n capture extenders to the corresponding capture probe is performed at a hybridization temperature which is greater than a melting temperature $T_m$ of a complex between each individual capture extender and its corresponding capture probe. The hybridization temperature is typically about 5° C. or more greater than the $T_m$, e.g., about 7° C. or more, about 10° C. or more, about 12° C. or more, about 15° C. or more, about 17° C. or more, or even about 20° C. or more greater than the $T_m$.

In one class of embodiments, contacting the sample, the pooled population of particles, and the subsets of n capture extenders comprises combining the sample with the subsets of n capture extenders to form a mixture, and then combining the mixture with the pooled population of particles.

In a preferred class of embodiments, hybridizing one or more label extenders and a label probe system to any nucleic acid of interest captured on the particles comprises providing two or more subsets of one or more label extenders, wherein each subset of label extenders is capable of hybridizing to one of the nucleic acids of interest, hybridizing any nucleic acid of interest captured on the particles to its corresponding subset of label extenders, and hybridizing the label probe system to the label extenders. The two or more subsets of label extenders can include, e.g., five or more, 10 or more, 20 or more, 30 or more, 40 or more, 50 or more, or even 100 or more subsets of label extenders. The hybridizations can be performed simultaneously or sequentially, in essentially any order. In one embodiment, any nucleic acid of interest present in the sample is hybridized to its corresponding subset of label extenders and to its corresponding subset of n capture extenders, then the subset of n capture extenders is hybridized to its corresponding capture probe.

The label probe system optionally includes an amplification multimer and a plurality of label probes, wherein the amplification multimer is capable of hybridizing to a label extender and to a plurality of label probes. In one class of embodiments, the label probe comprises the label. In one aspect, the label is a fluorescent label, and detecting the presence of the label on the particles comprises detecting a fluorescent signal from the label.

The methods can optionally be used to quantitate the amounts of the nucleic acids of interest present in the sample. For example, in one class of embodiments, an intensity of a signal from the label is measured, e.g., for each subset of particles, and correlated with a quantity of the corresponding nucleic acid of interest present.

At any of various steps, materials not captured on the particles are optionally separated from the particles. For example, after the capture extenders, nucleic acids, label extenders, blocking probes, and particle-bound capture probes are hybridized, the particles are optionally washed to remove unbound nucleic acids and probes; after the label extenders and amplification multimer are hybridized, the particles are optionally washed to remove unbound amplification multimer; and/or after the label probes are hybridized to the amplification multimer, the particles are optionally washed to remove unbound label probe prior to detection of the label.

The methods can be used to detect the presence of the nucleic acids of interest in essentially any type of sample. For example, the sample can be derived from an animal, a human, a plant, a cultured cell, a virus, a bacterium, a pathogen, and/or a microorganism. The sample optionally includes a cell lysate, an intercellular fluid, a bodily fluid (including, but not limited to, blood, serum, saliva, urine, sputum, or spinal fluid), and/or a conditioned culture medium, and is optionally derived from a tissue (e.g., a tissue homogenate), a biopsy, and/or a tumor. Similarly, the nucleic acids can be essentially any desired nucleic acids. As just a few examples, the nucleic acids of interest can be derived from one or more of an animal, a human, a plant, a cultured cell, a microorganism, a virus, a bacterium, or a pathogen. In one class of embodiments, the two or more nucleic acids of interest comprise two or more mRNAs.

In one class of embodiments, at least one of the nucleic acids of interest is present in the sample in a non-zero amount of 200 amol or less, 150 amol or less, 100 amol or less, 50 amol or less, 10 amol or less, 1 amol or less, or even 0.1 amol or less. In one exemplary class of embodiments, the sample includes a first nucleic acid of interest, and at least 30%, at least 50%, at least 80%, at least 90%, at least 95%, or even at least 99% of a total amount of the first nucleic acid present in the sample is captured on a first subset of particles. Second, third, etc. nucleic acids can similarly be quantitatively captured. Such quantitative capture can occur without capture of a significant amount of undesired nucleic acids, even those of very similar sequence to the nucleic acid of interest.

Thus, in one class of embodiments, the sample comprises or is suspected of comprising a first nucleic acid of interest and a second nucleic acid which has a polynucleotide sequence which is 95% or more identical to that of the first nucleic acid (e.g., 96% or more, 97% or more, 98% or more, or even 99% or more identical). The first nucleic acid, if present in the sample, is captured on a first subset of particles, while the second nucleic acid comprises 1% or less of a total amount of nucleic acid captured on the first subset of particles (e.g., 0.5% or less, 0.2% or less, or even 0.1% or less).

As just one example of how closely related nucleic acids can be distinguished using the methods of the invention, different splice variants of a given mRNA can be distinguished. Thus, in one class of embodiments, the sample comprises a first nucleic acid of interest and a second nucleic acid, where the first nucleic acid is a first splice variant and the second nucleic acid is a second splice variant of the given mRNA. A first subset of n capture extenders is capable of hybridizing to the first splice variant, of which at most n−1 capture extenders are capable of hybridizing to the second splice variant. Preferably, hybridization of the n capture extenders to the first splice variant captures the first splice variant on a first subset of particles while hybridization of the at most n−1 capture extenders to the second splice variant does not capture the second splice variant on the first subset of particles.

Another general class of embodiments provides a composition for detecting two or more nucleic acids of interest that includes two or more subsets of particles, two or more subsets of n capture extenders, wherein n is at least two, two or more subsets of one or more label extenders, and a label probe system comprising a label. A plurality of the particles in each subset are distinguishable from a plurality of the particles in every other subset. The particles in each subset have associated therewith a different capture probe. Each subset of n capture extenders is capable of hybridizing to one of the nucleic acids of interest, and the capture extenders in each subset are capable of hybridizing to one of the capture probes and thereby associating each subset of n capture extenders with a selected subset of the particles. When the nucleic acid of interest corresponding to a subset of n capture extenders is present in the composition and is hybridized to the subset of n capture extenders, which are hybridized to the corresponding capture probe, the nucleic acid of interest is hybridized to the subset of n capture extenders at a hybridization temperature which is greater than a melting temperature $T_m$ of a complex between each individual capture extender and the capture probe.

Essentially all of the features noted for the embodiments above apply to these embodiments as well, as relevant; for example, with respect to number of capture extenders per subset, composition of the label probe system, type of label, inclusion of blocking probes, configuration of the capture extenders, capture probes, label extenders, and/or blocking probes, number of nucleic acids of interest and of subsets of particles, capture extenders and label extenders, source of the sample and/or nucleic acids, and/or the like.

A related general class of embodiments provides a composition comprising two or more subsets of particles, two or more subsets of n capture extenders, wherein n is at least two, two or more subsets of one or more label extenders, a label probe system comprising a label, and at least a first nucleic acid of interest. A plurality of the particles in each subset are distinguishable from a plurality of the particles in every other subset. The particles in each subset have associated therewith a different capture probe. Each subset of n capture extenders is capable of hybridizing to one of the nucleic acids of interest, and the capture extenders in each subset are capable of hybridizing to one of the capture probes and thereby associating each subset of n capture extenders with a selected subset of the particles. In this class of embodiments, the composition is maintained at a hybridization temperature, which hybridization temperature is greater than a melting temperature $T_m$ of a complex between each individual capture extender and its corresponding capture probe. The first nucleic acid of interest is hybridized to a first subset of n first capture extenders, which first capture extenders are hybridized to a first capture probe.

Essentially all of the features noted for the embodiments above apply to these embodiments as well, as relevant; for example, with respect to number of capture extenders per subset, composition of the label probe system, type of label, inclusion of blocking probes, configuration of the capture extenders, capture probes, label extenders, and/or blocking probes, number of nucleic acids of interest and of subsets of particles, capture extenders and label extenders, source of the sample and/or nucleic acids, and/or the like.

Yet another general class of embodiments provides a kit for detecting two or more nucleic acids of interest. The kit includes two or more subsets of particles, two or more subsets of n capture extenders, wherein n is at least two, two or more subsets of one or more label extenders, and a label probe system comprising a label, packaged in one or more containers. A plurality of the particles in each subset are distinguishable from a plurality of the particles in every other subset. The particles in each subset have associated therewith a different capture probe. Each subset of n capture extenders is capable of hybridizing to one of the nucleic acids of interest, and the capture extenders in each subset are capable of hybridizing to one of the capture probes and thereby associating each subset of n capture extenders with a selected subset of the particles. When the nucleic acid of interest corresponding to a subset of n capture extenders is hybridized to the subset of n capture extenders, which are hybridized to the corresponding capture probe, the nucleic acid of interest is hybridized to the subset of n capture extenders at a hybridization temperature which is greater than a melting temperature $T_m$ of a complex between each individual capture extender and the capture probe. The kit optionally also includes instructions for using the kit to capture and detect the nucleic acids of interest, one or more buffered solutions (e.g., lysis buffer, diluent, hybridization buffer, and/or wash buffer), standards comprising one or more nucleic acids at known concentration, and/or the like.

Essentially all of the features noted for the embodiments above apply to these embodiments as well, as relevant; for example, with respect to number of capture extenders per subset, composition of the label probe system, type of label, inclusion of blocking probes, configuration of the capture extenders, capture probes, label extenders, and/or blocking probes, number of nucleic acids of interest and of subsets of particles, capture extenders and label extenders, source of the sample and/or nucleic acids, and/or the like.

Yet another general class of embodiments includes methods of detecting two or more nucleic acids of interest. In the methods, a sample, a solid support, and two or more subsets of n capture extenders, wherein n is at least two, are provided. The sample comprises or is suspected of comprising the nucleic acids of interest. The solid support comprises two or more capture probes, each of which is provided at a selected position on the solid support. Each subset of n capture extenders is capable of hybridizing to one of the nucleic acids of interest, and the capture extenders in each subset are capable of hybridizing to one of the capture probes and thereby associating each subset of n capture extenders with a selected position on the solid support. Each nucleic acid of interest can thus, by hybridizing to its corresponding subset of n capture extenders which are in turn hybridized to a corresponding capture probe, be associated with, e.g., a known, predetermined location on the solid support. The sample, the solid support, and the subsets of n capture extenders are contacted, any nucleic acid of interest present in the sample is hybridized to its corresponding subset of n capture extenders, and the subset of n capture extenders is hybridized to its corresponding capture probe. The hybridizing the nucleic acid of interest to the n capture extenders and the n capture extenders to the corresponding capture probe captures the nucleic acid on the solid support at the selected position with which the capture extenders are associated. To determine which positions on the solid support have a nucleic acid of interest captured at that position, one or more label extenders and a label probe system comprising a label are hybridized to any nucleic acid of interest captured on the solid support, and the presence or absence of the label at the selected positions on the solid support is detected. Since a correlation exists between a particular position on the support and a particular nucleic acid of interest, which positions have a label present indicates which of the nucleic acids of interest were present in the sample.

Hybridizing the subset of n capture extenders to the corresponding capture probe is optionally performed at a hybridization temperature which is greater than a melting temperature $T_m$ of a complex between each individual capture extender and its corresponding capture probe.

Essentially all of the features noted for the embodiments above apply to these embodiments as well, as relevant; for example, with respect to number of capture extenders per subset, composition of the label probe system, type of label, inclusion of blocking probes, configuration of the capture extenders, capture probes, label extenders, and/or blocking probes, number of nucleic acids of interest and of selected positions on the solid support, capture extenders and label extenders, source of the sample and/or nucleic acids, and/or the like.

Another general class of embodiments provides a composition for detecting two or more nucleic acids of interest, the composition that includes a solid support comprising two or more capture probes, each of which is provided at a selected position on the solid support, two or more subsets of n capture extenders, wherein n is at least two, two or more subsets of one or more label extenders, and a label probe system comprising a label. Each subset of n capture extenders is capable of hybridizing to one of the nucleic acids of interest, and the capture extenders in each subset are capable of hybridizing to one of the capture probes and thereby associating each subset of n capture extenders with a selected position on the solid support.

Essentially all of the features noted for the embodiments above apply to these embodiments as well, as relevant; for example, with respect to number of capture extenders per subset, composition of the label probe system, type of label, inclusion of blocking probes, configuration of the capture extenders, capture probes, label extenders, and/or blocking probes, number of nucleic acids of interest and of selected positions on the solid support, capture extenders and label extenders, source of the sample and/or nucleic acids, and/or the like.

Yet another general class of embodiments provides a kit for detecting two or more nucleic acids of interest. The kit includes a solid support comprising two or more capture probes, each of which is provided at a selected position on the solid support, two or more subsets of n capture extenders, wherein n is at least two, two or more subsets of one or more label extenders, and a label probe system comprising a label, packaged in one or more containers. Each subset of n capture extenders is capable of hybridizing to one of the nucleic acids of interest, and the capture extenders in each subset are capable of hybridizing to one of the capture probes and thereby associating each subset of n capture extenders with a selected position on the solid support. The kit optionally also includes instructions for using the kit to capture and detect the nucleic acids of interest, one or more buffered solutions (e.g., lysis buffer, diluent, hybridization buffer, and/or wash buffer), standards comprising one or more nucleic acids at known concentration, and/or the like.

Essentially all of the features noted for the embodiments above apply to these embodiments as well, as relevant; for example, with respect to number of capture extenders per subset, composition of the label probe system, type of label, inclusion of blocking probes, configuration of the capture extenders, capture probes, label extenders, and/or blocking probes, number of nucleic acids of interest and of selected positions on the solid support, capture extenders and label extenders, source of the sample and/or nucleic acids, and/or the like.

BRIEF DESCRIPTION OF THE DRAWINGS

FIG. 6 Panel A schematically depicts simple hybridization of a single CE to a CP and a target mRNA. Panel B schematically depicts cooperative hybridization of CEs to a CP and a target mRNA. Panel C depicts a bar graph illustrating simple hybridization between a CE and CP under standard bDNA assay conditions. Panel D depicts a line graph illustrating cooperative hybridization between CEs and CPs under standard bDNA assay conditions.

FIG. 8 Panel A depicts a bar graph illustrating induction of cytokine gene expression upon PMA/LPS treatment of U937 cells, as detected by a 10-plex bDNA assay. Panel B depicts a bar graph illustrating induction of cytokine gene expression upon PMA/LPS treatment of U937 cells, as detected by single-plex bDNA assays using the same cell lysates.

Figure 1:
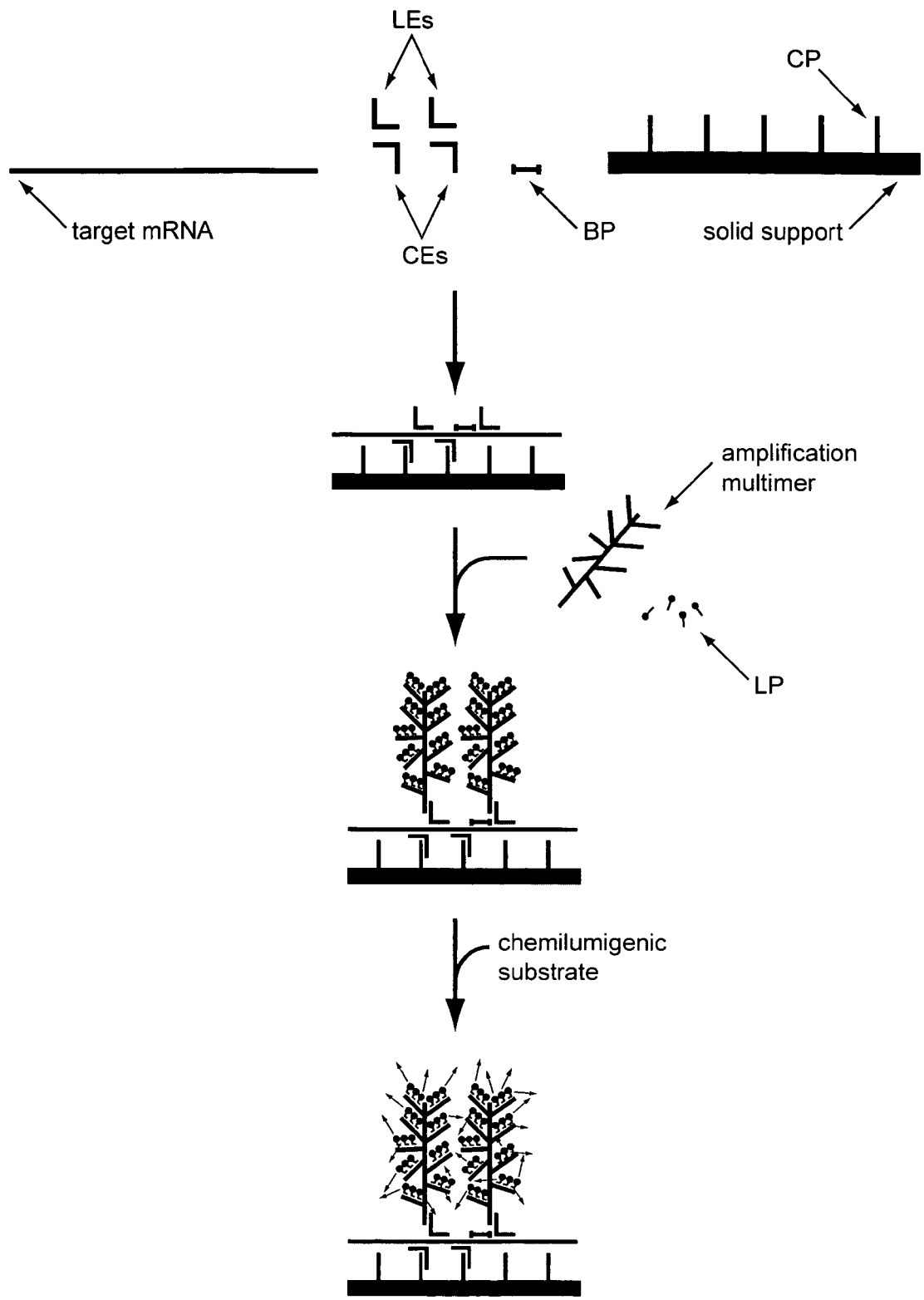
FIG. 1 schematically illustrates a typical standard bDNA assay.
Figure 2E:
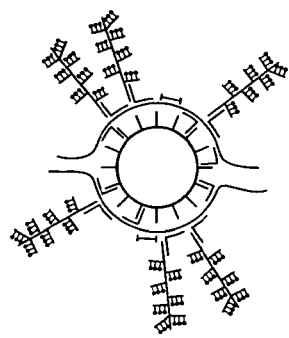
FIG. 2 Panels A-E schematically depict a multiplex bDNA assay, in which the nucleic acids of interest are captured on distinguishable subsets of microspheres and then detected.
Figure 2E:
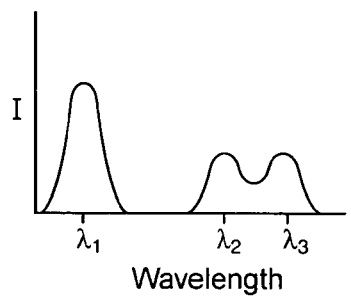
Figure 2E:
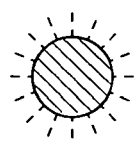
Figure 2E:
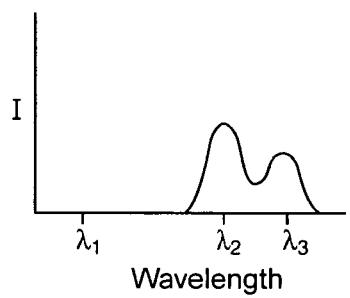
Figure 2E:
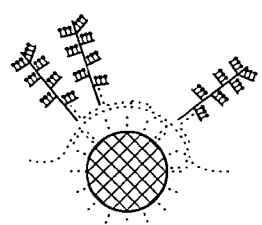
Figure 2E:
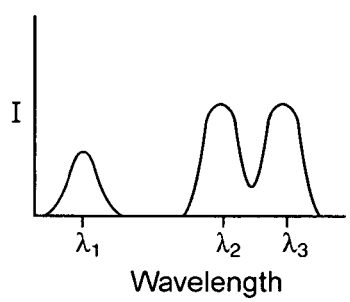

Schematic figures are not necessarily to scale.

DEFINITIONS

Unless defined otherwise, all technical and scientific terms used herein have the same meaning as commonly understood by one of ordinary skill in the art to which the invention pertains. The following definitions supplement those in the art and are directed to the current application and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a molecule" includes a plurality of such molecules, and the like.

The term "about" as used herein indicates the value of a given quantity varies by +/−10% of the value, or optionally +/−5% of the value, or in some embodiments, by +/−1% of the value so described.

The term "polynucleotide" (and the equivalent term "nucleic acid") encompasses any physical string of monomer units that can be corresponded to a string of nucleotides, including a polymer of nucleotides (e.g., a typical DNA or RNA polymer), peptide nucleic acids (PNAs), modified oligonucleotides (e.g., oligonucleotides comprising nucleotides that are not typical to biological RNA or DNA, such as 2'-O-methylated oligonucleotides), and the like. The nucleotides of the polynucleotide can be deoxyribonucleotides, ribonucleotides or nucleotide analogs, can be natural or non-natural, and can be unsubstituted, unmodified, substituted or modified. The nucleotides can be linked by phosphodiester bonds, or by phosphorothioate linkages, methylphosphonate linkages, boranophosphate linkages, or the like. The polynucleotide can additionally comprise non-nucleotide elements such as labels, quenchers, blocking groups, or the like. The polynucleotide can be, e.g., single-stranded or double-stranded.

A "polynucleotide sequence" or "nucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

Two polynucleotides "hybridize" when they associate to form a stable duplex, e.g., under relevant assay conditions. Nucleic acids hybridize due to a variety of well characterized physico-chemical forces, such as hydrogen bonding, solvent exclusion, base stacking and the like. An extensive guide to the hybridization of nucleic acids is found in Tijssen (1993) Laboratory Techniques in Biochemistry and Molecular Biology-Hybridization with Nucleic Acid Probes, part I chapter 2, "Overview of principles of hybridization and the strategy of nucleic acid probe assays" (Elsevier, New York), as well as in Ausubel, infra.

The "$T_m$" (melting temperature) of a nucleic acid duplex under specified conditions (e.g., relevant assay conditions) is the temperature at which half of the base pairs in a population of the duplex are disassociated and half are associated. The $T_m$ for a particular duplex can be calculated and/or measured, e.g., by obtaining a thermal denaturation curve for the duplex (where the $T_m$ is the temperature corresponding to the midpoint in the observed transition from double-stranded to single-stranded form).

The term "complementary" refers to a polynucleotide that forms a stable duplex with its "complement," e.g., under relevant assay conditions. Typically, two polynucleotide sequences that are complementary to each other have mismatches at less than about 20% of the bases, at less than about 10% of the bases, preferably at less than about 5% of the bases, and more preferably have no mismatches.

A "capture extender" or "CE" is a polynucleotide that is capable of hybridizing to a nucleic acid of interest and to a capture probe. The capture extender typically has a first polynucleotide sequence C-1, which is complementary to the capture probe, and a second polynucleotide sequence C-3, which is complementary to a polynucleotide sequence of the nucleic acid of interest. Sequences C-1 and C-3 are typically not complementary to each other. The capture extender is preferably single-stranded.

A "capture probe" or "CP" is a polynucleotide that is capable of hybridizing to at least one capture extender and that is tightly bound (e.g., covalently or noncovalently, directly or through a linker, e.g., streptavidin-biotin or the like) to a solid support, a spatially addressable solid support, a slide, a particle, a microsphere, or the like. The capture probe typically comprises at least one polynucleotide sequence C-2 that is complementary to polynucleotide sequence C-1 of at least one capture extender. The capture probe is preferably single-stranded.

A "label extender" or "LE" is a polynucleotide that is capable of hybridizing to a nucleic acid of interest and to a label probe system. The label extender typically has a first polynucleotide sequence L-1, which is complementary to a polynucleotide sequence of the nucleic acid of interest, and a second polynucleotide sequence L-2, which is complementary to a polynucleotide sequence of the label probe system (e.g., L-2 can be complementary to a polynucleotide sequence of an amplification multimer, a preamplifier, a label probe, or the like). The label extender is preferably single-stranded.

A "label" is a moiety that facilitates detection of a molecule. Common labels in the context of the present invention include fluorescent, luminescent, light-scattering, and/or colorimetric labels. Suitable labels include enzymes and fluorescent moieties, as well as radionuclides, substrates, cofactors, inhibitors, chemiluminescent moieties, magnetic particles, and the like. Patents teaching the use of such labels include U.S. Pat. Nos. 3,817,837; 3,850,752; 3,939,350; 3,996,345; 4,277,437; 4,275,149; and 4,366,241. Many labels are commercially available and can be used in the context of the invention.

A "label probe system" comprises one or more polynucleotides that collectively comprise a label and a polynucleotide sequence M-1, which is capable of hybridizing to at least one label extender. The label provides a signal, directly or indirectly. Polynucleotide sequence M-1 is typically complementary to sequence L-2 in the label extenders. The label probe system can include a plurality of label probes (e.g., a plurality of identical label probes) and an amplification multimer; it optionally also includes a preamplifier or the like, or optionally includes only label probes, for example.

An "amplification multimer" is a polynucleotide comprising a plurality of polynucleotide sequences M-2, typically (but not necessarily) identical polynucleotide sequences M-2. Polynucleotide sequence M-2 is complementary to a polynucleotide sequence in the label probe. The amplification multimer also includes at least one polynucleotide sequence that is capable of hybridizing to a label extender or to a nucleic acid that hybridizes to the label extender, e.g., a preamplifier. For example, the amplification multimer optionally includes at least one polynucleotide sequence M-1; polynucleotide sequence M-1 is typically complementary to polynucleotide sequence L-2 of the label extenders. Similarly, the amplification multimer optionally includes at least one polynucleotide sequence that is complementary to a polynucleotide sequence in a preamplifier. The amplification multimer can be, e.g., a linear or a branched nucleic acid. As noted for all polynucleotides, the amplification multimer can include modified nucleotides and/or nonstandard internucleotide linkages as well as standard deoxyribonucleotides, ribonucleotides, and/or phosphodiester bonds. Suitable amplification multimers are described, for example, in U.S. Pat. No. 5,635,352, U.S. Pat. No. 5,124,246, U.S. Pat. No. 5,710,264, and U.S. Pat. No. 5,849,481.

A "label probe" or "LP" is a single-stranded polynucleotide that comprises a label (or optionally that is configured to bind to a label) that directly or indirectly provides a detectable signal. The label probe typically comprises a polynucleotide sequence that is complementary to the repeating polynucleotide sequence M-2 of the amplification multimer; however, if no amplification multimer is used in the bDNA assay, the label probe can, e.g., hybridize directly to a label extender.

A "preamplifier" is a nucleic acid that serves as an intermediate between at least one label extender and amplification multimer. Typically, the preamplifier is capable of hybridizing simultaneously to at least one label extender and to a plurality of amplification multimers.

A "microsphere" is a small spherical, or roughly spherical, particle. A microsphere typically has a diameter less than about 1000 micrometers (e.g., less than about 100 micrometers, optionally less than about 10 micrometers).

A "microorganism" is an organism of microscopic or submicroscopic size. Examples include, but are not limited to, bacteria, fungi, yeast, protozoans, microscopic algae (e.g., unicellular algae), viruses (which are typically included in this category although they are incapable of growth and reproduction outside of host cells), subviral agents, viroids, and mycoplasma.

A variety of additional terms are defined or otherwise characterized herein.

DETAILED DESCRIPTION

The present invention provides methods, compositions, and kits for multiplex detection of nucleic acids. Nucleic acids of interest are captured to distinct subsets of particles or to selected positions on a solid support through cooperative hybridization, and they are then detected in a branched-chain DNA assay.

Branched-chain DNA (bDNA) signal amplification technology has been used, e.g., to detect and quantify mRNA transcripts in cell lines and to determine viral loads in blood. The bDNA assay is a sandwich nucleic acid hybridization procedure that enables direct measurement of mRNA expression, e.g., from crude cell lysate. It provides direct quantification of nucleic acid molecules at physiological levels. Several advantages of the technology distinguish it from other DNA/RNA amplification technologies, including linear amplification, good sensitivity and dynamic range, great precision and accuracy, simple sample preparation procedure, and reduced sample-to-sample variation.

In brief, in a typical bDNA assay for gene expression analysis (FIG. 1), a target mRNA whose expression is to be detected is released from cells and captured by a Capture Probe (CP) on a solid surface (e.g., a well of a microtiter plate) through synthetic oligonucleotide probes called Capture Extenders (CEs). Each capture extender has a first polynucleotide sequence that can hybridize to the target mRNA and a second polynucleotide sequence that can hybridize to the capture probe. Typically, two or more capture extenders are used. Probes of another type, called Label Extenders (LEs), hybridize to different sequences on the target mRNA and to sequences on an amplification multimer. Additionally, Blocking Probes (BPs) are often used to reduce non-specific target probe binding. A probe set for a given mRNA thus consists of CEs, LEs, and optionally BPs for the target mRNA. The CEs, LEs, and BPs are complementary to nonoverlapping sequences in the target mRNA, and are typically, but not necessarily, contiguous.

Signal amplification begins with the binding of the LEs to the target mRNA. An amplification multimer is then typically hybridized to the LEs. The amplification multimer has multiple copies of a sequence that is complementary to a label probe (it is worth noting that the amplification multimer is typically, but not necessarily, a branched-chain nucleic acid; for example, the amplification multimer can be a branched, forked, or comb-like nucleic acid or a linear nucleic acid). A label, for example, alkaline phosphatase, is covalently attached to each label probe. (Alternatively, the label can be noncovalently bound to the label probes.) In the final step, labeled complexes are detected, e.g., by the alkaline phosphatase-mediated degradation of a chemilumigenic substrate, e.g., dioxetane. Luminescence is reported as relative light unit (RLUs) on a microplate reader. The amount of chemiluminescence is proportional to the level of mRNA expressed from the target gene.

In the preceding example, the amplification multimer and the label probes comprise a label probe system. In another example, the label probe system also comprises a preamplifier, e.g., as described in U.S. Pat. No. 5,635,352 and U.S. Pat. No. 5,681,697, which further amplifies the signal from a single target mRNA. In yet another example, the label extenders hybridize directly to the label probes and no amplification multimer or preamplifier is used, so the signal from a single target mRNA molecule is only amplified by the number of distinct label extenders that hybridize to that mRNA.

Basic bDNA assays have been well described. See, e.g., U.S. Pat. No. 4,868,105 to Urdea et al. entitled "Solution phase nucleic acid sandwich assay"; U.S. Pat. No. 5,635,352 to Urdea et al. entitled "Solution phase nucleic acid sandwich assays having reduced background noise"; U.S. Pat. No. 5,681,697 to Urdea et al. entitled "Solution phase nucleic acid sandwich assays having reduced background noise and kits therefor"; U.S. Pat. No. 5,124,246 to Urdea et al. entitled "Nucleic acid multimers and amplified nucleic acid hybridization assays using same"; U.S. Pat. No. 5,624,802 to Urdea et al. entitled "Nucleic acid multimers and amplified nucleic acid hybridization assays using same"; U.S. Pat. No. 5,849,481 to Urdea et al. entitled "Nucleic acid hybridization assays employing large comb-type branched polynucleotides"; U.S. Pat. No. 5,710,264 to Urdea et al. entitled "Large comb type branched polynucleotides"; U.S. Pat. No. 5,594,118 to Urdea and Horn entitled "Modified N-4 nucleotides for use in amplified nucleic acid hybridization assays"; U.S. Pat. No. 5,093,232 to Urdea and Horn entitled "Nucleic acid probes"; U.S. Pat. No. 4,910,300 to Urdea and Horn entitled "Method for making nucleic acid probes"; U.S. Pat. No. 5,359,100; U.S. Pat. No. 5,571,670; U.S. Pat. No. 5,614,362; U.S. Pat. No. 6,235,465; U.S. Pat. No. 5,712,383; U.S. Pat. No. 5,747,244; U.S. Pat. No. 6,232,462; U.S. Pat. No. 5,681,702; U.S. Pat. No. 5,780,610; U.S. Pat. No. 5,780,227 to Sheridan et al. entitled "Oligonucleotide probe conjugated to a purified hydrophilic alkaline phosphatase and uses thereof"; U.S. patent application Publication No. US2002172950 by Kenny et al. entitled "Highly sensitive gene detection and localization using in situ branched-DNA hybridization"; Wang et al. (1997) "Regulation of insulin preRNA splicing by glucose" Proc Nat Acad Sci USA 94:4360-4365; Collins et al. (1998) "Branched DNA (bDNA) technology for direct quantification of nucleic acids: Design and performance" in Gene Quantification, F Ferre, ed.; and Wilber and Urdea (1998) "Quantification of HCV RNA in clinical specimens by branched DNA (bDNA) technology" Methods in Molecular Medicine: Hepatitis C 19:71-78. In addition, kits for performing basic bDNA assays (QuantiGene™ kits, comprising instructions and reagents such as amplification multimers, alkaline phosphatase labeled label probes, chemilumigenic substrate, capture probes immobilized on a solid support, and the like) are commercially available, e.g., from Panomics, Inc. (on the world wide web at (www.) panomics.com). Software for designing probe sets for a given mRNA target (i.e., for designing the regions of the CEs, LEs, and optionally BPs that are complementary to the target) is also commercially available (e.g., ProbeDesigner™ from Panomics, Inc.; see also Bushnell et al. (1999) "ProbeDesigner: for the design of probe sets for branched DNA (bDNA) signal amplification assays Bioinformatics 15:348-55).

The basic bDNA assay, however, permits detection of only a single target nucleic acid per assay, while, as described above, detection of multiple nucleic acids is frequently desirable.

Among other aspects, the present invention provides a multiplex bDNA assay that can be used for simultaneous detection of two or more target nucleic acids. The assay temperature and the stability of the complex between a single CE and its corresponding CP can be controlled such that binding of a single CE to a nucleic acid and to the CP is not sufficient to stably capture the nucleic acid on the surface to which the CP is bound, whereas simultaneous binding of two or more CEs to a nucleic acid can capture it on the surface. Requiring such cooperative hybridization of multiple CEs for capture of each nucleic acid of interest results in high specificity and low background from cross-hybridization of the CEs with other, non-target nucleic acids. For an assay to achieve high specificity and sensitivity, it preferably has a low background, resulting, e.g., from minimal cross-hybridization. Such low background and minimal cross-hybridization are typically substantially more difficult to achieve in a multiplex assay than a single-plex assay, because the number of potential nonspecific interactions are greatly increased in a multiplex assay due to the increased number of probes used in the assay (e.g., the greater number of CEs and LEs). Requiring multiple simultaneous CE-CP interactions for the capture of a target nucleic acid minimizes the chance that nonspecific capture will occur, even when some nonspecific CE-CP interactions do occur.

The methods of the invention can be used for multiplex detection of two or more nucleic acids simultaneously, for example, from even complex samples, without requiring prior purification of the nucleic acids, when the nucleic acids are present at low concentration, and/or in the presence of other, highly similar nucleic acids. In one aspect, the methods involve capture of the nucleic acids to particles (e.g., distinguishable subsets of microspheres), while in another aspect, the nucleic acids are captured to a spatially addressable solid support. Compositions, kits, and systems related to the methods are also provided.

Methods

As noted, one aspect of the invention provides multiplex bDNA assays. Thus, one general class of embodiments includes methods of detecting two or more nucleic acids of interest. In the methods, a sample, a pooled population of particles, and two or more subsets of n capture extenders, wherein n is at least two, are provided. The sample comprises or is suspected of comprising the nucleic acids of interest. The pooled population of particles includes two or more subsets of particles, and a plurality of the particles in each subset are distinguishable from a plurality of the particles in every other subset. (Typically, substantially all of the particles in each subset are distinguishable from substantially all of the particles in every other subset.) The particles in each subset have associated therewith a different capture probe. Each subset of n capture extenders is capable of hybridizing to one of the nucleic acids of interest, and the capture extenders in each subset are capable of hybridizing to one of the capture probes and thereby associating each subset of n capture extenders with a selected subset of the particles. Each nucleic acid of interest can thus, by hybridizing to its corresponding subset of n capture extenders which are in turn hybridized to a corresponding capture probe, be associated with an identifiable subset of the particles.

The sample, the pooled population of particles, and the subsets of n capture extenders are contacted, any nucleic acid of interest present in the sample is hybridized to its corresponding subset of n capture extenders, and the subset of n capture extenders is hybridized to its corresponding capture probe. The hybridizing the nucleic acid of interest to the n capture extenders and the n capture extenders to the corresponding capture probe captures the nucleic acid on the subset of particles with which the capture extenders are associated. The hybridizing the subset of n capture extenders to the corresponding capture probe is performed at a hybridization temperature which is greater than a melting temperature $T_m$ of a complex between each individual capture extender and its corresponding capture probe. Binding of a single capture extender to its corresponding nucleic acid (or to an extraneous nucleic acid) and capture probe is thus typically insufficient to capture the nucleic acid on the corresponding subset of particles. It will be evident that the hybridization temperature is typically less than a $T_m$ of a complex between the nucleic acid of interest, all n corresponding capture extenders, and the corresponding capture probe.

To determine which subsets of particles have a nucleic acid of interest captured on the particles, one or more (e.g., two or more) label extenders and a label probe system comprising a label are hybridized to any nucleic acid of interest captured on the particles, and at least a portion of the particles from each subset are identified and the presence or absence of the label is detected on those particles. Since a correlation exists between a particular subset of particles and a particular nucleic acid of interest, which subsets of particles have the label present indicates which of the nucleic acids of interest were present in the sample.

The methods are useful for multiplex detection of nucleic acids, optionally highly multiplex detection. Thus, the two or more nucleic acids of interest (i.e., the nucleic acids to be detected) optionally comprise five or more, 10 or more, 20 or more, 30 or more, 40 or more, 50 or more, or even 100 or more nucleic acids of interest. A like number of subsets of particles and subsets of CEs are provided; thus, the two or more subsets of particles can comprise five or more, 10 or more, 20 or more, 30 or more, 40 or more, 50 or more, or even 100 or more subsets of particles, while the two or more subsets of n capture extenders can comprise five or more, 10 or more, 20 or more, 30 or more, 40 or more, 50 or more, or even 100 or more subsets of n capture extenders.

Essentially any suitable particles, e.g., particles having distinguishable characteristics and to which capture probes can be attached, can be used. For example, in one preferred class of embodiments, the particles are microspheres. The microspheres of each subset can be distinguishable from those of the other subsets, e.g., on the basis of their fluorescent emission spectrum, their diameter, or a combination thereof. For example, the microspheres of each subset can be labeled with a unique fluorescent dye or mixture of such dyes, quantum dots with distinguishable emission spectra, and/or the like. As another example, the particles of each subset can be identified by an optical barcode, unique to that subset, present on the particles.

The particles optionally have additional desirable characteristics. For example, the particles can be magnetic or paramagnetic, which provides a convenient means for separating the particles from solution, e.g., to simplify separation of the particles from any materials not bound to the particles.

As noted, each of the two or more subsets of capture extenders includes n capture extenders, where n is at least two. Preferably, n is at least three, and n can be at least four or at least five or more. Typically, but not necessarily, n is at most ten. For example, n can be between three and ten, e.g., between five and ten or between five and seven, inclusive. Use of fewer capture extenders can be advantageous, for example, in embodiments in which nucleic acids of interest are to be specifically detected from samples including other nucleic acids with sequences very similar to that of the nucleic acids of interest. In other embodiments (e.g., embodiments in which capture of as much of the nucleic acid as possible is desired), however, n can be more than 10, e.g., between 20 and 50. n can be the same for all of the subsets of capture extenders, but it need not be; for example, one subset can include three capture extenders while another subset includes five capture extenders. The n capture extenders in a subset preferably hybridize to nonoverlapping polynucleotide sequences in the corresponding nucleic acid of interest. The nonoverlapping polynucleotide sequences can, but need not be, consecutive within the nucleic acid of interest.

Each capture extender is capable of hybridizing to its corresponding capture probe. The capture extender typically includes a polynucleotide sequence C-1 that is complementary to a polynucleotide sequence C-2 in its corresponding capture probe. In one aspect, C-1 and C-2 are 20 nucleotides or less in length. In one class of embodiments, C-1 and C-2 are between 9 and 17 nucleotides in length (inclusive), preferably between 12 and 15 nucleotides (inclusive). For example, C-1 and C-2 can be 14, 15, 16, or 17 nucleotides in length, or they can be between 9 and 13 nucleotides in length (e.g., for lower hybridization temperatures, e.g., hybridization at room temperature).

The capture probe can include polynucleotide sequence in addition to C-2, or C-2 can comprise the entire polynucleotide sequence of the capture probe. For example, each capture probe optionally includes a linker sequence between the site of attachment of the capture probe to the particles and sequence C-2 (e.g., a linker sequence containing 8 Ts, as just one possible example).

It will be evident that the amount of overlap between each individual capture extender and its corresponding capture probe (i.e., the length of C-1 and C-2) affects the $T_m$ of the complex between that capture extender and capture probe, as does, e.g., the GC base content of sequences C-1 and C-2. Typically, all the capture probes are the same length (as are sequences C-1 and C-2) from subset of particles to subset. However, depending, e.g., on the precise nucleotide sequence of C-2, different capture probes optionally have different lengths and/or different length sequences C-2, to achieve the desired $T_m$. Different capture probe-capture extender complexes optionally have the same or different $T_m$s.

It will also be evident that the number of capture extenders required for stable capture of a nucleic acid depends, in part, on the amount of overlap between the capture extenders and the capture probe (i.e., the length of C-1 and C-2). For example, if n is 5-7 for a 14 nucleotide overlap, n could be 3-5 for a 15 nucleotide overlap or 2-3 for a 16 nucleotide overlap.

As noted, the hybridizing the subset of n capture extenders to the corresponding capture probe is performed at a hybridization temperature which is greater than a melting temperature $T_m$ of a complex between each individual capture extender and its corresponding capture probe. The hybridization temperature is typically about 5° C. or more greater than the $T_m$, e.g., about 7° C. or more, about 10° C. or more, about 12° C. or more, about 15° C. or more, about 17° C. or more, or even about 20° C. or more greater than the $T_m$.

Stable capture of nucleic acids of interest, e.g., while minimizing capture of extraneous nucleic acids (e.g., those to which n−1 or fewer of the capture extenders bind) can be achieved, for example, by balancing n (the number of capture extenders), the amount of overlap between the capture extenders and the capture probe (the length of C-1 and C-2), and/or the stringency of the conditions under which the capture extenders, the nucleic acids, and the capture probes are hybridized.

Appropriate combinations of n, amount of complementarity between the capture extenders and the capture probe, and stringency of hybridization can, for example, be determined experimentally by one of skill in the art. For example, as illustrated in the experiments described in Example 1 herein, a particular value of n and a particular set of hybridization conditions can be selected, while the number of nucleotides of complementarity between the capture extenders and the capture probe is varied until hybridization of the n capture extenders to a nucleic acid captures the nucleic acid while hybridization of a single capture extender does not efficiently capture the nucleic acid. The experiments described in Example 1 also illustrate selection of n, amount of complementarity, and stringency of hybridization such that the desired nucleic acid of interest is captured while other nucleic acids present in the sample are not efficiently captured. Stringency can be controlled, for example, by controlling the formamide concentration, chaotropic salt concentration, salt concentration, pH, organic solvent content, and/or hybridization temperature.

As noted, the $T_m$ of any nucleic acid duplex can be directly measured, using techniques well known in the art. For example, a thermal denaturation curve can be obtained for the duplex, the midpoint of which corresponds to the $T_m$. It will be evident that such denaturation curves can be obtained under conditions having essentially any relevant pH, salt concentration, solvent content, and/or the like.

The $T_m$ for a particular duplex (e.g., an approximate $T_m$) can also be calculated. For example, the $T_m$ for an oligonucleotide-target duplex can be estimated using the following algorithm, which incorporates nearest neighbor thermodynamic parameters: Tm (Kelvin)=$\Delta H°/(\Delta S°+R \ln C_t)$, where the changes in standard enthalpy ($\Delta H°$) and entropy ($\Delta S°$) are calculated from nearest neighbor thermodynamic parameters (see, e.g., SantaLucia (1998) "A unified view of polymer, dumbbell, and oligonucleotide DNA nearest-neighbor thermodynamics" Proc. Natl. Acad. Sci. USA 95:1460-1465, Sugimoto et al. (1996) "Improved thermodynamic parameters and helix initiation factor to predict stability of DNA duplexes" Nucleic Acids Research 24: 4501-4505, Sugimoto et al. (1995) "Thermodynamic parameters to predict stability of RNA/DNA hybrid duplexes" Biochemistry 34:11211-11216, and et al. (1998) "Thermodynamic parameters for an expanded nearest-neighbor model for formation of RNA duplexes with Watson-Crick base pairs" Biochemistry 37: 14719-14735), R is the ideal gas constant (1.987 cal·K$^{-1}$mole$^{-1}$), and $C_t$ is the molar concentration of the oligonucleotide. The calculated $T_m$ is optionally corrected for salt concentration, e.g., Na$^+$ concentration, using the formula $1/T_m$ (Na$^+$)=$1/T_m$(1M)+(4.29f(G·C)–3.95)×10$^{-5}$ ln [Na$^+$]+9.40× 10$^{-6}$ ln$^2$[Na$^+$]. See, e.g., Owczarzy et al. (2004) "Effects of Sodium Ions on DNA Duplex Oligomers: Improved Predictions of Melting Temperatures" Biochemistry 43:3537-3554 for further details. A Web calculator for estimating Tm using the above algorithms is available on the Internet at scitools.idtdna.com/analyzer/oligocalc.asp. Other algorithms for calculating $T_m$ are known in the art and are optionally applied to the present invention.

In one class of embodiments, contacting the sample, the pooled population of particles, and the subsets of n capture extenders comprises combining the sample with the subsets of n capture extenders to form a mixture, and then combining the mixture with the pooled population of particles. In this class of embodiments, the capture extenders typically hybridize first to the corresponding nucleic acid of interest and then to the corresponding particle-associated capture probe. The hybridizations can, however, occur simultaneously or even in the opposite order. Thus, in another exemplary class of embodiments, contacting the sample, the pooled population of particles, and the subsets of n capture extenders comprises combining the sample, the subsets of capture extenders, and the pooled population of particles.

In a preferred class of embodiments, hybridizing one or more label extenders and a label probe system to any nucleic acid of interest captured on the particles comprises providing two or more subsets of one or more label probes, wherein each subset of label extenders is capable of hybridizing to one of the nucleic acids of interest, hybridizing any nucleic acid of interest captured on the particles to its corresponding subset of label extenders, and hybridizing the label probe system to the label extenders. The two or more subsets of label extenders can include, e.g., five or more, 10 or more, 20 or more, 30 or more, 40 or more, 50 or more, or even 100 or more subsets of label extenders. Typically, each subset includes two or more label extenders. The hybridizations can be performed simultaneously or sequentially, in essentially any order. As just one example, the capture extenders and label extenders can be hybridized to their corresponding nucleic acids of interest, then the capture extenders can be hybridized to their corresponding capture probes, and then the label probe system can be hybridized to the label extenders.

The label probe system optionally includes an amplification multimer and a plurality of label probes, wherein the amplification multimer is capable of hybridizing to a label extender and to a plurality of label probes. In another aspect, the label probe system includes a preamplifier, a plurality of amplification multimers, and a plurality of label probes, wherein the preamplifier hybridizes to the label extenders, and the amplification multimers hybridize to the preamplifier and to the plurality of label probes. As another example, the label probe system can include only label probes, which hybridize directly to the label extenders. In one class of embodiments, the label probe comprises the label. In other embodiments, the label probe is configured to bind a label; for example, a biotinylated label probe can bind to a streptavidin-associated label.

The label can be essentially any convenient label that directly or indirectly provides a detectable signal. In one aspect, the label is a fluorescent label (e.g., a fluorophore or quantum dot). Detecting the presence of the label on the particles thus comprises detecting a fluorescent signal from the label. Fluorescent emission by the label is typically distinguishable from any fluorescent emission by the particles, e.g., microspheres, and many suitable fluorescent label-fluorescent microsphere combinations are possible. As other examples, the label can be a luminescent label, a light-scattering label (e.g., colloidal gold particles), or an enzyme (e.g., HRP).

The methods can optionally be used to quantitate the amounts of the nucleic acids of interest present in the sample. For example, in one class of embodiments, an intensity of a signal from the label is measured, e.g., for each subset of particles, and correlated with a quantity of the corresponding nucleic acid of interest present.

As noted, blocking probes are optionally also hybridized to the nucleic acids of interest, which can reduce background in the assay. For a given nucleic acid of interest, the corresponding capture extenders, label extenders, and optional blocking probes are preferably complementary to physically distinct, nonoverlapping sequences in the nucleic acid of interest, which are preferably, but not necessarily, contiguous. The $T_m$s of the capture extender-nucleic acid, label extender-nucleic acid, and blocking probe-nucleic acid complexes are preferably greater than the hybridization temperature, e.g., by 5° C. or 10° C. or preferably by 15° C. or more, such that these complexes are stable at the hybridization temperature. Potential CE and LE sequences (e.g., potential sequences C-3 and L-1) are optionally examined for possible interactions with non-corresponding nucleic acids of interest, LEs or CEs, the amplification multimer, the preamplifier, the label probe, and/or any relevant genomic sequences, for example; sequences expected to cross-hybridize with undesired nucleic acids are typically not selected for use in the CEs or LEs. See, e.g., Example 1 herein and Player et al. (2001) "Single-copy gene detection using branched DNA (bDNA) in situ hybridization" J Histochem Cytochem 49:603-611. Examination can be, e.g., visual (e.g., visual examination for complementarity), computational (e.g., computation and comparison of binding free energies), and/or experimental (e.g., cross-hybridization experiments). Capture probe sequences are preferably similarly examined, to ensure that the polynucleotide sequence C-1 complementary to a particular capture probe's sequence C-2 is not expected to cross-hybridize with any of the other capture probes that are to be associated with other subsets of particles. See, e.g., Example 1 herein.

At any of various steps, materials not captured on the particles are optionally separated from the particles. For example, after the capture extenders, nucleic acids, label extenders, blocking probes, and particle-bound capture probes are hybridized, the particles are optionally washed to remove unbound nucleic acids and probes; after the label extenders and amplification multimer are hybridized, the particles are optionally washed to remove unbound amplification multimer; and/or after the label probes are hybridized to the amplification multimer, the particles are optionally washed to remove unbound label probe prior to detection of the label.

One or more of the subsets of particles is optionally isolated, whereby the associated nucleic acid of interest is isolated. The isolated nucleic acid can optionally be removed from the particles and/or subjected to further manipulation, if desired (e.g., amplification by PCR or the like).

An exemplary embodiment is schematically illustrated in FIG. 2. Panel A illustrates three distinguishable subsets of microspheres 201, 202, and 203, which have associated therewith capture probes 204, 205, and 206, respectively. Each capture probe includes a sequence C-2 (250), which is different from subset to subset of microspheres. The three subsets of microspheres are combined to form pooled population 208 (Panel B). A subset of three capture extenders is provided for each nucleic acid of interest; subset 211 for nucleic acid 214, subset 212 for nucleic acid 215 which is not present, and subset 213 for nucleic acid 216. Each capture extender includes sequences C-1 (251, complementary to the respective capture probe's sequence C-2) and C-3 (252, complementary to a sequence in the corresponding nucleic acid of interest). Three subsets of label extenders (221, 222, and 223 for nucleic acids 214, 215, and 216, respectively) and three subsets of blocking probes (224, 225, and 226 for nucleic acids 214, 215, and 216, respectively) are also provided. Each label extender includes sequences L-1 (254, complementary to a sequence in the corresponding nucleic acid of interest) and L-2 (255, complementary to M-1). Non-target nucleic acids 230 are also present in the sample of nucleic acids.

Nucleic acids 214 and 216 are hybridized to their corresponding subset of capture extenders (211 and 213, respectively), and the capture extenders are hybridized to the corresponding capture probes (204 and 206, respectively), capturing nucleic acids 214 and 216 on microspheres 201 and 203, respectively (Panel C). Materials not bound to the microspheres (e.g., capture extenders 212, nucleic acids 230, etc.) are separated from the microspheres by washing. Label probe system 240 including amplification multimer 241 (which includes sequences M-1 257 and M-2 258) and label probe 242 (which contains label 243) is hybridized to label extenders 221 and 223, which are hybridized to nucleic acids 214 and 216, respectively (Panel D). Materials not captured on the microspheres are optionally removed by washing the microspheres. Microspheres from each subset are identified, e.g., by their fluorescent emission spectrum ($\lambda_2$ and $\lambda_3$, Panel E), and the presence or absence of the label on each subset of microspheres is detected ($\lambda_1$, Panel E). Since each nucleic acid of interest is associated with a distinct subset of microspheres, the presence of the label on a given subset of microspheres correlates with the presence of the corresponding nucleic acid in the original sample.

As depicted in FIG. 2, all of the label extenders in all of the subsets typically include an identical sequence L-2. Optionally, however, different label extenders (e.g., label extenders in different subsets) can include different sequences L-2. Also as depicted in FIG. 2, each capture probe typically includes a single sequence C-2 and thus hybridizes to a single capture extender. Optionally, however, a capture probe can include two or more sequences C-2 and hybridize to two or more capture extenders. Similarly, as depicted, each of the capture extenders in a particular subset typically includes an identical sequence C-1, and thus only a single capture probe is needed for each subset of particles; however, different capture extenders within a subset optionally include different sequences C-1 (and thus hybridize to different sequences C-2, within a single capture probe or different capture probes on the surface of the corresponding subset of particles).

The methods can be used to detect the presence of the nucleic acids of interest in essentially any type of sample. For example, the sample can be derived from an animal, a human, a plant, a cultured cell, a virus, a bacterium, a pathogen, and/or a microorganism. The sample optionally includes a cell lysate, an intercellular fluid, a bodily fluid (including, but not limited to, blood, serum, saliva, urine, sputum, or spinal fluid), and/or a conditioned culture medium, and is optionally derived from a tissue (e.g., a tissue homogenate), a biopsy, and/or a tumor. Similarly, the nucleic acids can be essentially any desired nucleic acids. As just a few examples, the nucleic acids of interest can be derived from one or more of an animal, a human, a plant, a cultured cell, a microorganism, a virus, a bacterium, or a pathogen.

As noted, the methods can be used for gene expression analysis. Accordingly, in one class of embodiments, the two or more nucleic acids of interest comprise two or more mRNAs. The methods can also be used for clinical diagnosis and/or detection of microorganisms, e.g., pathogens. Thus, in certain embodiments, the nucleic acids include bacterial and/or viral genomic RNA and/or DNA (double-stranded or single-stranded), plasmid or other extra-genomic DNA, or other nucleic acids derived from microorganisms (pathogenic or otherwise). It will be evident that double-stranded nucleic acids of interest will typically be denatured before hybridization with capture extenders, label extenders, and the like.

Due to cooperative hybridization of multiple capture extenders to a nucleic acid of interest, for example, even nucleic acids present at low concentration can be captured and detected. Thus, in one class of embodiments, at least one of the nucleic acids of interest is present in the sample in a non-zero amount of 200 amol or less, 150 amol or less, 100 amol or less, 50 amol or less, 10 amol or less, 1 amol or less, or even 0.1 amol or less, 0.01 amol or less, 0.001 amol or less, or 0.0001 amol or less. Similarly, two nucleic acids of interest can be captured and detected simultaneously, even when they differ in concentration by 1000-fold or more in the sample. The methods are thus extremely versatile.

Capture of a particular nucleic acid is optionally quantitative. Thus, in one exemplary class of embodiments, the sample includes a first nucleic acid of interest, and at least 30%, at least 50%, at least 80%, at least 90%, at least 95%, or even at least 99% of a total amount of the first nucleic acid present in the sample is captured on a first subset of particles. Second, third, etc. nucleic acids can similarly be quantitatively captured. Such quantitative capture can occur without capture of a significant amount of undesired nucleic acids, even those of very similar sequence to the nucleic acid of interest.

Thus, in one class of embodiments, the sample comprises or is suspected of comprising a first nucleic acid of interest and a second nucleic acid which has a polynucleotide sequence which is 95% or more identical to that of the first nucleic acid (e.g., 96% or more, 97% or more, 98% or more, or even 99% or more identical). The first nucleic acid, if present in the sample, is captured on a first subset of particles, while the second nucleic acid comprises 1% or less of a total amount of nucleic acid captured on the first subset of particles (e.g., 0.5% or less, 0.2% or less, or even 0.1% or less). The second nucleic acid can be another nucleic acid of interest or simply any nucleic acid. Typically, capture extenders are chosen that hybridize to regions of the first nucleic acid having the greatest sequence difference from the second nucleic acid.

As just one example of how closely related nucleic acids can be distinguished using the methods of the invention, different splice variants of a given mRNA can be distinguished. Thus, in one class of embodiments, the sample comprises a first nucleic acid of interest and a second nucleic acid, where the first nucleic acid is a first splice variant and the second nucleic acid is a second splice variant of the given mRNA. A first subset of n capture extenders is capable of hybridizing to the first splice variant, of which at most n−1 capture extenders are capable of hybridizing to the second splice variant. Optionally, at least 80% or more, 90% or more, or 95% or more of the first splice variant is captured on a first subset of particles while at most 10% or less, 5% or less, 3% or less, or 1% or less of the second splice variant is captured on the first subset of particles. Preferably, hybridization of the n capture extenders to the first splice variant captures the first splice variant on a first subset of particles while hybridization of the at most n−1 capture extenders to the second splice variant does not capture the second splice variant on the first subset of particles.

Figure 3:
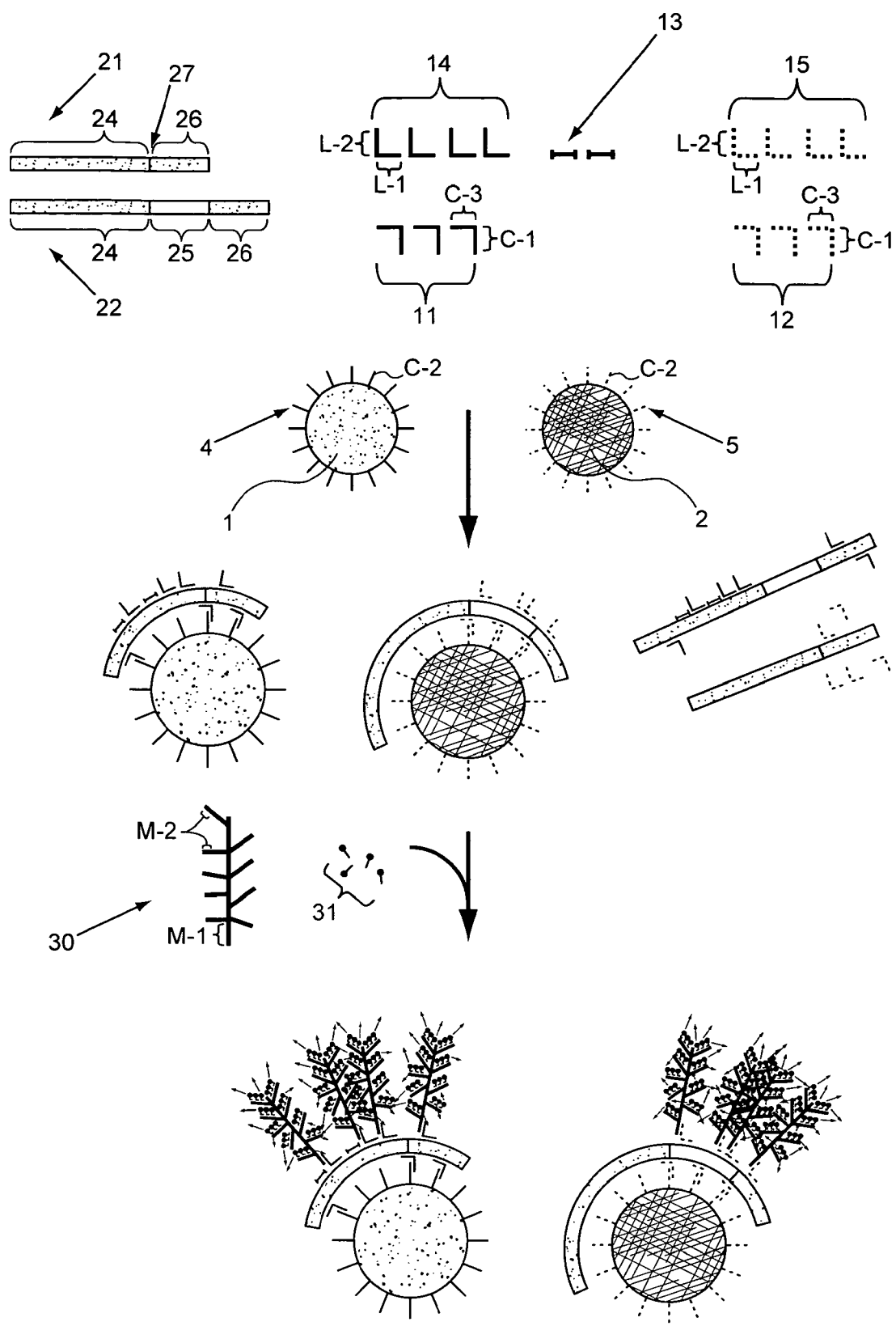
FIG. 3 schematically depicts an exemplary embodiment in which two splice variants are specifically captured on distinguishable subsets of microspheres and then detected.

An exemplary embodiment illustrating detection of two splice variants is schematically depicted in FIG. 3. In this example, three CEs 11 hybridize to first splice variant 21, one to each exon (24 and 26) and one to splice junction 27 (the only sequence found in first splice variant 21 and not also found in second splice variant 22); two of these bind to second splice variant 22. Similarly, three CEs 12 bind to second splice variant 22, one to intron 25 and one to each of the splice junctions; none of these bind to first splice variant 21. Through cooperative hybridization of the CEs to the splice variants and to the corresponding capture probes (4 and 5), splice variants 21 and 22 are each captured specifically only on the corresponding subset of microspheres (1 and 2, respectively). LEs 14 and 15 are hybridized with splice variants 21 and 22, respectively, and BPs 13 are hybridized with first splice variant 21. Amplification multimers 30 are then hybridized to the LEs, and label probes 31 are hybridized to the amplification multimers. Microspheres from the two subsets are then identified, and the presence or absence of the label on the microspheres is detected and correlated with the presence or absence of the corresponding splice variant. For additional details on detection of splice variants, see U.S. patent application 60/501,598, filed Sep. 9, 2003, by Yuling Luo, entitled "Methods of capturing, detecting, and quantitating splice variants." Optionally, for any nucleic acid, hybridization of a first subset of n capture extenders to a first nucleic acid captures the first nucleic acid on a first subset of particles while hybridization of at most n−1 of the capture extenders to a second nucleic acid does not capture the second nucleic acid on the first subset of particles.

It will be evident that nucleic acids that do not have 100% identical sequences are alternatively optionally captured on the same subset of particles, if desired. For example, a first and a second nucleic acid are optionally both captured on a first subset of particles, through binding of the same or different subsets of capture extenders. The first and second nucleic acids can be closely related; for example, splice variants of a particular mRNA, different alleles of a gene, somatic mutations, homologs, or the like.

A capture probe and/or capture extender optionally comprises at least one non-natural nucleotide. For example, a capture probe and the corresponding capture extender optionally comprise, at complementary positions, at least one pair of non-natural nucleotides that base pair with each other but that do not Watson-Crick base pair with the bases typical to biological DNA or RNA (i.e., A, C, G, T, or U). Examples of nonnatural nucleotides include, but are not limited to, Locked NucleicAcid™ nucleotides (available from Exiqon A/S, (www.) exiqon.com; see, e.g., SantaLucia Jr. (1998) Proc Natl Acad Sci 95:1460-1465) and isoG, isoC, and other nucleotides used in the AEGIS system (Artificially Expanded Genetic Information System, available from EraGen Biosciences, (www.) eragen.com; see, e.g., U.S. Pat. No. 6,001, 983, U.S. Pat. No. 6,037,120, and U.S. Pat. No. 6,140,496). Use of such non-natural base pairs (e.g., isoG-isoC base pairs) in the capture probes and capture extenders can, for example, reduce background and/or simplify probe design by decreasing cross hybridization, or it can permit use of shorter CPs and CEs when the non-natural base pairs have higher binding affinities than do natural base pairs. (Non-natural nucleotides can similarly be included in the label extenders, preamplifiers, amplification multimers, and/or label probes, if desired.)

The preceding embodiments include capture of the nucleic acids of interest on particles. Alternatively, the nucleic acids can be captured at different positions on a non-particulate, spatially addressable solid support. Accordingly, another general class of embodiments includes methods of detecting two or more nucleic acids of interest. In the methods, a sample, a solid support, and two or more subsets of n capture extenders, wherein n is at least two, are provided. The sample comprises or is suspected of comprising the nucleic acids of interest. The solid support comprises two or more capture probes, each of which is provided at a selected position on the solid support. Each subset of n capture extenders is capable of hybridizing to one of the nucleic acids of interest, and the capture extenders in each subset are capable of hybridizing to one of the capture probes and thereby associating each subset of n capture extenders with a selected position on the solid support. Each nucleic acid of interest can thus, by hybridizing to its corresponding subset of n capture extenders which are in turn hybridized to a corresponding capture probe, be associated with, e.g., a known, predetermined location on the solid support. The sample, the solid support, and the subsets of n capture extenders are contacted, any nucleic acid of interest present in the sample is hybridized to its corresponding subset of n capture extenders, and the subset of n capture extenders is hybridized to its corresponding capture probe. The hybridizing the nucleic acid of interest to the n capture extenders and the n capture extenders to the corresponding capture probe captures the nucleic acid on the solid support at the selected position with which the capture extenders are associated. To determine which positions on the solid support have a nucleic acid of interest captured at that position, one or more (e.g., two or more) label extenders and a label probe system comprising a label are hybridized to any nucleic acid of interest captured on the solid support, and the presence or absence of the label at the selected positions on the solid support is detected. Since a correlation exists between a particular position on the support and a particular nucleic acid of interest, which positions have a label present indicates which of the nucleic acids of interest were present in the sample.

The hybridizing the subset of n capture extenders to the corresponding capture probe is typically performed at a hybridization temperature which is greater than a melting temperature $T_m$ of a complex between each individual capture extender and its corresponding capture probe. For example, the hybridization temperature can be about 5° C. or more greater than the $T_m$, e.g., about 7° C. or more, about 10° C. or more, about 12° C. or more, about 15° C. or more, about 17° C. or more, or even about 20° C. or more greater than the $T_m$.

The methods are useful for multiplex detection of nucleic acids, optionally highly multiplex detection. Thus, the two or more nucleic acids of interest (i.e., the nucleic acids to be detected) optionally comprise five or more, 10 or more, 20 or more, 30 or more, 40 or more, 50 or more, 100 or more, $10^3$ or more, or $10^4$ or more nucleic acids of interest. A like number of selected positions on the solid support and subsets of CEs are provided; thus, the two or more selected positions can comprise five or more, 10 or more, 20 or more, 30 or more, 40 or more, 50 or more, 100 or more, $10^3$ or more, or $10^4$ or more selected positions, while the two or more subsets of n capture extenders can comprise five or more, 10 or more, 20 or more, 30 or more, 40 or more, 50 or more, 100 or more, $10^3$ or more, or $10^4$ or more subsets of n capture extenders.

The solid support typically has a planar surface and is typically rigid, but essentially any spatially addressable solid support can be adapted to the practice of the present invention. Exemplary materials for the solid support include, but are not limited to, glass, silicon, silica, quartz, plastic, polystyrene, nylon, and nitrocellulose. As just one example, an array of capture probes can be formed at selected positions on a glass slide as the solid support.

Essentially all of the features noted for the methods above apply to these embodiments as well, as relevant; for example, with respect to number of capture extenders per subset, composition of the label probe system, type of label, use of blocking probes, configuration of the capture extenders, capture probes, label extenders, and/or blocking probes, quantitation of the nucleic acids of interest, source of the sample and/or nucleic acids, and/or the like.

For example, in one class of embodiments, contacting the sample, the solid support, and the subsets of n capture extenders comprises combining the sample with the subsets of n capture extenders to form a mixture, and then contacting the mixture with the solid support. In this class of embodiments, the capture extenders typically hybridize first to the corresponding nucleic acid of interest and then to the corresponding particle-associated capture probe. In other embodiments, however, the hybridizations can occur simultaneously or even in the opposite order.

At any of various steps, materials not captured on the solid support are optionally separated from the solid support. For example, after the capture extenders, nucleic acids, label extenders, blocking probes, and support-bound capture probes are hybridized, the solid support is optionally washed to remove unbound nucleic acids and probes; after the label extenders and amplification multimer are hybridized, the support is optionally washed to remove unbound amplification multimer; and/or after the label probes are hybridized to the amplification multimer, the support is optionally washed to remove unbound label probe prior to detection of the label.

As for the embodiments described above, capture of a particular nucleic acid is optionally quantitative. Thus, in one exemplary class of embodiments, the sample includes a first nucleic acid of interest, and at least 30%, at least 50%, at least 80%, at least 90%, at least 95%, or even at least 99% of a total amount of the first nucleic acid present in the sample is captured at a first selected position on the solid support. Second, third, etc. nucleic acids can similarly be quantitatively captured. Such quantitative capture can occur without capture of a significant amount of undesired nucleic acids, even those of very similar sequence to the nucleic acid of interest.

Thus, in one class of embodiments, the sample comprises or is suspected of comprising a first nucleic acid of interest and a second nucleic acid which has a polynucleotide sequence which is 95% or more identical to that of the first nucleic acid (e.g., 96% or more, 97% or more, 98% or more, or even 99% or more identical). The first nucleic acid, if present in the sample, is captured at a first selected position on the solid support, while the second nucleic acid comprises 1% or less of a total amount of nucleic acid captured at the first position (e.g., 0.5% or less, 0.2% or less, or even 0.1% or less). The second nucleic acid can be another nucleic acid of interest or simply any nucleic acid. Typically, capture extenders are chosen that hybridize to regions of the first nucleic acid having the greatest sequence difference from the second nucleic acid.

As just one example of how closely related nucleic acids can be distinguished using the methods of the invention, different splice variants of a given mRNA can be distinguished. Thus, in one class of embodiments, the sample comprises a first nucleic acid of interest and a second nucleic acid, where the first nucleic acid is a first splice variant and the second nucleic acid is a second splice variant of the given mRNA. A first subset of n capture extenders is capable of hybridizing to the first splice variant, of which at most n−1 capture extenders are capable of hybridizing to the second splice variant. Optionally, at least 80% or more, 90% or more, or 95% or more of the first splice variant is captured at a first selected position on the solid support while at most 10% or less, 5% or less, 3% or less, or 1% or less of the second splice variant is captured at the first position. Preferably, hybridization of the n capture extenders to the first splice variant captures the first splice variant at a first selected position on the solid support while hybridization of the at most n−1 capture extenders to the second splice variant does not capture the second splice variant at the first position.

It will be evident that nucleic acids that do not have 100% identical sequences are alternatively optionally captured at the same position of the support, if desired. For example, a first and a second nucleic acid are optionally both captured at a first position, through binding of the same or different subsets of capture extenders. The first and second nucleic acids can be closely related; for example, splice variants of a particular mRNA, different alleles of a gene, somatic mutations, homologs, or the like.

Figure 4D:
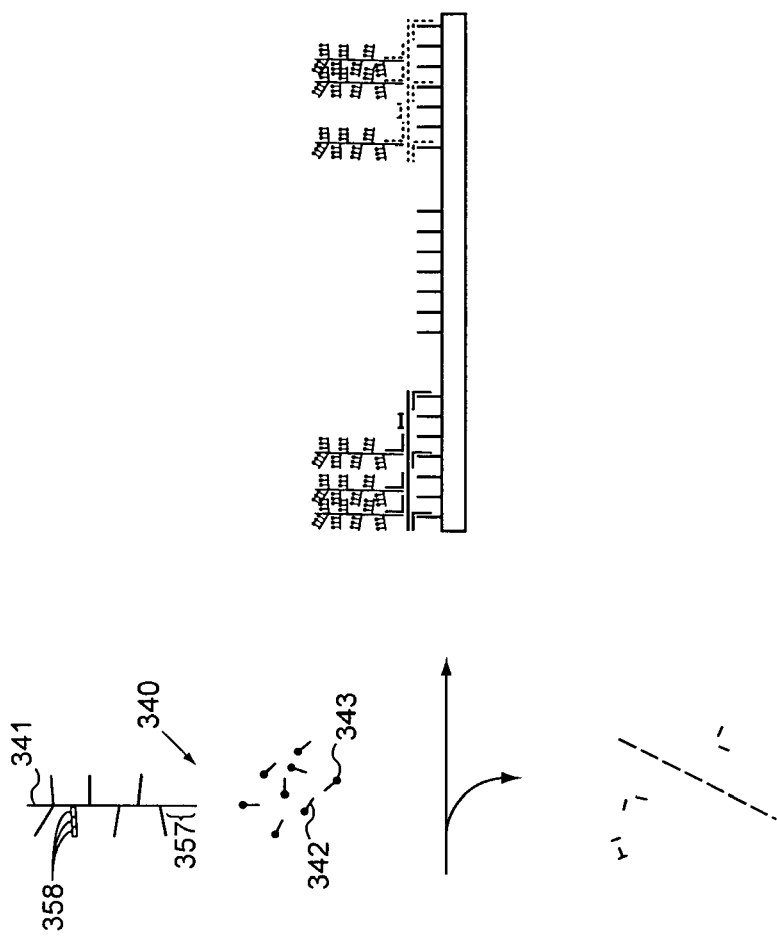
FIG. 4 Panels A-D schematically depict a multiplex bDNA assay, in which the nucleic acids of interest are captured at selected positions on a solid support and then detected. Panel A shows a top view of the solid support, while Panels B-D show the support in cross-section.

An exemplary embodiment is schematically illustrated in FIG. 4. Panel A depicts solid support 301 having nine capture probes provided on it at nine selected positions (e.g., 334-336). Panel B depicts a cross section of solid support 301, with distinct capture probes 304, 305, and 306 at different selected positions on the support (334, 335, and 336, respectively). A subset of capture extenders is provided for each nucleic acid of interest. Only three subsets are depicted; subset 311 for nucleic acid 314, subset 312 for nucleic acid 315 which is not present, and subset 313 for nucleic acid 316. Each capture extender includes sequences C-1 (351, complementary to the respective capture probe's sequence C-2) and C-3 (352, complementary to a sequence in the corresponding nucleic acid of interest). Three subsets of label extenders (321, 322, and 323 for nucleic acids 314, 315, and 316, respectively) and three subsets of blocking probes (324, 325, and 326 for nucleic acids 314, 315, and 316, respectively) are also depicted (although nine would typically be provided, one for each nucleic acid of interest). Each label extender includes sequences L-1 (354, complementary to a sequence in the corresponding nucleic acid of interest) and L-2 (355, complementary to M-1). Non-target nucleic acids 330 are also present in the sample of nucleic acids.

Nucleic acids 314 and 316 are hybridized to their corresponding subset of capture extenders (311 and 313, respectively), and the capture extenders are hybridized to the corresponding capture probes (304 and 306, respectively), capturing nucleic acids 314 and 316 at selected positions 334 and 336, respectively (Panel C). Materials not bound to the solid support (e.g., capture extenders 312, nucleic acids 330, etc.) are separated from the support by washing. Label probe system 340 including amplification multimer 341 (which includes sequences M-1 357 and M-2 358) and label probe 342 (which contains label 343) is hybridized to label extenders 321 and 323, which are hybridized to nucleic acids 314 and 316, respectively (Panel D). Materials not captured on the solid support are optionally removed by washing the support, and the presence or absence of the label at each position on the solid support is detected. Since each nucleic acid of interest is associated with a distinct position on the support, the presence of the label at a given position on the support correlates with the presence of the corresponding nucleic acid in the original sample.

The methods of the present invention offer a number of advantages. For example, a single array of capture probes at selected positions on a solid support can be manufactured, and this single array can be used to detect essentially any desired group of nucleic acids of interest simply by synthesizing appropriate subsets of capture extenders, label extenders, and the like. A new array need not be manufactured for each new group of nucleic acids to be detected, unlike conventional microarray technologies in which arrays of target-specific probes attached to a solid support are utilized, necessitating the manufacture of a new array for each new group of target nucleic acids to be detected. Similarly, a single population of subsets of particles comprising capture probes can be manufactured and used for detection of essentially any desired group of nucleic acids of interest.

Compositions

Compositions related to the methods are another feature of the invention. Thus, one general class of embodiments provides a composition for detecting two or more nucleic acids of interest, the composition that includes two or more subsets of particles, two or more subsets of n capture extenders, wherein n is at least two, two or more subsets of one or more label extenders, and a label probe system comprising a label. A plurality of the particles in each subset are distinguishable from a plurality of the particles in every other subset. (Typically, substantially all of the particles in each subset are distinguishable from substantially all of the particles in every other subset.) The particles in each subset have associated therewith a different capture probe. Each subset of n capture extenders is capable of hybridizing to one of the nucleic acids of interest, and the capture extenders in each subset are capable of hybridizing to one of the capture probes and thereby associating each subset of n capture extenders with a selected subset of the particles. When the nucleic acid of interest corresponding to a subset of n capture extenders is present in the composition and is hybridized to the subset of n capture extenders, which are hybridized to the corresponding capture probe, the nucleic acid of interest is hybridized to the subset of n capture extenders at a hybridization temperature which is greater than a melting temperature $T_m$ of a complex between each individual capture extender and the capture probe.

The composition optionally includes a sample comprising or suspected of comprising at least one of the nucleic acids of interest, e.g., two or more, three or more, etc. nucleic acids. In one class of embodiments, the composition comprises one or more of the nucleic acids of interest. Each nucleic acid of interest is hybridized to its corresponding subset of n capture extenders, and the corresponding subset of n capture extenders is hybridized to its corresponding capture probe. Each nucleic acid of interest is thus associated with an identifiable subset of the particles. The composition is maintained at the hybridization temperature.

As noted, the hybridization temperature is greater than the $T_m$ of each of the individual CE-CP complexes. The hybridization temperature is typically about 5° C. or more greater than the $T_m$, e.g., about 7° C. or more, about 10° C. or more, about 12° C. or more, about 15° C. or more, about 17° C. or more, or even about 20° C. or more greater than the $T_m$.

Essentially all of the features noted for the methods above apply to these embodiments as well, as relevant; for example, with respect to number of capture extenders per subset, composition of the label probe system, type of label, inclusion of blocking probes, configuration of the capture extenders, capture probes, label extenders, and/or blocking probes, number of nucleic acids of interest and of subsets of particles, capture extenders and label extenders, type of particles, source of the sample and/or nucleic acids, and/or the like.

As noted, even nucleic acids present at low concentration can be captured. Thus, in one class of embodiments, at least one of the nucleic acids of interest is present in the composition in a non-zero amount of 200 amol or less, 150 amol or less, 100 amol or less, 50 amol or less, 10 amol or less, 1 amol or less, or even 0.1 amol or less, 0.01 amol or less, 0.001 amol or less, or 0.0001 amol or less. Similarly, two nucleic acids of interest can be captured simultaneously, even when they differ in concentration by 1000-fold or more in the composition.

Capture of a particular nucleic acid on the particles is optionally quantitative. Thus, in one exemplary class of embodiments, the composition includes a first nucleic acid of interest, and at least 30%, at least 50%, at least 80%, at least 90%, at least 95%, or even at least 99% of a total amount of the first nucleic acid present in the composition is captured on a first subset of particles. Second, third, etc. nucleic acids can similarly be quantitatively captured. Such quantitative capture can occur without capture of a significant amount of undesired nucleic acids, even those of very similar sequence to the nucleic acid of interest.

Thus, in one class of embodiments, the composition comprises or is suspected of comprising a first nucleic acid of interest and a second nucleic acid which has a polynucleotide sequence which is 95% or more identical to that of the first nucleic acid (e.g., 96% or more, 97% or more, 98% or more, or even 99% or more identical). The first nucleic acid, if present in the composition, is captured on a first subset of particles, while the second nucleic acid comprises 1% or less of a total amount of nucleic acid captured on the first subset of particles (e.g., 0.5% or less, 0.2% or less, or even 0.1% or less). The second nucleic acid can be another nucleic acid of interest or simply any nucleic acid. Typically, capture extenders are chosen that hybridize to regions of the first nucleic acid having the greatest sequence difference from the second nucleic acid.

In one exemplary class of embodiments in which related nucleic acids are differentially captured, the composition comprises a first nucleic acid of interest and a second nucleic acid, where the first nucleic acid is a first splice variant and the second nucleic acid is a second splice variant of a given mRNA. A first subset of n capture extenders is capable of hybridizing to the first splice variant, of which at most n−1 capture extenders are capable of hybridizing to the second splice variant. Optionally, at least 80% or more, 90% or more, or 95% or more of the first splice variant is captured on a first subset of particles while at most 10% or less, 5% or less, 3% or less, or 1% or less of the second splice variant is captured on the first subset of particles. Preferably, a first subset of n capture extenders is hybridized to the first splice variant, whereby the first splice variant is captured on a first subset of particles, and at most n−1 of the capture extenders are hybridized to the second splice variant, whereby the second splice variant is not captured on the first subset of particles.

A related general class of embodiments provides a composition comprising two or more subsets of particles, two or more subsets of n capture extenders, wherein n is at least two, two or more subsets of one or more label extenders, a label probe system comprising a label, and at least a first nucleic acid of interest. A plurality of the particles in each subset are distinguishable from a plurality of the particles in every other subset. (Typically, substantially all of the particles in each subset are distinguishable from substantially all of the particles in every other subset.) The particles in each subset have associated therewith a different capture probe. Each subset of n capture extenders is capable of hybridizing to one of the nucleic acids of interest, and the capture extenders in each subset are capable of hybridizing to one of the capture probes and thereby associating each subset of n capture extenders with a selected subset of the particles. In this class of embodiments, the composition is maintained at a hybridization temperature, which hybridization temperature is greater than a melting temperature $T_m$ of a complex between each individual capture extender and its corresponding capture probe. The first nucleic acid of interest is hybridized to a first subset of n first capture extenders, which first capture extenders are hybridized to a first capture probe.

Essentially all of the features noted for the embodiments above apply to these embodiments as well, as relevant; for example, with respect to number of capture extenders per subset, composition of the label probe system, type of label, inclusion of blocking probes, configuration of the capture extenders, capture probes, label extenders, and/or blocking probes, number of nucleic acids of interest and of subsets of particles, capture extenders and label extenders, source of the sample and/or nucleic acids, and/or the like.

Another general class of embodiments provides a composition for detecting two or more nucleic acids of interest, the composition that includes a solid support comprising two or more capture probes, each of which is provided at a selected position on the solid support, two or more subsets of n capture extenders, wherein n is at least two, two or more subsets of one or more label extenders, and a label probe system comprising a label. Each subset of n capture extenders is capable of hybridizing to one of the nucleic acids of interest, and the capture extenders in each subset are capable of hybridizing to one of the capture probes and thereby associating each subset of n capture extenders with a selected position on the solid support.

The composition optionally includes a sample comprising or suspected of comprising at least one of the nucleic acids of interest, e.g., two or more, three or more, etc. nucleic acids. In one class of embodiments, the composition includes at least a first nucleic acid of interest and is maintained at a hybridization temperature. The first nucleic acid of interest is hybridized to a first subset of n first capture extenders, which first capture extenders are hybridized to a first capture probe; the first nucleic acid is thereby associated with a first selected position on the solid support. It will be evident that the composition optionally includes second, third, etc. nucleic acids of interest, which are likewise associated with second, third, etc. selected positions on the solid support through association with second, third, etc. subsets of capture extenders and second, third, etc. capture probes. The hybridization temperature is greater than a melting temperature $T_m$ of a complex between each individual capture extender and its corresponding capture probe. The hybridization temperature is typically about 5° C. or more greater than the $T_m$, e.g., about 7° C. or more, about 10° C. or more, about 12° C. or more, about 15° C. or more, about 17° C. or more, or even about 20° C. or more greater than the $T_m$.

Essentially all of the features noted for the embodiments above apply to these embodiments as well, as relevant; for example, with respect to number of capture extenders per subset, type of solid support, composition of the label probe system, type of label, inclusion of blocking probes, configuration of the capture extenders, capture probes, label extenders, and/or blocking probes, number of nucleic acids of interest and of selected positions on the solid support, capture extenders and label extenders, source of the sample and/or nucleic acids, and/or the like.

Kits

Yet another general class of embodiments provides a kit for detecting two or more nucleic acids of interest. The kit includes two or more subsets of particles, two or more subsets of n capture extenders, wherein n is at least two, two or more subsets of one or more label extenders, and a label probe system comprising a label, packaged in one or more containers. A plurality of the particles in each subset are distinguishable from a plurality of the particles in every other subset. (Typically, substantially all of the particles in each subset are distinguishable from substantially all of the particles in every other subset.) The particles in each subset have associated therewith a different capture probe. Each subset of n capture extenders is capable of hybridizing to one of the nucleic acids of interest, and the capture extenders in each subset are capable of hybridizing to one of the capture probes and thereby associating each subset of n capture extenders with a selected subset of the particles. When the nucleic acid of interest corresponding to a subset of n capture extenders is hybridized to the subset of n capture extenders, which are hybridized to the corresponding capture probe, the nucleic acid of interest is hybridized to the subset of n capture extenders at a hybridization temperature which is greater than a melting temperature $T_m$ of a complex between each individual capture extender and the capture probe. The kit optionally also includes instructions for using the kit to capture and detect the nucleic acids of interest, one or more buffered solutions (e.g., lysis buffer, diluent, hybridization buffer, and/or wash buffer), standards comprising one or more nucleic acids at known concentration, and/or the like.

Essentially all of the features noted for the embodiments above apply to these embodiments as well, as relevant; for example, with respect to number of capture extenders per subset, composition of the label probe system, type of label, inclusion of blocking probes, configuration of the capture extenders, capture probes, label extenders, and/or blocking probes, number of nucleic acids of interest and of subsets of particles, capture extenders and label extenders, source of the sample and/or nucleic acids, and/or the like.

A related general class of embodiments provides a kit for detecting two or more nucleic acids of interest. The kit includes a solid support comprising two or more capture probes, each of which is provided at a selected position on the solid support, two or more subsets of n capture extenders, wherein n is at least two, two or more subsets of one or more label extenders, and a label probe system comprising a label, packaged in one or more containers. Each subset of n capture extenders is capable of hybridizing to one of the nucleic acids of interest, and the capture extenders in each subset are capable of hybridizing to one of the capture probes and thereby associating each subset of n capture extenders with a selected position on the solid support.

In one class of embodiments, when a nucleic acid of interest corresponding to a subset of n capture extenders is hybridized to the subset of n capture extenders, which are hybridized to the corresponding capture probe, the nucleic acid of interest is hybridized to the subset of n capture extenders at a hybridization temperature which is greater than a melting temperature $T_m$ of a complex between each individual capture extender and the capture probe. The hybridization temperature is typically about 5° C. or more greater than the $T_m$, e.g., about 7° C. or more, about 10° C. or more, about 12° C. or more, about 15° C. or more, about 17° C. or more, or even about 20° C. or more greater than the $T_m$.

The kit optionally also includes instructions for using the kit to capture and detect the nucleic acids of interest, one or more buffered solutions (e.g., lysis buffer, diluent, hybridization buffer, and/or wash buffer), standards comprising one or more nucleic acids at known concentration, and/or the like.

Essentially all of the features noted for the embodiments above apply to these embodiments as well, as relevant; for example, with respect to number of capture extenders per subset, composition of the label probe system, type of label, inclusion of blocking probes, configuration of the capture extenders, capture probes, label extenders, and/or blocking probes, number of nucleic acids of interest and of selected positions on the solid support, capture extenders and label extenders, source of the sample and/or nucleic acids, and/or the like.

Systems

In one aspect, the invention includes systems, e.g., systems used to practice the methods herein and/or comprising the compositions described herein. The system can include, e.g., a fluid and/or microsphere handling element, a fluid and/or microsphere containing element, a laser for exciting a fluorescent label and/or fluorescent microspheres, a detector for detecting light emissions from a chemiluminescent reaction or fluorescent emissions from a fluorescent label and/or fluorescent microspheres, and/or a robotic element that moves other components of the system from place to place as needed (e.g., a multiwell plate handling element). For example, in one class of embodiments, a composition of the invention is contained in a flow cytometer, a Luminex 100™ or HTS™ instrument, a microplate reader, a microarray reader, a luminometer, a colorimeter, or like instrument.

The system can optionally include a computer. The computer can include appropriate software for receiving user instructions, either in the form of user input into a set of parameter fields, e.g., in a GUI, or in the form of preprogrammed instructions, e.g., preprogrammed for a variety of different specific operations. The software optionally converts these instructions to appropriate language for controlling the operation of components of the system (e.g., for controlling a fluid handling element, robotic element and/or laser). The computer can also receive data from other components of the system, e.g., from a detector, and can interpret the data, provide it to a user in a human readable format, or use that data to initiate further operations, in accordance with any programming by the user.

Labels

A wide variety of labels are well known in the art and can be adapted to the practice of the present invention. For example, luminescent labels and light-scattering labels (e.g., colloidal gold particles) have been described. See, e.g., Csaki et al. (2002) "Gold nanoparticles as novel label for DNA diagnostics" Expert Rev Mol Diagn 2:187-93.

As another example, a number of fluorescent labels are well known in the art, including but not limited to, hydrophobic fluorophores (e.g., phycoerythrin, rhodamine, Alexa Fluor 488 and fluorescein), green fluorescent protein (GFP) and variants thereof (e.g., cyan fluorescent protein and yellow fluorescent protein), and quantum dots. See e.g., Haughland (2003) Handbook of Fluorescent Probes and Research Products, Ninth Edition or Web Edition, from Molecular Probes, Inc., or The Handbook: A Guide to Fluorescent Probes and Labeling Technologies, Tenth Edition or Web Edition (2006) from Invitrogen (available on the world wide web at probes.invitrogen.com/handbook) for descriptions of fluorophores emitting at various different wavelengths (including tandem conjugates of fluorophores that can facilitate simultaneous excitation and detection of multiple labeled species). For use of quantum dots as labels for biomolecules, see e.g., Dubertret et al. (2002) Science 298:1759; Nature Biotechnology (2003) 21:41-46; and Nature Biotechnology (2003) 21:47-51.

Labels can be introduced to molecules, e.g. polynucleotides, during synthesis or by postsynthetic reactions by techniques established in the art; for example, kits for fluorescently labeling polynucleotides with various fluorophores are available from Molecular Probes, Inc. ((www.) molecularprobes.com), and fluorophore-containing phosphoramidites for use in nucleic acid synthesis are commercially available. Similarly, signals from the labels (e.g., absorption by and/or fluorescent emission from a fluorescent label) can be detected by essentially any method known in the art. For example, multicolor detection, detection of FRET, fluorescence polarization, and the like, are well known in the art.

Microspheres

Microspheres are preferred particles in certain embodiments described herein since they are generally stable, are widely available in a range of materials, surface chemistries and uniform sizes, and can be fluorescently dyed. Microspheres can be distinguished from each other by identifying characteristics such as their size (diameter) and/or their fluorescent emission spectra, for example.

Luminex Corporation ((www.) luminexcorp.com), for example, offers 100 sets of uniform diameter polystyrene microspheres. The microspheres of each set are internally labeled with a distinct ratio of two fluorophores. A flow cytometer or other suitable instrument can thus be used to classify each individual microsphere according to its predefined fluorescent emission ratio. Fluorescently-coded microsphere sets are also available from a number of other suppliers, including Radix Biosolutions ((www.) radixbiosolutions.com) and Upstate Biotechnology ((www.) upstatebiotech.com). Alternatively, BD Biosciences ((www.) bd.com) and Bangs Laboratories, Inc. ((www.) bangslabs.com) offer microsphere sets distinguishable by a combination of fluorescence and size. As another example, microspheres can be distinguished on the basis of size alone, but fewer sets of such microspheres can be multiplexed in an assay because aggregates of smaller microspheres can be difficult to distinguish from larger microspheres.

Microspheres with a variety of surface chemistries are commercially available, from the above suppliers and others (e.g., see additional suppliers listed in Kellar and Iannone (2002) "Multiplexed microsphere-based flow cytometric assays" Experimental Hematology 30:1227-1237 and Fitzgerald (2001) "Assays by the score" The Scientist 15[11]:25). For example, microspheres with carboxyl, hydrazide or maleimide groups are available and permit covalent coupling of molecules (e.g., polynucleotide capture probes with free amine, carboxyl, aldehyde, sulfhydryl or other reactive groups) to the microspheres. As another example, microspheres with surface avidin or streptavidin are available and can bind biotinylated capture probes; similarly, microspheres coated with biotin are available for binding capture probes conjugated to avidin or streptavidin. In addition, services that couple a capture reagent of the customer's choice to microspheres are commercially available, e.g., from Radix Biosolutions ((www.) radixbiosolutions.com).

Protocols for using such commercially available microspheres (e.g., methods of covalently coupling polynucleotides to carboxylated microspheres for use as capture probes, methods of blocking reactive sites on the microsphere surface that are not occupied by the polynucleotides, methods of binding biotinylated polynucleotides to avidin-functionalized microspheres, and the like) are typically supplied with the microspheres and are readily utilized and/or adapted by one of skill. In addition, coupling of reagents to microspheres is well described in the literature. For example, see Yang et al. (2001) "BADGE, Beads Array for the Detection of Gene Expression, a high-throughput diagnostic bioassay" Genome Res. 11:1888-98; Fulton et al. (1997) "Advanced multiplexed analysis with the FlowMetrix™ system" Clinical Chemistry 43:1749-1756; Jones et al. (2002) "Multiplex assay for detection of strain-specific antibodies against the two variable regions of the G protein of respiratory syncytial virus" 9:633-638; Camilla et al. (2001) "Flow cytometric microsphere-based immunoassay: Analysis of secreted cytokines in whole-blood samples from asthmatics" Clinical and Diagnostic Laboratory Immunology 8:776-784; Martins (2002) "Development of internal controls for the Luminex instrument as part of a multiplexed seven-analyte viral respiratory antibody profile" Clinical and Diagnostic Laboratory Immunology 9:41-45; Kellar and Iannone (2002) "Multiplexed microsphere-based flow cytometric assays" Experimental Hematology 30:1227-1237; Oliver et al. (1998) "Multiplexed analysis of human cytokines by use of the FlowMetrix system" Clinical Chemistry 44:2057-2060; Gordon and McDade (1997) "Multiplexed quantification of human IgG, IgA, and IgM with the FlowMetrix™ system" Clinical Chemistry 43:1799-1801; U.S. Pat. No. 5,981,180 entitled "Multiplexed analysis of clinical specimens apparatus and methods" to Chandler et al. (Nov. 9, 1999); U.S. Pat. No. 6,449,562 entitled "Multiplexed analysis of clinical specimens apparatus and methods" to Chandler et al. (Sep. 10, 2002); and references therein.

Methods of analyzing microsphere populations (e.g. methods of identifying microsphere subsets by their size and/or fluorescence characteristics, methods of using size to distinguish microsphere aggregates from single uniformly sized microspheres and eliminate aggregates from the analysis, methods of detecting the presence or absence of a fluorescent label on the microsphere subset, and the like) are also well described in the literature. See, e.g., the above references.

Suitable instruments, software, and the like for analyzing microsphere populations to distinguish subsets of microspheres and to detect the presence or absence of a label (e.g., a fluorescently labeled label probe) on each subset are commercially available. For example, flow cytometers are widely available, e.g., from Becton-Dickinson ((www.) bd.com) and Beckman Coulter ((www.) beckman.com). Luminex 100™ and Luminex HTS™ systems (which use microfluidics to align the microspheres and two lasers to excite the microspheres and the label) are available from Luminex Corporation ((www.) luminexcorp.com); the similar Bio-Plex™ Protein Array System is available from Bio-Rad Laboratories, Inc. ((www.) bio-rad.com). A confocal microplate reader suitable for microsphere analysis, the FMAT™ System 8100, is available from Applied Biosystems ((www.) appliedbiosystems.com).

As another example of particles that can be adapted for use in the present invention, sets of microbeads that include optical barcodes are available from CyVera Corporation ((www.) cyvera.com). The optical barcodes are holographically inscribed digital codes that diffract a laser beam incident on the particles, producing an optical signature unique for each set of microbeads.

Molecular Biological Techniques

In practicing the present invention, many conventional techniques in molecular biology, microbiology, and recombinant DNA technology are optionally used. These techniques are well known and are explained in, for example, Berger and Kimmel, Guide to Molecular Cloning Techniques, Methods in Enzymology volume 152 Academic Press, Inc., San Diego, Calif.; Sambrook et al., Molecular Cloning—A Laboratory Manual (3rd Ed.), Vol. 1-3, Cold Spring Harbor Laboratory, Cold Spring Harbor, N.Y., 2000 and Current Protocols in Molecular Biology, F. M. Ausubel et al., eds., Current Protocols, a joint venture between Greene Publishing Associates, Inc. and John Wiley & Sons, Inc., (supplemented through 2005). Other useful references, e.g. for cell isolation and culture (e.g., for subsequent nucleic acid or protein isolation) include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (Eds.) (1995) Plant Cell, Tissue and Organ Culture; Fundamental Methods Springer Lab Manual, Springer-Verlag (Berlin Heidelberg New York) and Atlas and Parks (Eds.) The Handbook of Microbiological Media (1993) CRC Press, Boca Raton, Fla.

Making Polynucleotides

Methods of making nucleic acids (e.g., by in vitro amplification, purification from cells, or chemical synthesis), methods for manipulating nucleic acids (e.g., by restriction enzyme digestion, ligation, etc.) and various vectors, cell lines and the like useful in manipulating and making nucleic acids are described in the above references. In addition, methods of making branched polynucleotides (e.g., amplification multimers) are described in U.S. Pat. No. 5,635,352, U.S. Pat. No. 5,124,246, U.S. Pat. No. 5,710,264, and U.S. Pat. No. 5,849,481, as well as in other references mentioned above.

In addition, essentially any polynucleotide (including, e.g., labeled or biotinylated polynucleotides) can be custom or standard ordered from any of a variety of commercial sources, such as The Midland Certified Reagent Company ((www.) mcrc.com), The Great American Gene Company ((www.) genco.com), ExpressGen Inc. ((www.) expressgen.com), Qiagen (oligos.qiagen.com) and many others.

A label, biotin, or other moiety can optionally be introduced to a polynucleotide, either during or after synthesis. For example, a biotin phosphoramidite can be incorporated during chemical synthesis of a polynucleotide. Alternatively, any nucleic acid can be biotinylated using techniques known in the art; suitable reagents are commercially available, e.g., from Pierce Biotechnology ((www.) piercenet.com). Similarly, any nucleic acid can be fluorescently labeled, for example, by using commercially available kits such as those from Molecular Probes, Inc. ((www.) molecularprobes.com) or Pierce Biotechnology ((www.) piercenet.com) or by incorporating a fluorescently labeled phosphoramidite during chemical synthesis of a polynucleotide.

Arrays

In an array of capture probes on a solid support (e.g., a membrane, a glass or plastic slide, a silicon or quartz chip, a plate, or other spatially addressable solid support), each capture probe is typically bound (e.g., electrostatically or covalently bound, directly or via a linker) to the support at a unique selected location. Methods of making, using, and analyzing such arrays (e.g., microarrays) are well known in the art. See, e.g., Baldi et al. (2002) DNA Microarrays and Gene Expression: From Experiments to Data Analysis and Modeling, Cambridge University Press; Beaucage (2001) "Strategies in the preparation of DNA oligonucleotide arrays for diagnostic applications" Curr Med Chem 8:1213-1244; Schena, ed. (2000) Microarray Biochip Technology, pp. 19-38, Eaton Publishing; technical note "Agilent SurePrint Technology: Content centered microarray design enabling speed and flexibility" available on the web at chem.agilent-.com/temp/rad01539/00039489.pdf; and references therein. Arrays of pre-synthesized polynucleotides can be formed (e.g., printed), for example, using commercially available instruments such as a GMS 417 Arrayer (Affymetrix, Santa Clara, Calif.). Alternatively, the polynucleotides can be synthesized at the selected positions on the solid support; see, e.g., U.S. Pat. No. 6,852,490 and U.S. Pat. No. 6,306,643, each to Gentanlen and Chee entitled "Methods of using an array of pooled probes in genetic analysis."

Suitable solid supports are commercially readily available. For example, a variety of membranes (e.g., nylon, PVDF, and nitrocellulose membranes) are commercially available, e.g., from Sigma-Aldrich, Inc. ((www.) sigmaaldrich.com). As another example, surface-modified and pre-coated slides with a variety of surface chemistries are commercially available, e.g., from TeleChem International ((www.) arrayit-.com), Corning, Inc. (Corning, N.Y.), or Greiner Bio-One, Inc. ((www.) greinerbiooneinc.com). For example, silanated and silyated slides with free amino and aldehyde groups, respectively, are available and permit covalent coupling of molecules (e.g., polynucleotides with free aldehyde, amine, or other reactive groups) to the slides. As another example, slides with surface streptavidin are available and can bind biotinylated capture probes. In addition, services that produce arrays of polynucleotides of the customer's choice are commercially available, e.g., from TeleChem International ((www.) arrayit.com) and Agilent Technologies (Palo Alto, Calif.).

Suitable instruments, software, and the like for analyzing arrays to distinguish selected positions on the solid support and to detect the presence or absence of a label (e.g., a fluorescently labeled label probe) at each position are commercially available. For example, microarray readers are available, e.g., from Agilent Technologies (Palo Alto, Calif.), Affymetrix (Santa Clara, Calif.), and Zeptosens (Switzerland).

EXAMPLES

It is understood that the examples and embodiments described herein are for illustrative purposes only and that various modifications or changes in light thereof will be suggested to persons skilled in the art and are to be included within the spirit and purview of this application and scope of the appended claims. Accordingly, the following examples are offered to illustrate, but not to limit, the claimed invention.

Example 1

A Multiplex Branched DNA Assay for Parallel Quantitative Gene Expression Profiling The following sets forth a series of experiments that demonstrate detection of nucleic acids using a multiplex bDNA assay, in which the nucleic acids are captured to distinct subsets of microspheres through cooperative hybridization. This example describes a new method to quantitatively measure the expression of multiple mRNAs directly from crude cell lysates and tissue homogenates without the need for RNA purification or target amplification. A distinguishing feature of this multiplex bDNA assay is the use of cooperative hybridization (a strong, stable hybridization interaction formed by the collective force of multiple weak, unstable hybridization interactions) in the assay design, which ensures an exceptionally high degree of assay specificity. The experiments demonstrate that the assay is capable of detecting a single transcript of mRNA per cell from as few as 25,000 cells and with intra-plate and inter-plate coefficients of variance (CV) of less than 10% and 15%, respectively. To demonstrate the utility of this technology, several 10-plex (ten-gene) panels were developed to quantify the expression of genes involved in the proinflammatory and apoptosis stimulation pathways. The data from the multiplex bDNA assay was compared with that of single-plex bDNA assays with a high degree of correlation. The multiplex bDNA assay thus provides a powerful means to quantify the gene expression profile of a defined set of target genes in large sample populations.

As described above, the branched DNA (bDNA) assay provides a useful approach for the quantification of mRNA transcripts. A significant departure from target amplification methods, the bDNA assay can directly measure mRNA from crude cell lysates and tissue homogenates by amplifying the reporter signal, and thus avoiding the errors inherent in the extraction and amplification of target sequences. Owing to its robustness and precision, the bDNA assay has been used in clinical diagnostic applications such as viral load determination, and in drug discovery research studying drug metabolism, structure-activity relationships, high throughput screens, and more recently, siRNA knockdown analysis (Urdea et al. (1991) "Branched DNA amplification multimers for the sensitive, direct detection of human hepatitis virus" Nuc Acids Symp Ser 24:197-200, Gleaves et al. (2002) "Multi-center evaluation of the Bayer VERSANT HIV-1 RNA 3.0 assay: analytical and clinical performance" J Clin Virol. 25:205-16, Hartley and Klaassen (2000) "Detection of chemical-induced differential expression of rat hepatic cytochrome P450 mRNA transcripts using branched DNA signal amplification technology" Drug Metab Dispos. 28:608-16, Bramlett et al. (2000) "Correlation of farnesoid X receptor coactivator recruitment and cholesterol 7alpha-hydroxylase gene repression by bile acids" Mol Genet Metab. 71:609-15, and Warrior et al. (2000) "Application of QuantiGene nucleic acid quantification technology for high throughput screening" J Biomol Screen. 5:343-52, and Soutschek et al. (2004) "Therapeutic silencing of an endogenous gene by systemic administration of modified siRNAs" Nature 432:173-8).

The Luminex bead-based array system has been used in a wide range of multiplex applications throughout the drug-discovery and diagnostics fields, as well as basic research (Iannone (2000) "Multiplexed single nucleotide polymorphism genotyping by oligonucleotide ligation and flow cytometry" Cytometry 39:131-40, Yang et al. (2001) "BADGE, Beads Array for the Detection of Gene Expression, a high-throughput diagnostic bioassay" Genome Res. 11:1888-98, and Fulton et al. (1997) "Advanced multiplexed analysis with the FlowMetrix system" Clin Chem. 43:1749-56). For example, it has been a widely adopted platform for quantitative multiplex protein expression analysis. At the core are 100 fluorescent-encoded microsphere beads that can be coupled with a capture reagent specific to a particular bioassay, allowing for the detection of up to 100 unique analytes within a single sample.

A multiplex bDNA assay has been developed that combines the advantages of the conventional single-plex bDNA assay with, e.g., the multiplex capability of the Luminex platform. The fluorescent beads are coupled with a set of oligonucleotide capture probes, and cooperative hybridization is exploited in the assay design for exceptionally high assay specificity. The new mRNA quantification method measures the expression levels of multiple mRNA transcripts quantitatively from purified RNA and crude cell lysates with high accuracy and reproducibility. The simplicity and data quality of the assay makes it an ideal tool for high throughput parallel quantitative gene expression analysis.

Results

Overview of the Multiplex bDNA Assay

Figure 5A:
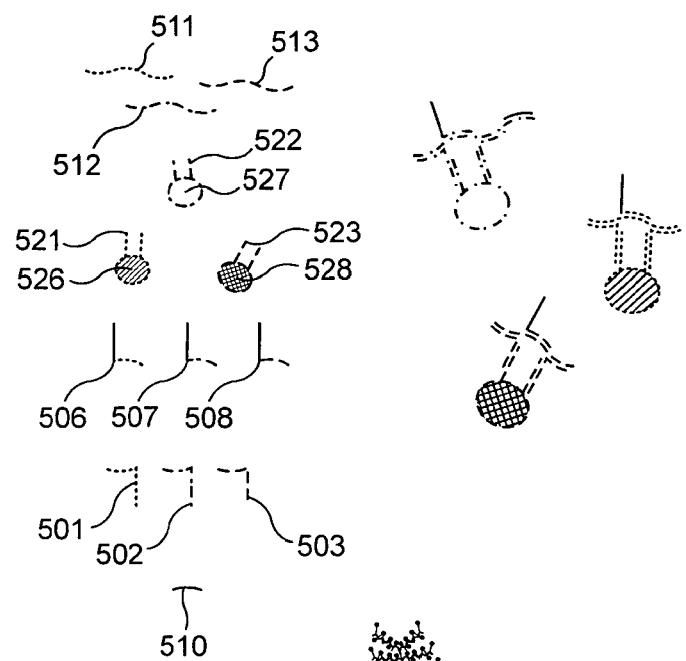
FIG. 5 Panels A-C schematically depict an overview of a multiplex bDNA assay.
Figure 5B:
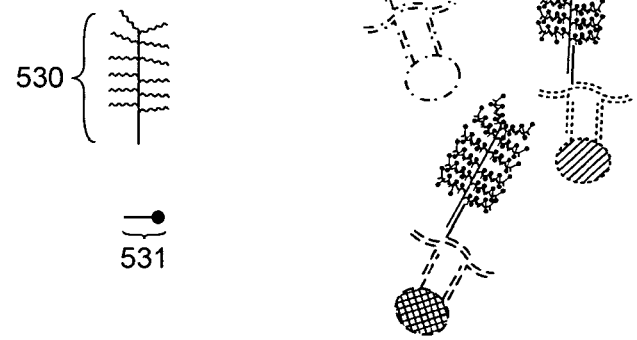
Figure 5C:
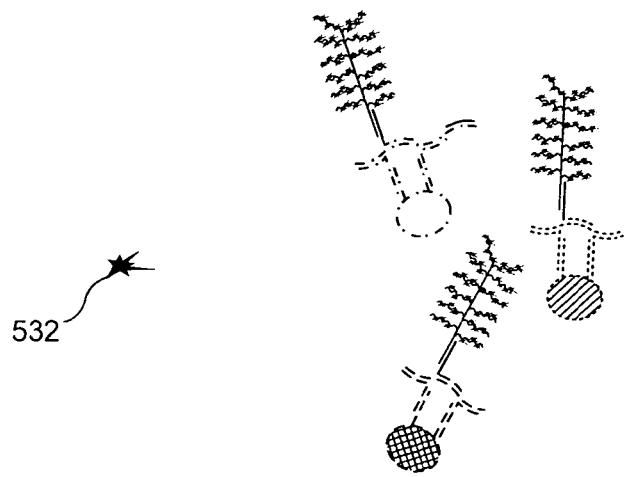
Figure 7A:
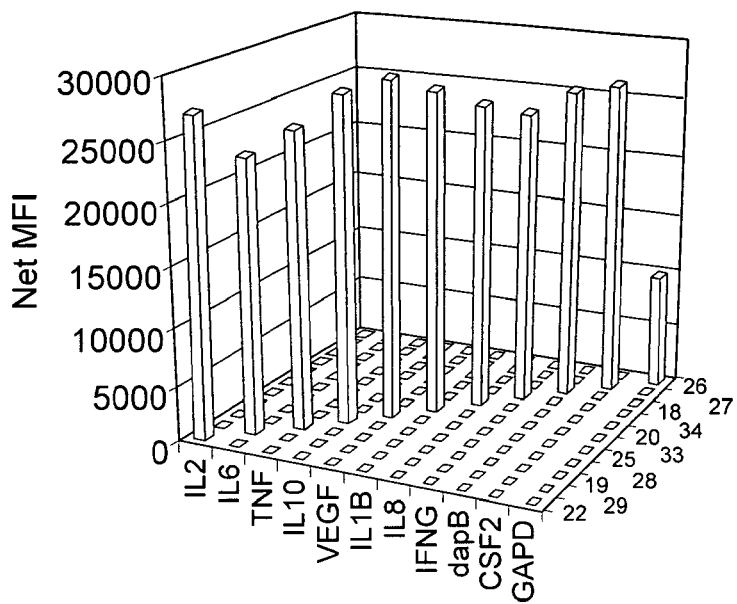
FIG. 7 Panel A depicts a graph illustrating evaluation of the cytokine panel for cross-reactivity. Individual mRNA transcript names are presented on the x-axis, bead subsets are identified by number on the y-axis, and fluorescent signal is graphed on the z-axis. Panel B depicts a line graph of fluorescent intensity observed for a dilution series of dapB transcript in the presence (squares) or absence (diamonds) of 0.2 μg total RNA, for evaluation of specificity. Panel C depicts a line graph of fluorescent intensity observed for a dilution series of IL10 transcript in the presence (squares) or absence (diamonds) of 0.2 μg total RNA, for evaluation of specificity. Panel D depicts a line graph of fluorescent intensity for a dilution series of all the transcripts in the cytokine panel, for evaluation of assay sensitivity and dynamic range.
Figure 7B:
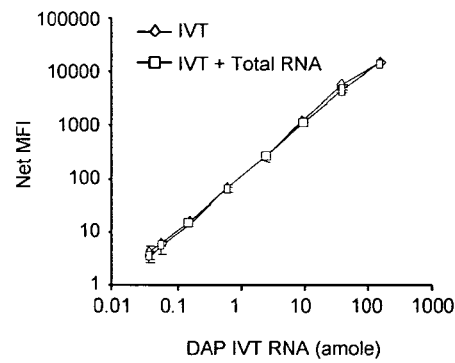
Figure 7C:
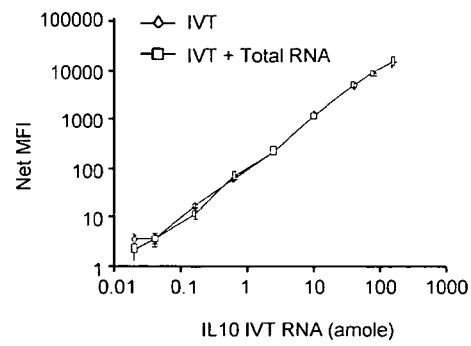
Figure 7D:
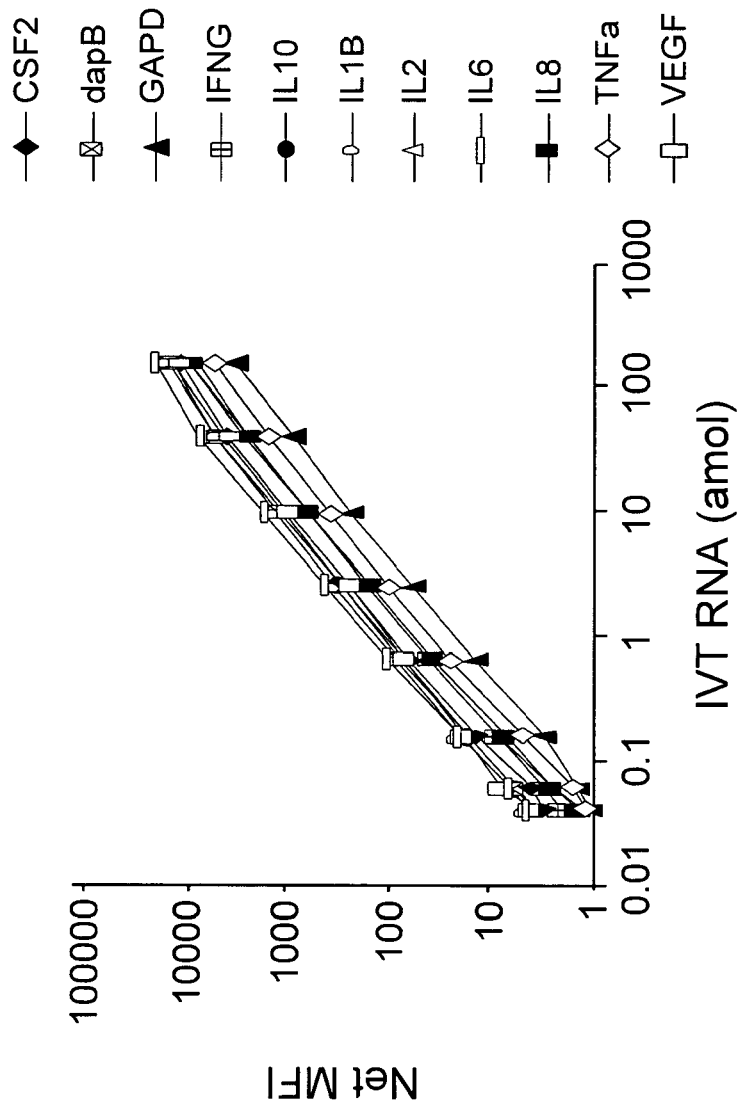

In the multiplex bDNA assay, fluorescent-encoded microsphere beads (Luminex Corporation) were used for the capture of specific mRNA species (FIG. 5 Panels A-C). The ability to quantify multiple mRNA transcripts lies in the design of a probe set for each mRNA transcript of interest. A probe set contains three types of synthetic oligonucleotide probes called capture extenders (CEs, 501-503), label extenders (LEs, 506-508), and blockers (BPs, 510) that hybridize and span a contiguous region of the target mRNA (511-513, provided for example in a cell lysate or tissue homogenate). The intended target is captured by multiple CEs, which hybridize specifically to their complementary capture probes (CPs, 521-523) bound to the fluorescent-encoded beads (526-528) and allow the target mRNA to be captured to its corresponding beads. Signal amplification occurs when the LE tails are hybridized with a branched DNA molecule (bDNA amplifier, 530), which can then be hybridized with biotinylated label probes (531) followed by streptavidin-conjugated phycoerythrin (SAPE, 532). Bead fluorescent color codes and SAPE reporter signals from all beads in the final hybridization mixture are determined using a Luminex flow cytometer (or similar instrument), which maps each bead to a specific mRNA assay and provides a fluorescence measurement of SAPE reporter associated with that bead. The SAPE signals are proportional to the number of mRNA transcripts captured to the beads.

The assay includes three major steps: (1) Capture of the specific mRNA transcripts to their corresponding beads through CE-CP interaction during an overnight hybridization at 53° C. (FIG. 5 Panel A); (2) Hybridization with the bDNA amplification molecule and biotinylated label probe, respectively, for an hour at 46° C. (FIG. 5 Panel B); and (3) Hybridization with streptavidin-conjugated R-phycoerythrin (SAPE) at room temperature for 30 minutes (FIG. 5 Panel C). The Luminex beads are then analyzed with a Luminex 100™ system. The level of SAPE fluorescence measured from each bead is proportional to the amount of mRNA transcript captured by the bead.

Cooperative Hybridization

When the melting temperature ($T_m$) of an oligonucleotide duplex (e.g., a CP-CE hybridization interaction) is below the actual hybridization temperature, dissociation to its single-stranded form is favored under the assay condition. Such single hybridization does not result in stable capture of the target mRNA under this condition. However, when multiple weak hybridization interactions exist, the collective force of these weak hybridization allows the stable capture of the target mRNA. FIG. 6 Panels A and B depict simple and cooperative hybridization, respectively. Simple hybridization between a CP and CE under the standard bDNA assay conditions is illustrated by the results shown in FIG. 6 Panel C. CP14, CP15, and CP16 represent capture probes where the complementary sequence between CP and CE are 14, 15, or 16 bases in length, respectively. CP-N represents a nonspecific capture probe that does not hybridize with the CE sequence. The CE-LE represents a probe that can bind to the CP at one end and the bDNA amplification molecule at the other end. The CE represents a probe that binds to CP only but not the bDNA amplification molecule. Cooperative hybridization between CP and CE under the standard bDNA assay conditions is illustrated by the results shown in FIG. 6 Panel D. A standard single-plex bDNA assay on IL-6 IVT RNA dilution series was performed in assay plate wells where CP14, CP15, or CP16 was attached to the surface, respectively. RLU stands for the Relative Luminescent Unit and the error bars represent 1 s.d.

A strong, stable hybridization interaction can be produced through the joint force of multiple weak, unstable hybridization interactions. The weak, unstable hybridization interaction occurs when the melting temperature ($T_m$) of the hybridizing nucleic acids is below the assay temperature. This concept is termed cooperative hybridization. Cooperative hybridization can be applied in bDNA assays to allow highly specific capture of target mRNA. When simple hybridization (FIG. 6 Panel A) between the CE and the CP occurs at a temperature above their melting temperature, the target mRNA cannot be stably captured to the solid surface. However, when multiple of those weak CE-CP hybridizations occur at the same time (FIG. 6 Panel B), the target mRNA can be stably captured to the solid surface. To demonstrate cooperative hybridization, three capture probes varying in length from 14mer to 16mer were designed and used in a plate-based, single-plex bDNA assay. The 14 to 16 base capture probes were chosen because the melting temperature ($T_m$) is below the hybridization temperature of the bDNA assay, which is at 53° C. The simple hybridization between the CP and the CE was evaluated through an oligonucleotide (CE-LE) that contains a CE tail sequence complementary to the capture probe and an LE tail sequence complementary to a sequence in the bDNA amplifier molecule. A strong assay signal is obtained when the capture probe is 16 bases in length, a 100-fold weaker hybridization interaction is evident when the capture probe is 15 bases in length, and minimal hybridization interaction occurs when the capture probe is 14 bases in length (FIG. 6 Panel C). When the three capture probes were used respectively in a bDNA assay where multiple CEs were present, overlapping assay signal was obtained regardless of capture probe length (FIG. 6 Panel D). This suggests that cooperative hybridization plays a prominent role in the bDNA assay, especially when the capture probe is 14 bases long.

Using the cooperative hybridization concept, a set of capture probes that work together in a single hybridization reaction with minimal nonspecific cross-hybridization was designed. The capture probes were designed to comprise unique 15mer DNA sequences and a common linker that allows them to be chemically cross-linked onto the surface of the different fluorescent-encoded bead populations. Each bead population was examined for specific hybridization to its complementary biotinylated oligonucleotide as well as for its non-specific hybridization to the other biotinylated oligonucleotides. The assay signals of all possible non-specific hybridizations were less than 0.1% of those observed for the perfectly matched pair, indicating a very high degree of hybridization specificity. Thus the set of capture probes was shown to be highly specific and can be used in the multiplex bDNA assay for the capture of target mRNA.

Performance Evaluation of Multiplex bDNA Assay

To demonstrate the performance of the multiplex bDNA assay, several 10-plex panels were developed (three of which are described in Table 1) and evaluated for sensitivity, linear dynamic range, precision and specificity using in vitro transcribed (IVT) RNA transcripts as reference standards. The performance evaluation data for the cytokine panel (FIG. 7 and Table 2) is below. Probe sets for the cytokine panel are listed in Table 3.

To determine the cross-reactivity between target mRNAs, 40 amol of each IVT RNA transcript was individually hybridized into the bead array followed by measurement of signals for the intended target as well as for other genes. Cross-reactivity is expressed as the percentage of the average signal for other genes over the signal for the intended target. When 40 amol of individual mRNA transcripts (represented by gene name on the x-axis of FIG. 7 Panel A) was added into the fluorescent-encoded bead array, only the corresponding bead (represented by number on the y-axis) gives a strong fluorescent signal (z-axis). Net MFI stands for background subtracted median fluorescent intensity from 100 counted beads. The cross-reactivity between target genes in the panel was less than 0.1%, suggesting minimal cross hybridization between the genes in the panel (FIG. 7 Panel A and Table 2).

The assay specificity was evaluated by measuring the signal of *B. subtilis* dapB IVT RNA, which has little homology with human RNA, and human IL10 IVT RNA, which has undetectable expression in human U937 cells, as model genes. The IVT RNA transcripts of dapB and IL10 were serially diluted four-fold from 160 to 0.04 amol and mixed with 0.2 μg of total RNA extracted from human U937 cells. A multiplex bDNA assay was performed and the assay signals for dapB (FIG. 7 Panel B) and IL10 (FIG. 7 Panel C) were compared in the presence (squares) or absence (diamonds) of the U937 total RNA background. Overlapping signals were observed through the entire dilution series for both dapB and IL10, suggesting that minimal nonspecific hybridization occurred. Importantly, the addition of 0.2 μg of total RNA did not increase the assay background, further demonstrating the assay specificity. Tests that determine spike recovery of a target from a complex mixture are a typically recommended analytical procedure to assess assay accuracy. The assay is considered reliable if the signal difference between pure and spiked-in analyte is within ±20%. In this case, no change in assay signal was observed in the presence of U937 total RNA, indicating that nonspecific RNA does not seem to interfere with the hybridization of the target RNA to the capture beads. As a result, IVT RNA standard curves can be used to quantify the absolute number of copies of RNA transcripts in a sample.

To determine the assay sensitivity and linear dynamic range, ten target IVT RNA transcripts were equally mixed and serially diluted four-fold to generate standard curves with target RNA levels ranging from $2.4 \times 10^4$ to $9.6 \times 10^7$ transcripts (0.04 to 160 amol). The signal responses for all the cytokine genes were linear across the target concentration range examined with coefficients of correlation ($R^2$) averaged 0.99, indicating that the linear dynamic range of the assay spans more than 3 logs (FIG. 7 Panel D). The sensitivity of the assay was evaluated by determining the limit of detection (LOD) for each target RNA. LOD, defined as the target concentration at which the signal is three standard deviations above the background, is 0.06 amol for VEGF and 0.04 amol for the remaining cytokines (Table 2).

Assay precision between different wells (intra-plate) and between assays performed on different days (inter-plate) was assessed by calculating coefficients of variation (% CV) for each gene expression measurement from 0.04-160 amol IVT across multiple samples. Precision value for each gene was measured across multiple wells within a single plate (n=4) and across multiple plates (N=3). Intra-plate CV averaged about 8%, ranging from 5 to 14%, and inter-plate CV averaged about 14%, ranging from 7% to 22% (Table 2). Average intra-plate CV of less than 10% has been routinely obtained for multiplex bDNA assays with triplicate samples. It should be noted that the CVs were highly comparable from high to low concentrations of the target IVT RNA tested, suggesting that accurate quantification can be achieved in a target concentration-independent fashion.

TABLE 1

Target names and reference sequence accession numbers for the cytokine and apoptosis 10-plex panels.

| Bead Number | Cytokine Panel | | Apoptosis Panel 1 | | Apoptosis Panel 2 | |
|---|---|---|---|---|---|---|
| | Target Symbol | Accession Number | Target Symbol | Accession Number | Target Symbol | Accession Number |
| 22 | IL2 | NM_000586 | RELB | NM_006509 | BAK1 | NM_001188 |
| 29 | TNF | NM_000594 | TNF | NM_000594 | TNFSF6 | NM_000639 |
| 19 | VEGF | NM_003376 | NFKB2 | NM_002502 | IL6R | NM_000565 |
| 28 | IL10 | NM_000572 | TNFAIP3 | NM_006290 | TNFRSF6 | NM_000043 |
| 25 | IL6 | NM_000600 | IL6 | NM_000600 | PTK2B | NM_004103 |
| 33 | IL1B | NM_000576 | CDKN1A | NM_000389 | BAD | NM_004322 |
| 20 | IFNG | NM_000619 | NFKB1 | NM_003998 | BCL2 | NM_000633 |
| 18 | IL8 | NM_000584 | RELA | NM_021975 | BCL2L1 | NM_138578 |
| 27 | CSF2 | NM_000758 | NFKBIA | NM_020529 | CFLAR | NM_003879 |
| 26 | GAPD | NM_002046 | GAPD | NM_002046 | ACTB | NM_001101 |
| 34 | dapB | L38424 | N/A | N/A | N/A | N/A |

TABLE 2

Detection sensitivity, cross-reactivity, and assay background of the cytokine 10-plex panel.

| Gene | CSF2 | GAPD | IFNG | IL10 | IL1B | IL2 | IL6 | IL8 | TNF | VEGF | dapB |
|---|---|---|---|---|---|---|---|---|---|---|---|
| LOD (amol) | 0.04 | 0.04 | 0.04 | 0.04 | 0.04 | 0.04 | 0.04 | 0.04 | 0.04 | 0.06 | 0.04 |
| % Cross-reactivity* | 0.004% | 0.003% | 0.006% | 0.007% | 0.004% | 0.006% | 0.018% | 0.100% | 0.002% | 0.139% | 0.018% |
| Average background (MFI) | 2.4 | 2.3 | 1.9 | 3.6 | 3.7 | 1.9 | 2.0 | 1.1 | 3.0 | 15.9 | 5.5 |
| % Intra-plate CV | 9% | 8% | 8% | 7% | 7% | 5% | 8% | 14% | 9% | 7% | 5% |
| % Inter-plate CV | 21% | 12% | 11% | 10% | 22% | 7% | 13% | 10% | 18% | 20% | 7% |

*Cross-reactivity is the percentage of signal generated by hybridization of mRNA to nontarget beads, in relation to the specific hybridization to its target bead (100%)

TABLE 3

Probe sets (CPs, CEs, LEs, and BPs) for the cytokine panel.

| Gene | | | SEQ ID NO |
|---|---|---|---|
| CSF2 | BP | GGGCTGGGCGAGCGG | 5 |
| CSF2 | BP | CCAGGGCTGCGTGCTG | 6 |
| CSF2 | BP | AGACGCCGGGCCTCC | 7 |
| CSF2 | BP | CCGCAGGCCCTGCTTG | 8 |
| CSF2 | BP | TCATGGTCAAGGGGCCCT | 9 |
| CSF2 | BP | GGGGTTGGAGGGCAGTGC | 10 |
| CSF2 | BP | CAGCAGTCAAAGGGGATGACA | 11 |
| CSF2 | LE | caggccacagtgcccaagTTTTTaggcataggacccgtgtct | 12 |
| CSF2 | LE | tggatggcattcacatgctcTTTTTaggcataggacccgtgtct | 13 |
| CSF2 | LE | gcagtgtctctactcaggttcaggTTTTTaggcataggacccgtgtct | 14 |
| CSF2 | LE | ttctactgtttcattcatctcagcaTTTTTaggcataggacccgtgtct | 15 |
| CSF2 | LE | ggaggtcaaacatttctgagatgacTTTTTaggcataggacccgtgtct | 16 |
| CSF2 | LE | tgtaggcaggtcggctcctTTTTTaggcataggacccgtgtct | 17 |
| CSF2 | LE | gggttgcacaggaagtttccTTTTTaggcataggacccgtgtct | 18 |
| CSF2 | LE | tttgaaactttcaaaggtgataatctTTTTTaggcataggacccgtgtct | 19 |
| CSF2 | LE | agcagaaagtccttcaggttctcTTTTTaggcataggacccgtgtct | 20 |
| CSF2 | LE | ctcactcctggactggctccTTTTTaggcataggacccgtgtct | 21 |
| CSF2 | CE | agcagcaggctctgcagcTTTTTttgtgcagtgttata | 22 |
| CSF2 | CE | gcgggtgcagagatgctgTTTTTttgtgcagtgttata | 23 |
| CSF2 | CE | tacagctccaggcgggtcTTTTTttgtgcagtgttata | 24 |
| CSF2 | CE | tgagcttggtgaggctgccTTTTTttgtgcagtgttata | 25 |
| CSF2 | CE | tgcttgtagtggctggccaTTTTTttgtgcagtgttata | 26 |
| CSF2 | CP | TTTTTTTTTATAACACTGCACAA | 27 |
| GAPD | BP | TCAGCGCCAGCATCGC | 28 |
| GAPD | BP | GAGGGGGCAGAGATGATGAC | 29 |
| GAPD | BP | AACATGGGGGCATCAGCA | 30 |
| GAPD | BP | CATGGTTCACACCCATGACG | 31 |

TABLE 3 -continued

Probe sets (CPs, CEs, LEs, and BPs) for the cytokine panel.

| Gene | | | SEQ ID NO |
|---|---|---|---|
| GAPD | BP | CGGAGGGGCCATCCAC | 32 |
| GAPD | BP | TGGAGAGCCCCGCGG | 33 |
| GAPD | BP | gcaggaggcattgctgatga | 34 |
| GAPD | LE | gatgggatttccattgatgacaTTTTTaggcataggacccgtgtct | 35 |
| GAPD | LE | cccacttgattttggagggaTTTTTaggcataggacccgtgtct | 36 |
| GAPD | LE | ccagtggactccacgacgtacTTTTTaggcataggacccgtgtct | 37 |
| GAPD | LE | ttctccatggtggtgaagacgTTTTTaggcataggacccgtgtct | 38 |
| GAPD | LE | tcttgaggctgttgtcatacttctTTTTTaggcataggacccgtgtct | 39 |
| GAPD | LE | gggtgctaagcagttggtggtTTTTTaggcataggacccgtgtct | 40 |
| GAPD | LE | ccttccacgataccaaagttgtTTTTTaggcataggacccgtgtct | 41 |
| GAPD | LE | ggcatggactgtggtcatgagtTTTTTaggcataggacccgtgtct | 42 |
| GAPD | LE | agtcttctgggtggcagtgatTTTTTaggcataggacccgtgtct | 43 |
| GAPD | LE | ccatcacgccacagtttccTTTTTaggcataggacccgtgtct | 44 |
| GAPD | LE | cagtagaggcagggatgatgttcTTTTTaggcataggacccgtgtct | 45 |
| GAPD | LE | cacagccttggcagcgcTTTTTaggcataggacccgtgtct | 46 |
| GAPD | LE | ccagtgagcttcccgttcaTTTTTaggcataggacccgtgtct | 47 |
| GAPD | CE | tgacggtgccatggaatttTTTTTaaaactatacgtgct | 48 |
| GAPD | CE | agcttcccgttctcagcctTTTTTaaaactatacgtgct | 49 |
| GAPD | CE | tctcgctcctggaagatggtTTTTTaaaactatacgtgct | 50 |
| GAPD | CE | gcaaatgagccccagccTTTTTaaaactatacgtgct | 51 |
| GAPD | CE | cctttggctccccctTTTTTaaaactatacgtgct | 52 |
| GAPD | CE | catggatgaccttggccagTTTTTaaaactatacgtgct | 53 |
| GAPD | CE | gctcagggatgaccttgccTTTTTaaaactatacgtgct | 54 |
| GAPD | CP | TTTTTTTTAGCACGTATAGTTTT | 55 |
| IFNG | BP | TGCATTAAAATATTTCTTAAGGTTTTCT | 56 |
| IFNG | BP | AAATGCCTAAGAAAAGAGTTCCA | 57 |
| IFNG | BP | AAAAGTTTGAAGTAAAAGGAGACAAT | 58 |
| IFNG | BP | GATGCTCTGGTCATCTTTAAAGTTTTT | 59 |
| IFNG | BP | GGATGCTCTTCGACCTTGAAAC | 60 |
| IFNG | BP | AATAAATAGATTTAGATTTAAAATTCAAATATT | 61 |
| IFNG | LE | gcttcttttacatatgggtcctggTTTTTaggcataggacccgtgtct | 62 |
| IFNG | LE | ttatccgctacatctgaatgaccTTTTTaggcataggacccgtgtct | 63 |
| IENG | LE | ttgatggtctccacactcttttgTTTTTaggcataggacccgtgtct | 64 |
| IFNG | LE | aaaaacttgacattcatgtcttccTTTTTaggcataggacccgtgtct | 65 |
| IFNG | LE | ataattagtcagcttttcgaagtcaTTTTTaggcataggacccgtgtct | 66 |
| IFNG | LE | tggacattcaagtcagttaccgaTTTTTaggcataggacccgtgtct | 67 |
| IFNG | LE | cgacagttcagccatcacttggTTTTTaggcataggacccgtgtct | 68 |

TABLE 3 -continued

Probe sets (CPs, CEs, LEs, and BPs) for the cytokine panel.

| Gene | | | SEQ ID NO |
|---|---|---|---|
| IFNG | LE | agcatctgactcctttttcgcTTTTTaggcataggacccgtgtct | 69 |
| IFNG | LE | gcaggcaggacaaccattactgTTTTTaggcataggacccgtgtct | 70 |
| IFNG | LE | aatacttatttgattgatgagtctaaaaatTTTTTaggcataggacccgtgtct | 71 |
| IFNG | CE | cactctcctctttccaattcttcaTTTTTTTtttcacacacattaac | 72 |
| IFNG | CE | ttggctctgcattattttttctgtTTTTTtttcacacacattaac | 73 |
| IFNG | CE | tctcgtttcttttttgttgctattgTTTTTtttcacacacattaac | 74 |
| IFNG | CE | atgagttcatgtattgctttgcgtTTTTTtttcacacacattaac | 75 |
| IFNG | CE | ttccctgttttagctgctggTTTTTtttcacacacattaac | 76 |
| IFNG | CE | atattccccatataaataatgttaaatattTTTTTtttcacacacattaac | 77 |
| IFNG | CP | TTTTTTTTGTTAATGTGTGTGAA | 78 |
| IL1 | BP | GGTAAAACTGGATCATCTCAGACAA | 79 |
| IL1 | BP | GGGGCATCACCTCCTCCA | 80 |
| IL1 | BP | GTTCACATGCGCCTTGATGT | 81 |
| IL1 | BP | GCTCTTGTTTTCACAGGGAAGA | 82 |
| IL1 | BP | GGCTTTGTAGATGCCTTTCTCT | 83 |
| IL1 | BP | gactgggtgccctggcc | 84 |
| IL1 | LE | TaggcaggttgcctgggaTTTTTaggcataggacccgtgtct | 85 |
| IL1 | LE | gtcttcactctgctgaaggcatTTTTTaggcataggacccgtgtct | 86 |
| IL1 | LE | actcctttaacaacaagttgtccaTTTTTaggcataggacccgtgtct | 87 |
| IL1 | LE | ccttaaagtcctccagcaaggTTTTTaggcataggacccgtgtct | 88 |
| IL1 | LE | ggcttggcaacccaggtaacTTTTTaggcataggacccgtgtct | 89 |
| IL1 | LE | caggttctcccccagggaTTTTTaggcataggacccgtgtct | 90 |
| IL1 | LE | aatcgatgacagcgccgtaTTTTTaggcataggacccgtgtct | 91 |
| IL1 | LE | cacctgctccacggccttTTTTTaggcataggacccgtgtct | 92 |
| IL1 | LE | tggagcttattaaaggcattcttTTTTTaggcataggacccgtgtct | 93 |
| IL1 | LE | tgatgaagatgtcaaactcactcatTTTTTaggcataggacccgtgtct | 94 |
| IL1 | LE | cattgtcatgtaggcttctatgtagtTTTTTaggcataggacccgtgtct | 95 |
| IL1 | LE | ccctgatgtctcagtttcgtatcttTTTTTaggcataggacccgtgtct | 96 |
| IL1 | LE | tgtcctagagtctatagagtcgccaTTTTTaggcataggacccgtgtct | 97 |
| IL1 | LE | gctatcccagagccccagatTTTTTaggcataggacccgtgtct | 98 |
| IL1 | CE | agtgggtgcagctgttctcaTTTTTccgtgcttttctaat | 99 |
| IL1 | CE | ctcggagatctcgaagcatgtTTTTTccgtgcttttctaat | 100 |
| IL1 | CE | gctgatccttcatttgaaagaaaTTTTTccgtgcttttctaat | 101 |
| IL1 | CE | ctgggtcttggttctcagcttTTTTTccgtgcttttctaat | 102 |
| IL1 | CE | gcctcagcctgagggtcttTTTTTccgtgcttttctaat | 103 |
| IL1 | CE | ccgattttggagacctctaatttaTTTTTccgtgcttttctaat | 104 |
| IL1 | CP | TTTTTTTTATTAGAAAAGCACGG | 105 |
| IL1B | BP | ACTGACGCGGCCTGCC | 106 |

TABLE 3 -continued

Probe sets (CPs, CEs, LEs, and BPs) for the cytokine panel.

| Gene | | | SEQ ID NO |
|---|---|---|---|
| IL1B | BP | ccagacatcaccaagcttttttt | 107 |
| IL1B | LE | gccatcagcttcaaagaacaagTTTTTaggcataggacccgtgtct | 108 |
| IL1B | LE | aaggagcacttcatctgtttaggTTTTTaggcataggacccgtgtct | 109 |
| IL1B | LE | atgccgccatccagaggTTTTTaggcataggacccgtgtct | 110 |
| IL1B | LE | ggtcggagattcgtagctggTTTTTaggcataggacccgtgtct | 111 |
| IL1B | LE | gcttgtccatggccacaacaTTTTTaggcataggacccgtgtct | 112 |
| IL1B | LE | gggaaccagcatcttcctcaTTTTTaggcataggacccgtgtct | 113 |
| IL1B | LE | ggttcttcttcaaagatgaagggTTTTTaggcataggacccgtgtct | 114 |
| IL1B | LE | ttatcccatgtgtcgaagaagataTTTTTaggcataggacccgtgtct | 115 |
| IL1B | LE | catcgtgcacataagcctcgTTTTTaggcataggacccgtgtct | 116 |
| IL1B | LE | gcagttcagtgatcgtacaggtgTTTTTaggcataggacccgtgtct | 117 |
| IL1B | LE | gctgtgagtcccggagcgtTTTTTaggcataggacccgtgtct | 118 |
| IL1B | LE | atggagaacaccacttgttgctTTTTTaggcataggacccgtgtct | 119 |
| IL1B | LE | actttcttctccttgtacaaaggacTTTTTaggcataggacccgtgtct | 120 |
| IL1B | LE | aggccacaggtattttgtcattTTTTTaggcataggacccgtgtct | 121 |
| IL1B | CE | gcagaggtccaggtcctggTTTTTaacgtgtattccatt | 122 |
| IL1B | CE | tgaagcccttgctgtagtggtTTTTTaacgtgtattccatt | 123 |
| IL1B | CE | cctggaaggtctgtgggcaTTTTTaacgtgtattccatt | 124 |
| IL1B | CE | aaagaaggtgctcaggtcattctTTTTTaacgtgtattccatt | 125 |
| IL1B | CE | ggagagctttcagttcatatggaTTTTTaacgtgtattccatt | 126 |
| IL1B | CE | ccatatcctgtccctggaggtTTTTTaacgtgtattccatt | 127 |
| IL1B | CE | attcttttccttgagggcccaTTTTTaacgtgtattccatt | 128 |
| IL1B | CP | TTTTTTTTAATGGAATACACGTT | 129 |
| IL2 | BP | TTCCATTCAAAATCATCTGTAAATC | 130 |
| IL2 | BP | CCTGGGTCTTAAGTGAAAGTTTTT | 131 |
| IL2 | BP | AGCATATTCACACATGAATGTTGTT | 132 |
| IL2 | BP | AAAAGGTAATCCATCTGTTCAGAAA | 133 |
| IL2 | BP | ATTCAACAATAAATATAAAATTTAAATATTTA | 134 |
| IL2 | LE | agtaggtgcactgtttgtgacaagTTTTTaggcataggacccgtgtct | 135 |
| IL2 | LE | gctgtgttttctttgtagaacttgaTTTTTaggcataggacccgtgtct | 136 |
| IL2 | LE | cagcagtaaatgctccagttgtaTTTTTaggcataggacccgtgtct | 137 |
| IL2 | LE | aaacttaaatgtgagcatcctggTTTTTaggcataggacccgtgtct | 138 |
| IL2 | LE | tagacactgaagatgtttcagttctgTTTTTaggcataggacccgtgtct | 139 |
| IL2 | LE | gctttgagctaaatttagcacttcTTTTTaggcataggacccgtgtct | 140 |
| IL2 | LE | attacgttgatattgctgattaagtcTTTTTaggcataggacccgtgtct | 141 |
| IL2 | LE | ttctacaatggttgctgtctcatcTTTTTaggcataggacccgtgtct | 142 |
| IL2 | LE | tcagtgttgagatgatgctttgacTTTTTaggcataggacccgtgtct | 143 |

TABLE 3 -continued

Probe sets (CPs, CEs, LEs, and BPs) for the cytokine panel.

| Gene | | | SEQ ID NO |
|---|---|---|---|
| IL2 | LE | agtgggaagcacttaattatcaagTTTTTaggcataggacccgtgtct | 144 |
| IL2 | LE | aatagttacaataggtagcaaaccatacTTTTTaggcataggacccgtgtct | 145 |
| IL2 | CE | tgagtttgggattcttgtaattattaaTTTTTgaagttaccgttttc | 146 |
| IL2 | CE | tggccttcttgggcatgtaTTTTTgaagttaccgttttc | 147 |
| IL2 | CE | ctccagaggtttgagttcttcttcTTTTTgaagttaccgttttc | 148 |
| IL2 | CE | tcagatccctttagttccagaactTTTTTgaagttaccgttttc | 149 |
| IL2 | CE | aataaatagaaggcctgatatgttttaTTTTTgaagttaccgttttc | 150 |
| IL2 | CP | TTTTTTTTGAAAACGGTAACTTC | 151 |
| IL6 | BP | TGGGGCAGGGAAGGCA | 152 |
| IL6 | BP | GGAATCTTCTCCTGGGGGTAC | 153 |
| IL6 | BP | TGGGGCGGCTACATCTTT | 154 |
| IL6 | BP | GCTTTCACACATGTTACTCTTGTTACA | 155 |
| IL6 | BP | TTTGGAAGGTTCAGGTTGTTTT | 156 |
| IL6 | BP | CCTCAAACTCCAAAAGACCAGTG | 157 |
| IL6 | BP | TTGGGTCAGGGGTGGTTATT | 158 |
| IL6 | BP | CTGCAGGAACTCCTTAAAGCTG | 159 |
| IL6 | BP | CCCATTAACAACAACAATCTGAGG | 160 |
| IL6 | LE | ggctcctggaggcgagataTTTTTaggcataggacccgtgtct | 161 |
| IL6 | LE | aactggaccgaaggcgctTTTTTaggcataggacccgtgtct | 162 |
| IL6 | LE | gcaggcaacaccaggagcTTTTTaggcataggacccgtgtct | 163 |
| IL6 | LE | aagaggtgagtggctgtctgtgTTTTTaggcataggacccgtgtct | 164 |
| IL6 | LE | gaatttgtttgtcaattcgttctgTTTTTaggcataggacccgtgtct | 165 |
| IL6 | LE | gatgccgtcgaggatgtaccTTTTTaggcataggacccgtgtct | 166 |
| IL6 | LE | ctgccagtgcctctttgctTTTTTaggcataggacccgtgtct | 167 |
| IL6 | LE | gcatccatcttttcagccatcTTTTTaggcataggacccgtgtct | 168 |
| IL6 | LE | atgattttcaccaggcaagtctTTTTTaggcataggacccgtgtct | 169 |
| IL6 | LE | atctgttctggaggtactctaggtataTTTTTaggcataggacccgtgtct | 170 |
| IL6 | LE | ggcttgttcctcactactctcaaTTTTTaggcataggacccgtgtct | 171 |
| IL6 | LE | ttttgtactcatctgcacagctctTTTTTaggcataggacccgtgtct | 172 |
| IL6 | LE | ctgcaggaactggatcaggacTTTTTaggcataggacccgtgtct | 173 |
| IL6 | LE | gcatctagattctttgccttttTTTTTaggcataggacccgtgtct | 174 |
| IL6 | LE | gcaggctggcatttgtggTTTTTaggcataggacccgtgtct | 175 |
| IL6 | LE | tgtgcctgcagcttcgtcaTTTTTaggcataggacccgtgtct | 176 |
| IL6 | LE | tgtcctgcagccactggttcTTTTTaggcataggacccgtgtct | 177 |
| IL6 | LE | cgcagaatgagatgagttgtcaTTTTTaggcataggacccgtgtct | 178 |
| IL6 | LE | tgcccatgctacatttgccTTTTTaggcataggacccgtgtct | 179 |
| IL6 | LE | ggtttctgaccagaagaaggaatgTTTTTaggcataggacccgtgtct | 180 |
| IL6 | LE | aagttctgtgcccagtggacaTTTTTaggcataggacccgtgtct | 181 |

TABLE 3 -continued

Probe sets (CPs, CEs, LEs, and BPs) for the cytokine panel.

| Gene | | | SEQ ID NO |
|---|---|---|---|
| IL6 | CE | gagcttctctttcgttcccgTTTTTggggaacatagaaaa | 182 |
| IL6 | CE | tgtggagaaggagttcatagctgTTTTTggggaacatagaaaa | 183 |
| IL6 | CE | agccccagggagaaggcTTTTTggggaacatagaaaa | 184 |
| IL6 | CE | tgtctcctttctcagggctgaTTTTTggggaacatagaaaa | 185 |
| IL6 | CE | cctcattgaatccagattggaaTTTTTggggaacatagaaaa | 186 |
| IL6 | CE | gaagagccctcaggctggaTTTTTggggaacatagaaaa | 187 |
| IL6 | CP | TTTTTTTTTTTTCTATGTTCCCC | 188 |
| IL8 | BP | CAAAAACTTCTCCACAACCCTC | 189 |
| IL8 | BP | AGTGTTGAAGTAGATTTGCTTGAAGT | 190 |
| IL8 | BP | CAACAGACCCACACAATACATGA | 191 |
| IL8 | BP | GTACAATGAAAAACTATTCATTGTTTACT | 192 |
| IL8 | BP | TTTTTTGTAGATTCAAATAAATAATACTTTA | 193 |
| IL8 | BP | AAATCCTTATATTTAAAAATTATTTGTTG | 194 |
| IL8 | BP | GCTTCAAATATCACATTCTAGCAAAC | 195 |
| IL8 | BP | AAAAAATCCAGGATTTCCAGCt | 196 |
| IL8 | BP | CTAGGGTTGCCAGATTTAACAGA | 197 |
| IL8 | BP | CCACTTAGAAATAAAGGAGAAACCA | 198 |
| IL8 | BP | CATGTCCTCACAACATCACTGTGA | 199 |
| IL8 | BP | ATGAAAAAACTTAAAGTGCTTCCA | 200 |
| IL8 | BP | AAGTTACACTTGAAAATAATTTATGTTATG | 201 |
| IL8 | BP | TTAAATAAATACATAAATAATAAATAGGTTAAT | 202 |
| IL8 | BP | ATAAAACATCATTTAATATCTAAAATAAAAT | 203 |
| IL8 | BP | TAAAACCCTGATTGAAATTTATCTA | 204 |
| IL8 | LE | ggtccagacagagctctcttccTTTTTaggcataggacccgtgtct | 205 |
| IL8 | LE | ttggataccacagagaatgaatttTTTTTaggcataggacccgtgtct | 206 |
| IL8 | LE | ttcactggcatcttcactgattcTTTTTaggcataggacccgtgtct | 207 |
| IL8 | LE | tgtattgcatctggcaaccctaTTTTTaggcataggacccgtgtct | 208 |
| IL8 | LE | gaaattcaaatttaaccaggaatctTTTTTaggcataggacccgtgtct | 209 |
| IL8 | LE | catataagtatgttctggatatttcatgTTTTTaggcataggacccgtgtct | 210 |
| IL8 | LE | ttctcccgtgcaatatctaggaTTTTTaggcataggacccgtgtct | 211 |
| IL8 | LE | ggcctcaattttgctatttgtataTTTTTaggcataggacccgtgtct | 212 |
| IL8 | LE | ccattcaattcctgaaattaaagttTTTTTaggcataggacccgtgtct | 213 |
| IL8 | LE | attgtcccatcatttttatgtgatTTTTTaggcataggacccgtgtct | 214 |
| IL8 | LE | aaatttgactttatggcaaaatttTTTTTaggcataggacccgtgtct | 215 |
| IL8 | LE | aggcacagtggaacaaggactTTTTTaggcataggacccgtgtct | 216 |
| IL8 | LE | ggtaagatggtggctaatactttttTTTTTaggcataggacccgtgtct | 217 |
| IL8 | LE | aattcttgcacaaatatttgatgcTTTTTaggcataggacccgtgtct | 218 |

TABLE 3 -continued

Probe sets (CPs, CEs, LEs, and BPs) for the cytokine panel.

| Gene | | | SEQ ID NO |
|---|---|---|---|
| IL8 | LE | caatgattcatcttctattttttccaTTTTTaggcataggacccgtgtct | 219 |
| IL8 | LE | aaatttactataacatctttataactattcaatTTTTTaggcataggacccgtgtct | 220 |
| IL8 | CE | tgcacccagttttccttggTTTTTtttcaaatgttagcct | 221 |
| IL8 | CE | ttttatgaattctcagccctcttTTTTTttcaaatgttagcct | 222 |
| IL8 | CE | cggatattctcttggcccttTTTTTttcaaatgttagcct | 223 |
| IL8 | CE | tgtggatcctggctagcagaTTTTTttcaaatgttagcct | 224 |
| IL8 | CE | acccaattgtttgtttgtttaatcTTTTTttcaaatgttagcct | 225 |
| IL8 | CP | TTTTTTTTAGGCTAACATTTGAA | 226 |
| TNF | BP | CCCTCTGGGGGCCGA | 227 |
| TNF | BP | GAGGTCCCTGGGGAACTCTT | 228 |
| TNF | BP | ggccagagggctgattagaga | 229 |
| TNF | BP | AGGCTTGTCACTCGGGGTT | 230 |
| TNF | BP | tgaagaggacctgggagtagatg | 231 |
| TNF | BP | GGGCAGCCTTGGCCCT | 232 |
| TNF | BP | TGGCAGGGGCTCTTGATG | 233 |
| TNF | BP | CCCCTCTGGGGTCTCCCTC | 234 |
| TNF | BP | GTTTGGGAAGGTTGGATGTTC | 235 |
| TNF | BP | TGGGGCAGGGGAGGC | 236 |
| TNF | BP | AGGAGGGGGTAATAAAGGGAT | 237 |
| TNF | LE | tcactccaaagtgcagcaggTTTTTaggcataggacccgtgtct | 238 |
| TNF | LE | ggtttgctacaacatgggctacTTTTTaggcataggacccgtgtct | 239 |
| TNF | LE | ggcggttcagccactggaTTTTTaggcataggacccgtgtct | 240 |
| TNF | LE | caggagggcattggcccTTTTTaggcataggacccgtgtct | 241 |
| TNF | LE | agctccacgccattggcTTTTTaggcataggacccgtgtct | 242 |
| TNF | LE | caccaccagctggttatctctcTTTTTaggcataggacccgtgtct | 243 |
| TNF | LE | aggtacaggccctctgatggTTTTTaggcataggacccgtgtct | 244 |
| TNF | LE | tgaggagcacatgggtggagTTTTTaggcataggacccgtgtct | 245 |
| TNF | LE | gcggctgatggtgtgggTTTTTaggcataggacccgtgtct | 246 |
| TNF | LE | gcagagaggaggttgaccttgTTTTTaggcataggacccgtgtct | 247 |
| TNF | LE | cagggcttggcctcagcTTTTTaggcataggacccgtgtct | 248 |
| TNF | LE | tctccagctggaagaccccTTTTTaggcataggacccgtgtct | 249 |
| TNF | LE | gcgctgagtcggtcaccctTTTTTaggcataggacccgtgtct | 250 |
| TNF | LE | agactcggcaaagtcgagatagTTTTTaggcataggacccgtgtct | 251 |
| TNF | LE | atcccaaagtagacctgcccTTTTTaggcataggacccgtgtct | 252 |
| TNF | LE | gtcctcctcacagggcaatgTTTTTaggcataggacccgtgtct | 253 |
| TNF | LE | cagaagaggttgagggtgtctgaTTTTTaggcataggacccgtgtct | 254 |
| TNF | LE | gcttgggttccgaccctaagTTTTTaggcataggacccgtgtct | 255 |

TABLE 3 -continued

Probe sets (CPs, CEs, LEs, and BPs) for the cytokine panel.

| Gene | | | SEQ ID NO |
|---|---|---|---|
| TNF | CE | cgagaagatgatctgactgcctgTTTTTctgagtcaaagcatt | 256 |
| TNF | CE | gctgcccctcagcttgagTTTTTctgagtcaaagcatt | 257 |
| TNF | CE | gtctggtaggagacggcgatTTTTTctgagtcaaagcatt | 258 |
| TNF | CE | tcccagatagatgggctcatacTTTTTctgagtcaaagcatt | 259 |
| TNF | CE | tcgggccgattgatctcaTTTTTctgagtcaaagcatt | 260 |
| TNF | CE | cccccaattctcttttttgagcTTTTTctgagtcaaagcatt | 261 |
| TNF | CP | TTTTTTTTAATGCTTTGACTCAG | 262 |
| VEGF | BP | CATCAGGGGCACACAGGATG | 263 |
| VEGF | BP | GCAGCCCCCGCATCG | 264 |
| VEGF | BP | CTCCTCAGTGGGCACACACTC | 265 |
| VEGF | LE | tggaggtagagcagcaaggcTTTTTaggcataggacccgtgtct | 266 |
| VEGF | LE | tgggaccacttggcatggTTTTTaggcataggacccgtgtct | 267 |
| VEGF | LE | gatgattctgccctcctcctTTTTTaggcataggacccgtgtct | 268 |
| VEGF | LE | tccatgaacttcaccacttcgtTTTTTaggcataggacccgtgtct | 269 |
| VEGF | LE | gcagtagctgcgctgatagacaTTTTTaggcataggacccgtgtct | 270 |
| VEGF | LE | accagggtctcgattggatgTTTTTaggcataggacccgtgtct | 271 |
| VEGF | LE | agggtactcctggaagatgtccTTTTTaggcataggacccgtgtct | 272 |
| VEGF | LE | gcttgaagatgtactcgatctcatcTTTTTaggcataggacccgtgtct | 273 |
| VEGF | LE | caggccctcgtcattgcaTTTTTaggcataggacccgtgtct | 274 |
| VEGF | LE | TaatctgcatggtgatgttggaTTTTTaggcataggacccgtgtct | 275 |
| VEGF | LE | atttgttgtgctgtaggaagctcTTTTTaggcataggacccgtgtct | 276 |
| VEGF | LE | ctgatttttttttcttgtcttgctctTTTTTaggcataggacccgtgtct | 277 |
| VEGF | LE | ttgcgctttcgtttttgcTTTTTaggcataggacccgtgtct | 278 |
| VEGF | LE | ggcccacagggaacgctTTTTTaggcataggacccgtgtct | 279 |
| VEGF | CE | aaggctccaatgcacccaTTTTTctttgagttcggttt | 280 |
| VEGF | CE | ctgccatgggtgcagccTTTTTctttgagttcggttt | 281 |
| VEGF | CE | tggtgaggtttgatccgcaTTTTTctttgagttcggttt | 282 |
| VEGF | CE | atctctcctatgtgctggcctTTTTTctttgagttcggttt | 283 |
| VEGF | CE | atctttctttggtctgcattcacTTTTTctttgagttcggttt | 284 |
| VEGF | CE | ccctttcccttcctcgaaTTTTTctttgagttcggttt | 285 |
| VEGF | CE | ccaggacttataccgggatttcTTTTTctttgagttcggttt | 286 |
| VEGF | CP | TTTTTTTTAAACCGAACTCAAAG | 287 |

Regulation of Gene Expression from Cellular Models of Inflammation and Apoptosis To demonstrate the utility of this assay using cell lysates, two well-characterized cell culture model systems that elicit expression changes in genes were employed within the panels. The first model system utilized PMA/LPS treatment of U937 cells to monitor the changes of cytokine gene expression in inflammatory responses, and the second model utilized TNFα-treated HeLa cells to monitor expression changes in pro- and anti-apoptotic genes.

U937 cells with or without PMA/LPS treatment were lysed in the culture flask by adding a lysis buffer (from QuantiGene and QuantiGene Plex kit) directly to the culture media. Since the lysis buffer facilitates the release and hybridization of intact mRNA, crude cell lysates were used directly for all multiplex bDNA assays. Gene expression was measured in the 10-plex cytokine panel for control and PMA/LPS treated U937 cells. 40,000 cell equivalents of cell lysate was used in the assay. When the assay signal for a gene was below the detection limit, the expression level of that gene was not plotted. The measurements were performed in quadruplicate and data acquired from Luminex 100™ is normalized to the housekeeping gene GAPD. Error bar represents 1 s.d.

As shown in FIG. 8 Panel A, untreated U937 cells, GAPDH and VEGF were expressed at a high level, IL8, IL1b, and TNFα were expressed at moderate to low level, and IL6, IL10, CSF2 (GM-CSF), IL2, and IFN-γ are not significantly above the background. PMA/LPS treatment strongly induced the expression of proinflammatory cytokines IL8, IL-1b and TNFα. However, cytokines IL6, IL10 and CSF2 were only moderately induced, while IFN-γ and IL2 and VEGF remain essentially unchanged. The average % CV of the measurements (including both signal and background) for uninduced cells was 12.8%, and for induced cells was 8.9%. The signals of the induced genes increased linearly with the increasing amount of cell lysate (e.g., 6,000 to 25,000 cells) assayed, while the background level remained the same throughout, demonstrating the specific nature of the assay signal. Further verification of mRNA levels from the same cell lysates was performed using the well-established single-plex bDNA assay (FIG. 8 Panel B). 20,000 cell equivalents of cell lysate was used in the assay. The measurements were performed in quadruplicate and data normalized to 40,000 cell equivalents and to housekeeping gene GAPD. Error bar represents 1 s.d. The results showed a highly similar pattern of gene expression to the results of the multiplex assay, with a correlation factor of 0.94 by matched pair analysis (FIG. 8 Panel B).

Figure 9A:
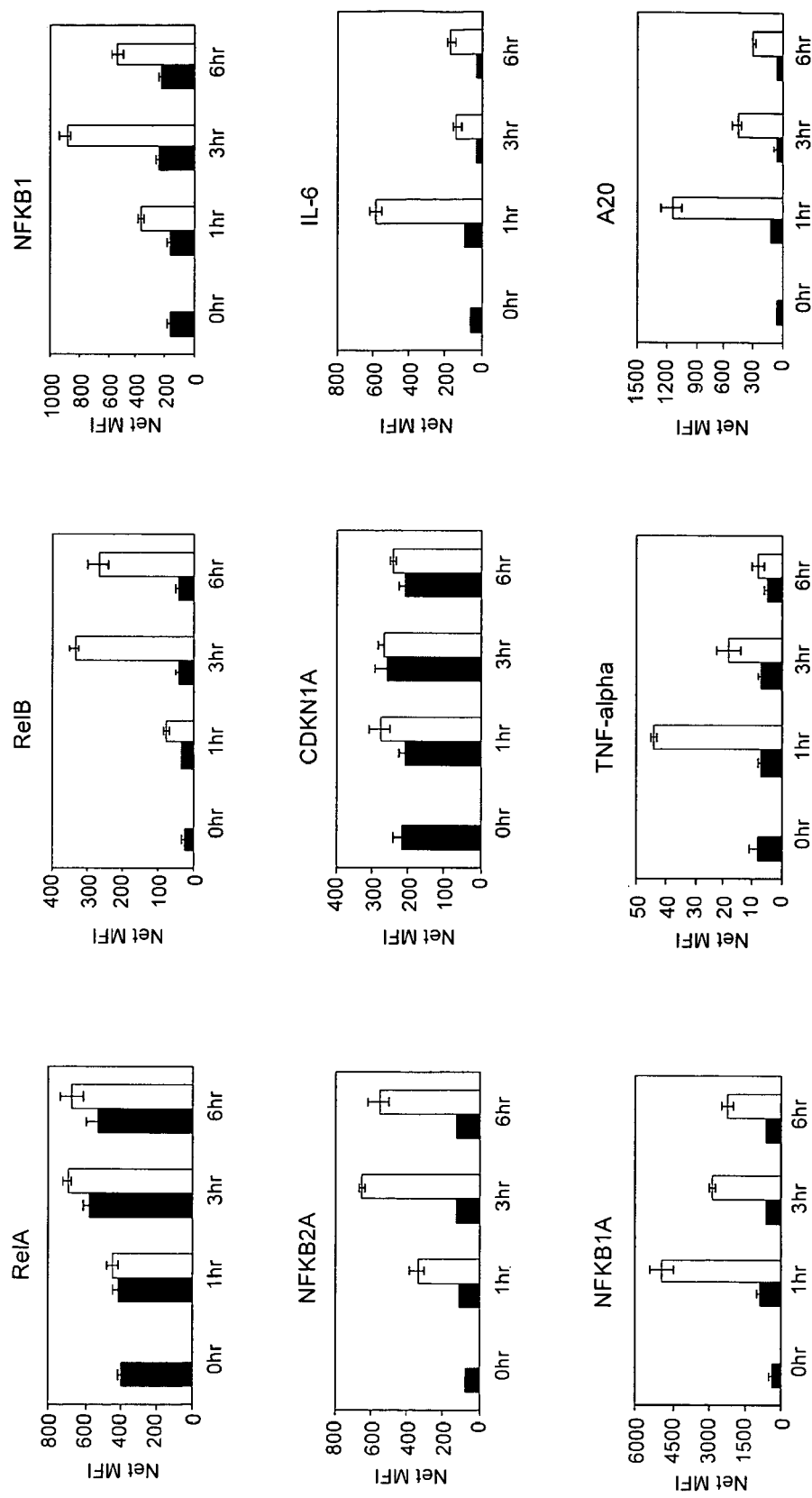
FIG. 9 Panel A depicts bar graphs illustrating time-dependent expression of pro- and anti-apoptotic genes upon TNFα treatment of HeLa cells, as detected by a 10-plex bDNA assay. Panel B depicts bar graphs illustrating expression of pro- and anti-apoptotic genes in untreated cells and in TNFα-treated cells, 3 hours after treatment, as detected by single-plex bDNA assays (top) and a 10-plex bDNA assay (bottom).
Figure 9B:
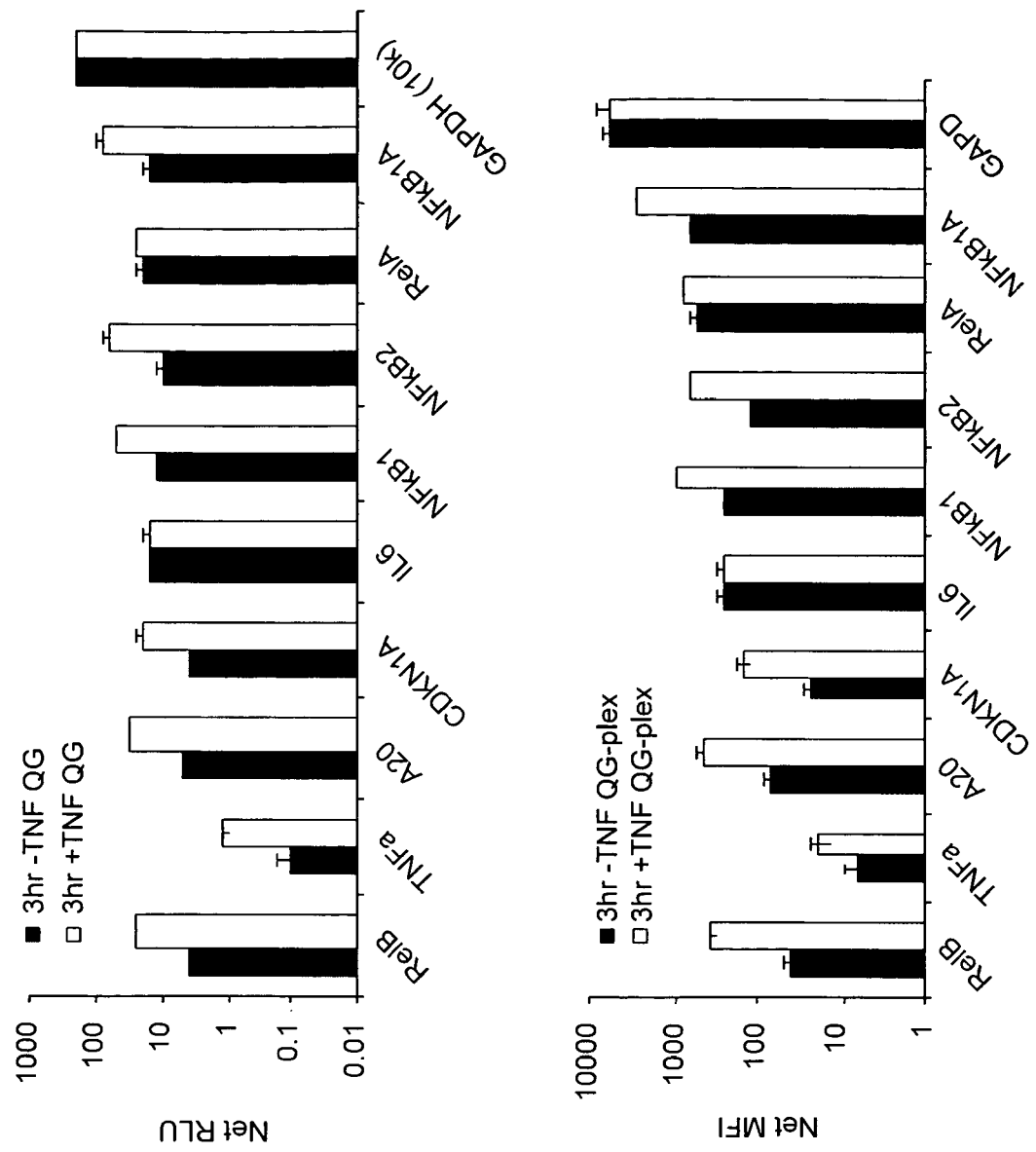

To further demonstrate the utility of the multiplex assay, two 10-plex apoptosis panels were developed and used to analyze gene expression from HeLa cells treated with TNFα for 1 to 6 hours. One apoptosis panel measures the expression of several major subunits of the NF-kB transcription complexes, including RelA, RelB, NFKB1, NFKB2, and NFKB1A, as well as a number of additional pro- and anti-apoptotic regulators, and a number of cytokines (Table 1). Expression of individual genes in the 10-plex apoptosis panel with or without TNFα treatment for 0, 1, 3, or 6 hours is shown in FIG. 9 Panel A. 80,000 cell equivalents of cell lysate was used in the assay except for GAPD where data was obtained from 10,000 cell equivalents of cell lysate. The measurements were performed in triplicate with data acquired from a Bio-Plex instrument at high sensitivity setting and normalized to housekeeping gene GAPD.

Several patterns of gene expression were observed (FIG. 9 Panel A). The expression of A20 and TNFα was rapidly elevated after 1 hour, then declined after 3 hour, and further declined after 6 hour of TNFα stimulation. The expression of NFKB1, NFKB2, NFKB1A, and IL-6 was increased after 1 hour, and maintained at roughly the similar level (within 2-fold of each other) after 3 hour and 6 hour of TNFα stimulation. The expression of RELB increased moderately at 1 hour, but elevated at much higher level after 3 hours and 6 hours of TNFα stimulation. Consistent with their known functional role in the NF-kB transcription complex and in cell cycle control, the expression levels of RELA and CDKN1A did not change significantly upon TNFα treatment. The average % CV of all expression measurements was 8.5%. Verification tests of these results were performed by measuring the expression levels of all ten genes in control and 3 hour TNFα-treated samples with the single-plex bDNA assay. 40,000 cell equivalents of cell lysate was used in each assay except for GAPD where data was obtained from 10,000 cell equivalents of cell lysate. Measurements from both technologies reveal similar relative expression levels and fold-of-induction changes (FIG. 9 Panel B). Correlation ($R^2$) between expression measurements for untreated samples was >0.99, and for treated samples $R^2$>0.94 was observed across both panels.

Performance evaluation data for the two apoptosis panels is summarized in Tables 4 and 5.

TABLE 4

Detection sensitivity, cross-reactivity, and assay background of the apoptosis 1 panel.

| Gene | RELA | NFKB2 | NKFB1 | RELB | IL6 | GAPD | NFKB1A | TNFAIP3 | TNFA | CDKN1A |
|---|---|---|---|---|---|---|---|---|---|---|
| LOD (amol) | 0.06 | 0.06 | 0.04 | 0.04 | 0.04 | 0.04 | 0.16 | 0.04 | 0.04 | 0.04 |
| % Cross-reactivity | 0.024% | 0.028% | 0.023% | 0.028% | 0.005% | 0.02% | 0.017% | 0.019% | 0.044% | 0.023% |
| Average background (MFI) | 53.3 | 19.5 | 10.1 | 14.5 | 15.9 | 18.1 | 82.1 | 31.1 | 15.6 | 16 |
| % Intra-plate CV | 13 | 10 | 14 | 13 | 9 | 9 | 12 | 11 | 11 | 9 |
| % Inter-plate CV | 16 | 16 | 14 | 13 | 8 | 12 | 10 | 14 | 12 | 13 |

TABLE 5

Detection sensitivity, cross-reactivity, and assay background of the apoptosis 2 panel.

| Gene | BCL2L1 | IL6R | BCL2 | BAK1 | PTK2B | ACTB | CFLAR | TNFRSF6 | TNFSF6 | BAD |
|---|---|---|---|---|---|---|---|---|---|---|
| LOD (amol) | 0.04 | 0.04 | 0.16 | 0.16 | 0.04 | 0.04 | 0.06 | 0.04 | 0.04 | 0.16 |
| % Cross-reactivity | 0.021% | 0.005% | 0.038% | 0.072% | 0.006% | 0.016% | 0.021% | 0.038% | 0.345% | 0.024% |
| Average background (MFI) | 9.9 | 24.3 | 72.6 | 26.4 | 15.3 | 11.6 | 24.4 | 16.5 | 17.8 | 14.8 |
| % Intra-plate CV | 7 | 7 | 8 | 9 | 7 | 10 | 8 | 10 | 6 | 11 |

TABLE 5-continued

Detection sensitivity, cross-reactivity, and assay background of the apoptosis 2 panel.

| Gene | BCL2L1 | IL6R | BCL2 | BAK1 | PTK2B | ACTB | CFLAR | TNFRSF6 | TNFSF6 | BAD |
|---|---|---|---|---|---|---|---|---|---|---|
| % Inter-plate CV | 11 | 11 | 18 | 23 | 14 | 15 | 15 | 13 | 14 | 16 |

Advantages of the Multiplex bDNA Assays

The above experiments demonstrate that the multiplex bDNA assay is a simple and robust method for gene expression quantification that generates sensitive and reproducible results directly from crude cell lysates, without need for RNA purification, reverse transcription, or target amplifications. One distinctive feature of the assay is its remarkable specificity and accuracy. Cooperative hybridization was demonstrated in a single-plex bDNA assay. Cooperative hybridization can enable exceptionally high assay specificity, enabling multiplexing of the assay. A target mRNA transcript can only be stably captured to its corresponding beads when the transcript binds to multiple CEs. Even when an unintended mRNA transcript binds to one of the CEs in a probe set, the mRNA transcript cannot be stably captured to the beads. Thus, cooperative hybridization can potentially provide two major advantages over simple hybridization currently used in most hybridization based assays: 1) it dramatically reduces the assay background caused by nonspecific cross hybridization; and 2) it enables better discrimination of homologous genes. By leveraging cooperative hybridization in the design of the capture probes, less than 0.1% cross-reactivity has been achieved in all the multiplex panels developed so far, including a rat toxicity panel where several highly homologous cytochrome P450 genes are present. Specificity of the assay is further demonstrated by its excellent spike recovery in the presence of a complex background of total RNA. Because of its exceptional assay specificity, the results of mRNA quantification are therefore highly accurate and reliable.

Another distinctive feature of the assay is its simplicity. The assay can quantify RNA transcripts in crude cell lysates and tissue homogenates, as demonstrated in this study using cell lysates from two different cell lines. This feature distinguishes the assay from many other existing mRNA quantification technologies, and makes the assay one of the few that directly measures the mRNA transcripts from their native environment, thus free of any bias imposed by purification procedures and enzymatic reactions. By eliminating the RNA purification, reverse transcription, labeling and amplification steps, assay variations are minimized, leading to significantly improved precision for the overall assay. In addition, since the need for sample preparation is eliminated, the multiplex bDNA assay is well suited for high throughput expression analysis of large sample populations.

The third distinctive feature of the assay is its high precision and reproducibility. The intra-plate CV is routinely below 10% and the inter-plate CV routinely below 15% in all experiments where triplicate samples are run, whether the samples are total RNA or cell lysates. The level of consistency in multiplex bDNA assay data is a particularly attractive feature required for quantitative measurement of gene expression in siRNA knockdown, structure-activity relationship, drug dose response, and drug screening applications, where a change of gene expression as small as 10 to 30% needs to be reliably determined and differentiated.

Finally, the multiplex bDNA assay is capable of measuring multiple mRNA transcripts simultaneously with good sensitivity and broad dynamic range. The current assay can be expected to detect mRNA transcripts at a concentration as low as 1 copy per cell from a few as 25,000 cells (i.e., the detection sensitivity is 25,000 transcripts), and two mRNA transcripts differing in concentration by as much as 1,000-fold can both be quantified in the same assay with high accuracy. Sensitivity can optionally be increased by decreasing the assay volume (e.g., to 50 µl), including more LEs per probe set so that more amplification multimers bind to each mRNA, and/or using amplification multimers with a higher theoretical fold of amplification. Less than 0.1% cross-reactivity is routinely achieved in more than a dozen multiplex panels tested so far, including cytochrome P450 and ABC transporter panels where several genes with up to 96% homology are present. 30- and 40-plex bDNA assays have been performed, with the same performance characteristics.

Although the multiplex bDNA assays described herein simultaneously quantify ten mRNA targets in a single assay, the Luminex technology platform was designed for simultaneous measurement of up to 100 bead analytes. The number of targets in the multiplex bDNA assay can thus be readily increased, e.g., by taking advantage of this platform. Expansion of the multiplex bDNA assay will permit more detailed analysis of mRNA levels in particular pathways and enable more robust systems biology studies. Increased multiplex capability may be desirable for some applications such as microarray validation and follow up studies.

The multiplex bDNA assay enables collection of a large amount of data that previously were experimentally challenging to obtain. For example, a previously published study on the cytokine response to inflammatory stimuli was mostly focused on two to three cytokines at a time (Hass et al. (1991) "Regulation of TNF-alpha, IL-1 and IL-6 synthesis in differentiating human monoblastoid leukemic U937 cells" Leuk Res. 15:327-39, and Roberts et al. (1997) "Effects of *Porphyromonas gingivalis* and *Escherichia coli* lipopolysaccharides on mononuclear phagocytes" Infect Immun. 65:3248-54). With the multiplex bDNA assay, the quantitative expression of dozens of cytokine genes can now be investigated. The multiplex expression analysis of time dependent regulation of apoptotic gene expression upon TNF-alpha treatment in HeLa cells illustrates the potential for high throughput quantitative gene expression analysis. The throughput of the multiplex bDNA assay enables the detailed expression analysis in many samples that received different drug treatments at various dose for different length of times.

In summary, the simplicity, sensitivity, accuracy and high reproducibility of the assay, together with the multiplex capability, makes the multiplex bDNA assay a valuable tool, e.g., in applications where accurate and robust quantification of multiple mRNA targets is required, where samples and reagents are precious and limited, and where easy and high throughput sample processing is desired, such as in biomarker validation, compound screening, structure-activity relationship study, toxicity studies, and potentially clinical diagnostics.

Methods

Cooperative Hybridization

To determine the effect of cooperative hybridization, three oligonucleotide capture probes containing 14, 15, or 16 bases complementary to the CE tails were covalently conjugated to capture plates, respectively, following a published procedure (Running and Urdea (1990) "A procedure for productive coupling of synthetic oligonucleotides to polystyrene microtiter wells for hybridization capture" Biotechniques. 8:276-279). The sequences of the three capture probes are as follows: 16 base capture probe, 5'-amine-spacer-ACTTTCTTTCCAAGAG-3' (SEQ ID NO:1); 15 base capture probe, 5'-amine-spacer-ACTTTCTTTCCAAGA-3' (SEQ ID NO:2); and 14 base capture probe, 5'-amine-spacer-ACTTTCTTTCCAAG-3' (SEQ ID NO:3). Standard bDNA assays were run on the assay plates coupled with the three capture probes, respectively, using IVT RNA of IL-6 as standard and the bDNA assay probe set for IL-6. To determine the extent of simple hybridization, an oligonucleotide probe (CE-LE) that combines the sequences of the CE tail and the LE tail together was used in bDNA assay in place of the probe set and target RNA. The sequence of the CE-LE probe is as follow: 5'-AGGCATAGGACCCGTGTCttttCTCTTGGAAAGAAAGT-3' (SEQ ID NO:4), where the series of five small letter t's denotes the linker sequence between the LE tail and the CE tail.

Single-Plex bDNA Assay

Single-plex bDNA assay was performed according to the Instruction Manual of the QuantiGene® Reagent System (Panomics). Briefly, cells were incubated with Lysis Mixture for 15 min at 37° C. in 100 µL volume. Probe set for a target gene was added to the cell lysate, transferred to a capture well, and then incubated for 16 hr at 53° C. Unbound material was washed from wells, followed by sequential hybridization at 46° C. with branched DNA (bDNA) amplifier and alkaline phosphatase-conjugated label probe. After a final wash, the alkaline phosphatase substrate dioxetane was added to wells and incubated at 46° C. for 30 min to develop luminescent signal, which was detected using an Lmax microtiter plate luminometer (Molecular Devices, Sunnyvale, Calif.).

Capture Probes and their Coupling to Fluorescent-Encoded Beads

Unique sequences of 15 bases were chosen as capture probes. The capture probes were designed to have minimal potential for secondary structure formation or cross-hybridization. They were also screened against homology with sequences of human, mouse or rat genes (BLAST and NCBI databases) or sequences in the bDNA and label probe. Oligonucleotide capture probes were synthesized with 5'-amino linker (BioSearch) and covalently linked to carboxylated fluorescent-encoded microsphere beads (Luminex) following the recommended conjugation procedure from Luminex. Hybridization specificity was evaluated by hybridizing ten coupled microsphere beads to a biotinylated complementary oligonucleotide under the same hybridization conditions as the bDNA assay.

In Vitro Transcribed RNA (IVT RNA)

Complementary DNA clones encoding the full-length target genes were obtained commercially and used as templates for in vitro transcription to generate IVT RNA standards (Invitrogen; Origene; or Open Biosystems). IVT RNA was transcribed for each gene from the restriction enzyme digested plasmid via T3, T7, or SP6 promoters using the Ampliscribe kit (Amersham), quantified using RiboGreen fluorescence (Molecular Probes) and the Envision 2100 Multilabel reader (Perkin Elmer). IVT RNA transcripts for each panel were mixed and serially diluted four-fold to generate standard curve with target RNA levels ranging from $9.6 \times 10^7$ to $2.4 \times 10^4$ transcripts. The IVT RNA was used as a reference standard to assess the assay sensitivity, specificity, accuracy, and linear dynamic range.

Probe Design for Single-Plex and Multiplex bDNA Assays

Probe design software (Bushnell et al. (1999) "ProbeDesigner: for the design of probe sets for branched DNA (bDNA) signal amplification assays Bioinformatics 15:348-55) was modified to design probe sets for target genes in both single-plex and multiplex bDNA assays. For each target sequence, the software algorithm identifies regions that can serve as annealing templates for CEs (5-7 per gene), LEs (10-15 per gene), or BPs. Potential CEs and LEs were examined for possible interactions with other components of the multiplex assay, and CEs and LEs expected to cross-hybridize were not selected for use: CE-LE, CE-bDNA, CE-label probe, and LE-capture probe interactions having highly negative ΔG (e.g., <−7.0 kcal/mole) were removed to minimize non-specific hybridization. Probe sets are essentially the same for both single-plex and multiplex bDNA assay except for the portion of the CE probes that hybridize with capture probe. Several 10-plex panels were developed for the experimental validation. Gene names and reference sequence accession numbers are shown in Table 1; probe sets are shown in Table 3.

Multiplex bDNA Assay

Multiplex bDNA assay was performed basically as described in the Instruction Manual of the QuantiGene® Plex Reagent System (Panomics). Briefly, samples containing IVT RNA, total RNA or cell lysates were mixed with the multiplex panel probe sets and the capture beads (about 2000 beads per subset) and hybridized for 16 hours at 53° C. in 100 µL volume. The components in a 100-µL IVT RNA assay were 33% lysis mixture, 40% capture buffer (Panomics), 1 µg tRNA, and the panel-specific probe set (CE, 0.165 fmol/µl/gene; LE, 0.66 fmol/µl/gene; BP, 0.33 fmol/µl/gene). (Hybridization can be performed under any of a variety of suitable conditions; for example, in a solution including the capture diluent described in Collins M L et al. (1997) Nucleic Acid Research 25:2979-2984: 127 mM LiCl, 5% lithium lauroyl sulfate, 9 mM EDTA, 50 mM HEPES (pH 7.5), 0.05% hespan (DuPont Pharmaceuticals), 0.05% ProClin 300 (Supelco), and 0.2% casein (Research Organics, Hammarsten quality).) Hybridization reactions were transferred to a 0.45-µm filter plate (Millipore, Billerica, Mass., USA), followed by sequential hybridization at 46° C. with bDNA amplifier and 5'-dT(biotin)-conjugated label probe. Unbound materials were washed from beads (complexed with probe set and mRNA) through alternating filtration and the addition of wash buffer (0.1×SSC, 0.03% lithium lauryl sulfate). Two washes were performed after each hybridization step. After a final wash, Streptavidin conjugated R-Phycoerythrin (SAPE) was added and was incubated at room temperature for 30 min. The beads were washed to remove unbound SAPE, followed by analysis with Luminex[100]IS system (Luminex) or a Bio-Plex system (Bio-Rad). The level of SAPE fluorescence measured from each bead is proportional to the number of mRNA transcripts captured by the bead.

Cell Lysates for Evaluation of the Cytokine Panel

U937 cells (American Type Culture Collection) at a density around $1-2 \times 10^5$ cells/ml were allowed to differentiate in SFM media (GIBCO) with 100 nM Phorbol-12-myrstyl-13-acetate (PMA, Sigma) for 48 hrs. Differentiated cells, which become adherent, were stimulated with lipopolysaccharide (LPS, Sigma) at a concentration of 1 µg/ml in RPMI growth media (GIBCO) with 10% FBS for 4 hours. After cell counting, the cells were directly lysed in the culture flask by the addition of Lysis Mixture to the culture media and incubated at 37° C. for 15 minutes.

Cell Lysates for Evaluation of the Apoptosis Panel

HeLa cells (American Type Culture Collection) were cultured in Dulbecco's modified Eagle's medium (Invitrogen) at an approximate density of 1-2×10⁶ cells/ml and were treated with recombinant human TNFα (1 ng/ml, R&D Systems) or 1% BSA/PBS vehicle control. Both TNFα-treated and vehicle-treated cells were harvested at 1, 3 and 6 hour post-treatment by the addition of Lysis Mixture directly to the culture flasks in order to generate cell lysates suitable for both single-plex and multiplex assays.

Data Analysis & Statistics

Three replicate assays (n=3) were performed for all described experimental samples unless noted otherwise. For all samples, background signal levels in the absence of target mRNAs were determined and subtracted from signals obtained in the presence of target mRNAs. The correlation between the single-plex and multiplex bDNA assay was assessed through matched pair analysis using JMP (SAS Institute). Statistical significance of biological studies was tested using student's t-test or ANOVA where appropriate ($P<0.01$).

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of detecting ten or more different target nucleic acids of interest, the method comprising:
providing a sample comprising nucleic acids;
providing a solid phase having associated therewith ten or more different capture probes;
providing ten or more subsets of n capture extenders, wherein n is at least two, wherein each subset of n capture extenders is capable of hybridizing to a different target nucleic acid, and wherein the capture extenders in each subset are capable of hybridizing to one of the capture probes and thereby associating each subset of n capture extenders with the solid phase;
contacting the sample, the solid phase, and the subsets of n capture extenders;
hybridizing any of the different target nucleic acids present in the sample to its complementary subset of n capture extenders and hybridizing the subset of n capture extenders to its complementary capture probe, thereby capturing the target nucleic acid on the solid phase,
wherein the hybridizing the subset of n capture extenders to the complementary capture probe is performed at a hybridization temperature which is greater than a melting temperature $T_m$ of a complex between each individual capture extender and its complementary capture probe;
hybridizing one or more label extenders to target nucleic acids captured on the solid phase;
hybridizing a preamplifier to the label extenders, hybridizing a plurality of amplification multimers to the preamplifier, and hybridizing a plurality of label probes to each of the amplification multimers, wherein each of the label probes comprises or binds a label; and
detecting the presence or absence of the different target nucleic acids captured on the solid phase.

2. The method of claim 1, wherein providing a solid phase comprises providing a pooled population of particles, the population comprising ten or more subsets of particles, a plurality of the particles in each subset being distinguishable from a plurality of the particles in every other subset, and the particles in each subset having associated therewith a different one of the ten or more capture probes; and
wherein detecting the presence or absence of the different target nucleic acids captured on the solid phase comprises identifying at least a portion of the particles from each subset and detecting the presence or absence of the label on those particles, thereby determining which subsets of particles have a target nucleic acid of interest captured on the particles and thereby indicating which of the ten or more different target nucleic acids of interest were present in the sample.

3. The method of claim 2, wherein the ten or more target nucleic acids of interest comprise 20 or more target nucleic acids of interest, wherein the ten or more subsets of particles comprise 20 or more subsets of particles, and wherein the ten or more subsets of n capture extenders comprise 20 or more subsets of n capture extenders.

4. The method of claim 2, wherein the ten or more target nucleic acids of interest comprise 30 or more target nucleic acids of interest, wherein the ten or more subsets of particles comprise 30 or more subsets of particles, and wherein the ten or more subsets of n capture extenders comprise 30 or more subsets of n capture extenders.

5. The method of claim 2, wherein the particles are microspheres.

6. The method of claim 2, wherein detecting the presence of the label on the particles comprises measuring an intensity of a signal from the label for each subset of particles, the method comprising correlating the intensity of the signal for a given subset of particles with a quantity of the target nucleic acid of interest captured by that subset of particles.

7. The method of claim 1, wherein providing a solid phase comprises providing a solid support comprising the ten or more capture probes, wherein each capture probe is provided at a different predetermined selected position in an array on the solid support; and
wherein detecting the presence or absence of the different target nucleic acids captured on the solid phase comprises detecting the presence or absence of the label at the selected positions on the solid support, thereby determining which positions on the solid support have a target nucleic acid of interest captured at that position and thereby indicating which of the ten or more different target nucleic acids of interest were present in the sample.

8. The method of claim 7, wherein the ten or more target nucleic acids of interest comprise 100 or more target nucleic acids of interest, wherein the ten or more selected positions comprise 100 or more selected positions, and wherein the ten or more subsets of n capture extenders comprise 100 or more subsets of n capture extenders.

9. The method of claim 7, wherein detecting the presence of the label at the selected positions on the solid support comprises measuring an intensity of a signal from the label, the method comprising correlating the intensity of the signal for a given selected position with a quantity of the target nucleic acid of interest captured at that position.

10. The method of claim 1, wherein n is at least three.

11. The method of claim 10, wherein n is at least five.

12. The method of claim 1, wherein n is at most ten.

13. The method of claim 1, wherein the n capture extenders in a subset hybridize to nonoverlapping polynucleotide sequences in the corresponding target nucleic acid.

14. The method of claim 1, wherein the hybridization temperature is about 5° C. or more greater than the $T_m$.

15. The method of claim 14, wherein the hybridization temperature is about 10° C. or more greater than the $T_m$.

16. The method of claim 1, wherein hybridizing one or more label extenders to target nucleic acids captured on the solid phase comprises providing ten or more subsets of one or more label extenders, wherein each subset of label extenders is capable of hybridizing to one of the target nucleic acids, and hybridizing each target nucleic acid captured on the solid phase to its corresponding subset of label extenders.

17. The method of claim 1, wherein the label probe comprises the label.

18. The method of claim 1, wherein the label is a fluorescent label.

19. The method of claim 1, comprising separating materials not captured on the solid phase from the solid phase.

20. The method of claim 1, wherein each capture probe hybridizes to a single complementary capture extender.

21. The method of claim 1, wherein the capture probes and the capture extenders comprise only naturally occurring bases A, C, G, T, and/or U.

* * * * *